US009296762B2

(12) United States Patent
Lamarque et al.

(10) Patent No.: US 9,296,762 B2
(45) Date of Patent: Mar. 29, 2016

(54) COMPLEXING AGENTS AND CORRESPONDING LANTHANIDE COMPLEXES

(75) Inventors: Laurent Lamarque, St Victor la Coste (FR); Olivier Maury, Brindas (FR); David Parker, Durham (GB); Jurriaan Zwier, Rochefort du Gard (FR); James W. Walton, Hallington Newcastle Upon Tyne (GB); Adrien Bourdolle, Nantes (FR)

(73) Assignees: CISBIO BIOASSAYS, Codolet (FR); CENTRE NATIONAL DE LA RECHERCHE SCIENTIFIQUE (CNRS), Paris (FR); ECOLE NORMALE SUPERIEURE DE LYON, Lyons (FR)

( * ) Notice: Subject to any disclaimer, the term of this patent is extended or adjusted under 35 U.S.C. 154(b) by 0 days.

(21) Appl. No.: 14/233,682

(22) PCT Filed: Jul. 17, 2012

(86) PCT No.: PCT/FR2012/051691
§ 371 (c)(1),
(2), (4) Date: Jul. 25, 2014

(87) PCT Pub. No.: WO2013/011236
PCT Pub. Date: Jan. 24, 2013

(65) Prior Publication Data
US 2014/0336373 A1 Nov. 13, 2014

(30) Foreign Application Priority Data
Jul. 18, 2011 (FR) ..................................... 11 56519

(51) Int. Cl.
| | | |
|---|---|---|
| C07F 5/00 | (2006.01) | |
| C07D 255/02 | (2006.01) | |
| C07F 9/6558 | (2006.01) | |
| C07D 401/14 | (2006.01) | |
| C07D 409/08 | (2006.01) | |
| C07D 401/08 | (2006.01) | |
| C07D 409/14 | (2006.01) | |

(52) U.S. Cl.
CPC .............. *C07F 5/003* (2013.01); *C07D 255/02* (2013.01); *C07D 401/14* (2013.01); *C07F 9/65583* (2013.01)

(58) Field of Classification Search
CPC .... C07D 401/14; C07D 255/02; C07F 5/003; C07F 9/65583
See application file for complete search history.

(56) References Cited

U.S. PATENT DOCUMENTS

| 4,761,481 A | 8/1988 | Hale et al. |
| 4,859,777 A | 8/1989 | Toner |
| 4,920,195 A | 4/1990 | Kankare et al. |
| 5,202,423 A | 4/1993 | Kankare et al. |
| 5,216,134 A | 6/1993 | Mukkala et al. |
| 5,324,825 A | 6/1994 | Kankare et al. |
| 5,457,184 A | 10/1995 | Lehn et al. |
| 5,622,821 A | 4/1997 | Selvin et al. |

FOREIGN PATENT DOCUMENTS

| EP | 0180492 | 5/1986 |
| EP | 0203047 | 11/1986 |
| EP | 0321353 | 6/1989 |
| EP | 0601113 | 6/1994 |
| WO | WO 89/01475 | 2/1989 |
| WO | WO 01/96877 | 12/2001 |
| WO | WO 2005/021538 | 3/2005 |
| WO | WO 2005/058877 | 6/2005 |
| WO | WO 2007/128874 | 11/2007 |
| WO | WO 2008/063721 | 5/2008 |
| WO | WO 2010/034931 | 4/2010 |

OTHER PUBLICATIONS

Kovacs, Z., "A general synthesis of mono- and disubstituted 1, 4, 7-triazacyclononanes." Tetrahedron letters 36.51 (1995): 9269-9272.*
Takalo et al,: "Synthesis and Luminescence of Novel EU$^{III}$ Complexing Agents and Labels with 4-(Phenylethynyl) pyridine Subunits"; Helvetica Chemica Acta, vol. 79 (1996), pp. 789-802.
Latva et al.: "Evaluation of solution structures of highly luminescent europium (III) chelates by using laser induced excitation of the $^7F_0 \rightarrow ^5D_0$ transition"; Inorganica chemical Acta 267 (1998), pp. 63-72.
Kovacs et al.: "A General Synthesis of Mono- and Disubstituted 1,4,7-Triazacyclononanes"; Tetrahedron Letters, vol. 36, No. 51 (1995), pp. 9269-9272.
Latva et al.: "Correlation between the lowest triplet state energy level of the ligand and lanthanide(III) luminescence quantum yield"; Journal of Luminescence 75 (1997), pp. 149-169.
D'Aléo et al.: "Efficient Sensitization of Europium, Ytterbium, and Neodymium Functionalized Tris-Dipicolinate Lanthanide Complexes through Tunable Charge-Transfer Excited States"; Inorganic Chemistry, vol. 47, No. 22(2008), pp. 10258-10268.
Craig et al.: "Towards Tumour Imaging with Indium-111 Labelled Macrocycle-Antibody Conjugates" J. Chem. Soc., Chem. Comnun. (1989), pp. 794-796.
Greg T. Hermanson: "Bioconjugate Techniques"; $2^{nd}$ Edition, Academic Press (2008), pp. 169-211.
Notni et al.: "Zinc Thioate Complexes [ZnL$_n$ (SR)]$^+$ with Azamacrocyclic Ligands: Synthesis and Structural Properties"; European Journal Inorganic Chemistry (2006), pp. 1444-1455.
Cox et al.: "Synthesis of C- and N-Functionalised Derivatives of 1,4,7-Triazacyclonon-ane-1,4,7-triyltriaetic acid (NOTA), 1,4,7,10-Tetra-azacyclododecane-1,4,7,10-tetrayltetra-acetic Acid (DOTA), and Diethylenenetriaminepenta-acetic Acid (DTPA): Bifunctional Complexing Agents for the Derivatisation of Antibodies"; J. Chem. Soc. Perkin Trans. 1 (1990), pp. 2567-2576.
Kovacs et al.: "A General Synthesis of Mono- and Disubstituted 1,4,7-Triazacyclononanes"; Journal Chemical Society; Chemical Communication ,Tetrahedron Letters, vol. 36, No. 51 (1995), pp. 9269-9272.

(Continued)

*Primary Examiner* — Samantha Shterengarts
*Assistant Examiner* — Matt Mauro
(74) *Attorney, Agent, or Firm* — Hamre, Schumann, Mueller & Larson P.C.

(57) ABSTRACT

The present invention concerns complexing agents of formula (I) in which a, b, c, chrom$_1$, chrom$_2$, chrom$_3$, R$_3$, R$_4$ and R$_5$ are as defined in the description. The invention also concerns lanthanide complexes comprising said complexing agents, as well as a method for synthesizing said agents.

25 Claims, 2 Drawing Sheets

(56) References Cited

OTHER PUBLICATIONS

Hovinen et al.: "Synthesis of azamacrocycles via a Mitsunobu reaction"; Tetrahedron Letters, 46 (2005), pp. 4387-4389.
Liang et al.: A Convenient Synthesis of Octahydro-pyrazino [1,2-a] pyrazine; Synthetic Communications, 34 (2004), pp. 845-851.
Wu et al.: "A Practical Sythesis of Hydroxyl-N-Tosylcyclams via Cyclization of 1,3-Dichloro-2-Propanol With Disodium Di (Poly)-N-Tosylamides"; Synthetic Communications, 25 (1995), pp. 1427-1437.
Xue et al.: "A practical synthesis of novel hydroxyl-substituted macrocyclic tri-, tetra- and hexa-amines"; Chinese Journal of Chemistry, vol. 16, No. 6 (1998), pp. 538-541.
Kan et al.: "Efficient macrocyclization by means of 2-nitrobenzenesulfonamide and total synthesis of lipogrammistin-A"; Tetrahedron, 58 (2002), pp. 6267-6276.
Picot et al.: "Two-Photon Antenna Effect Induced in Octupolar Europium Complexes"; Inorganic Chemistry 46 (2007), pp. 2659-2665.
Picot et al.: "Long-Lived Two-Photon Excited Luminescence of Water-Soluble Europium Complex: Applications in Biological Imaging Using Two-Photon Scanning Microscopy"; Journal of American Chemical Society 130 (2008), pp. 1532-1533.
D'Aléo et al.:"Sensitization of Eu(III) luminescence by donor-phenylethynyl-functionalized DTPA and DO3A macrocycles"; C. R. Chimie 13 (2010), pp. 681-690.
Sonogashira et al.: "A Convenient Synthesis of Acetylenes : Catalytic Substitutions of Acetylenic Hydrogen With Bromoalkenes, Iodoarenes, and Bromopyridines"; Tetrahedron Letters, No. 50 (1975), pp. 4467-4470.
Rossi et al.: "Palladium- and/or Copper-Mediated Cross-Coupling Reactions Between 1-Alkynes and Vinyl, Aryl, 1-Alkynyl, 1,2-Propadienyl, Propargyl and Allylic Halides or Related Compounds. A Review"; Organic Preparation and Procedure International 27 (1995), pp. 129-160.
Bourdolle el al.: "Modulating the Photophysical Properties aof Azamacrocyclic Europium Complexes with Charge-Transfer Antenna Chromophores"; Inorganic Chemistry, 50 (2011), pp. 4987-4999.
Ginsburg et al.: "Oximes of the Pyridine Series"; Journal of American Chemical Society, 79 (1957), pp. 481-485.
Narlawar et al.: "Conversion of the LXR-agonist TO-901317—From inverse to normal modulation of γ-secretase by addition of a carboxylic acid and a lipophilic anchor"; Bioorganic & Medical Chemistry Letters, 17 (2007), pp. 5428-5431.
International Search Report, Sep. 6, 2012; PCT/FR2012/051691 (3 pages).

* cited by examiner

COMPLEXING AGENTS AND CORRESPONDING LANTHANIDE COMPLEXES The present invention relates to complexing agents or ligands, to lanthanide complexes, to their use for labeling molecules and for detecting them via time-resolved fluorescence techniques.

PRIOR ART

The use of lanthanide complexes has greatly expanded in the last twenty years in the field of life sciences. The reason for this is that these fluorescent compounds have advantageous spectroscopic characteristics, which make them markers of choice for detecting biological molecules. These fluorescent compounds are particularly suitable for use in conjunction with compatible fluorophores for performing FRET measurements (abbreviation for the term "Förster resonance energy transfer"), whose application for studying interactions between biomolecules is commercially exploited by several companies, including Cisbio Bioassays and its range of HTRF® products (Homogeneous Time-Resolved Fluorescence-Based Assay products; fluorescent reagents for measuring biomolecular interactions). The relatively long life time of lanthanide complexes also makes it possible to perform time-resolved fluorescence measurements, i.e. with a delay after excitation of the fluorophores, which makes it possible to limit fluorescence interferences due to the measuring medium. The latter characteristic is all the more useful when the measuring medium tends toward a biological medium, which comprises numerous proteins whose fluorescence might interfere with that of the compounds under study.

Numerous lanthanide complexes have been described. Latva et al., for example, have disclosed 41 Eu(III) and Tb(III) complexes, of which they studied the luminescence (Journal of Luminescence Volume 75, No. 2, September 1997, Pages 149-169). Compound 39 in particular consists of a 1,4,7-triazacyclononane ring (referred to hereinbelow as "TACN"), the nitrogen atoms of which are substituted with chromophores derived from phenylethynylpyridine. Although the quantic yield for the complex consisting of this chromophore and of Eu(III) is considered good by the authors, this complex is unsuitable for coupling with a biomolecule. Moreover, the use of this compound in aqueous medium may be problematic since it is highly hydrophobic. Finally, the absorption of this complex is optimal at 315 nm, whereas the laser lamps often used in biological assays emit at a wavelength of 337 nm.

D'Aleo et al. have described the synthesis of lanthanide complexes consisting of three ligands derived from dipicolonic acid (Inorg Chem. 2008 Nov. 17; 47(22):10258-68). One of these ligands (L1) consists of a dipicolonic acid molecule substituted with a phenylethynyl group, which itself bears a polyethylene glycol ether-oxide (referred to hereinbelow as "PEG") on the phenyl group. According to the authors, the PEG group gives this product good solubility in aqueous medium and in organic solvents. However, these complexes are insufficiently stable in aqueous medium and cannot be used in a bioconjugation reaction.

International patent application WO 2005/058877 relates to lanthanide complexes, some of which are based on a TACN ring, three of the nitrogen atoms of which are substituted with chromophores consisting of a pyridine derivative, especially phenylpyridine. The inventors moreover propose to include in these compounds a reactive group in order to be able to conjugate them easily with biomolecules. It is thus proposed to include this reactive group via a spacer arm either on a carbon of the TACN ring, or on the pyridine of the chromophore.

Several other lanthanide complexes have been disclosed, and some are commercially exploited: mention may be made in particular of macropolycyclic lanthanide cryptates (EP 0 180 492, EP 0 321 353, EP 0 601 113, WO 2001/96877, WO 2008/063721), lanthanide complexes comprising a coumarin-based unit linked to a diethylenetriamine penta acid unit (U.S. Pat. No. 5,622,821), and those comprising pyridine derivatives (U.S. Pat. No. 4,920,195, U.S. Pat. No. 4,761,481), bipyridine derivatives (U.S. Pat. No. 5,216,134), or terpyridine derivatives (U.S. Pat. No. 4,859,777, U.S. Pat. No. 5,202,423, U.S. Pat. No. 5,324,825).

Patent application WO 89/01475 describes the preparation of trinitrogenous macrocycles, one of the carbon atoms of which bears a group L-Z, and especially 2-(4-N-benzamidyl)butyl-1,4,7-triazacyclonane (intermediate 12). The synthesis of nitrogenous heteromacrocycles in which one of the carbon atoms is substituted is also described by Cox et al. (J. Chem. Soc., Perkin Trans. 1, 1990, 2567-2576) and Craig et al. (J. Chem. Soc., Chem. Commun., 1989, 794-796).

The present invention is directed toward overcoming the drawbacks of the compounds of the prior art, and toward providing fluorescent lanthanide complexes that are brighter than the compounds of the prior art when they are excited at about 337 nm, if possible exhibiting good solubility in aqueous medium, an emission spectrum suited to their use in FRET experiments, and also good practicality for labeling biomolecules.

DESCRIPTION OF THE INVENTION

The problems mentioned previously have been solved by means of complexing agents consisting of a trinitrogenous macrocycle (1,4,7-triazacyclononane, referred to hereinbelow as 147TACN, 1,5,9-triazacyclododecane, referred to hereinbelow as 159TACD, 1,4,8-triazacyclodecane, referred to hereinbelow as 148TACD or 1,4,8-triazacycloundecane, referred to hereinbelow as 148TACU), the nitrogen atoms of which are substituted with chromophores of phenylethynylpyridine type, these chromophores comprising from one to three groups which affect the electron density of the molecule (referred to hereinbelow as "O-donating", "S-donating", "NHCO-donating", "SCO-donating", "NHCS-donating", "SCS-donating" or lower alkyl group) directly linked to the phenyl group, and optionally at least one polyethylene glycol (PEG) group which gives the molecule good solubility in aqueous medium. These compounds may also comprise a reactive group for conjugating them with a molecule to be labeled. The complexing agents according to the invention form stable complexes with lanthanides, and may be used to produce fluorescent conjugates of molecules of interest. The lanthanide complexes according to the invention have excellent photophysical properties, in particular as regards their quantic yield, their luminescence life time and their excitation spectrum, which is particularly suited to laser excitation at about 337 nm. The presence of three chromophores significantly increases the molar absorption coefficient (epsilon) and consequently the brightness of the complex. The brightness (quantic yield×molar absorption coefficient) of these complexes in biological media is also better than that of the compounds of the prior art.

Complexing Agents

The complexing agents according to the invention are compounds of formula (I):

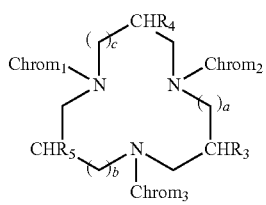
(I)

in which:

either a=b=c=1 (1,5,9-triazacyclododecane), or a=b=c=0 (1,4,7-triazacyclononane), or a=1 and b=c=0 (1,4,8-triazacyclodecane), or a=b=1 and c=0 (1,4,8-triazacycloundecane);

$R_3$, $R_4$ and $R_5$ are each chosen from the following groups or atoms: H, -L-G;

Chrom$_1$, Chrom$_2$ and Chrom$_3$ are identical or different chromophores and all three correspond to only one of the following formulae:

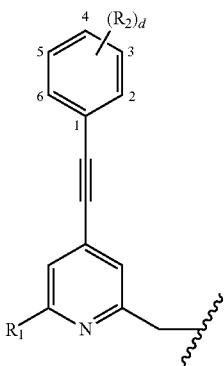
(IIa)

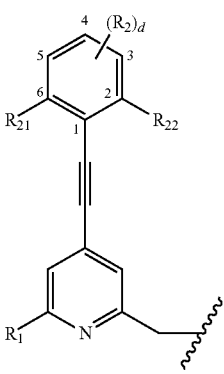
(IIb)

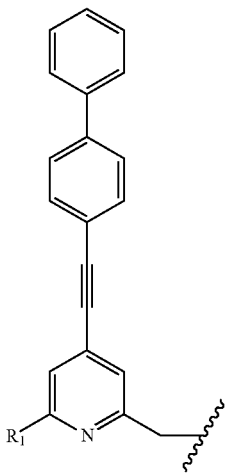
(IIc)

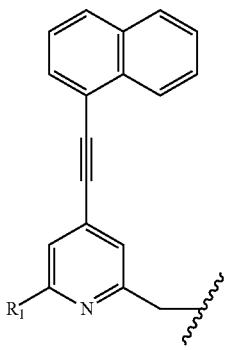
(IId)

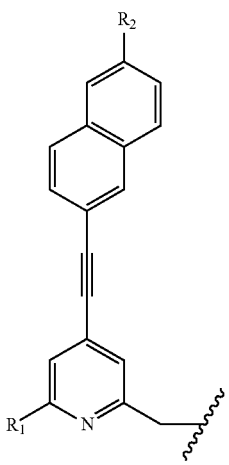
(IIe)

(IIf)

-continued

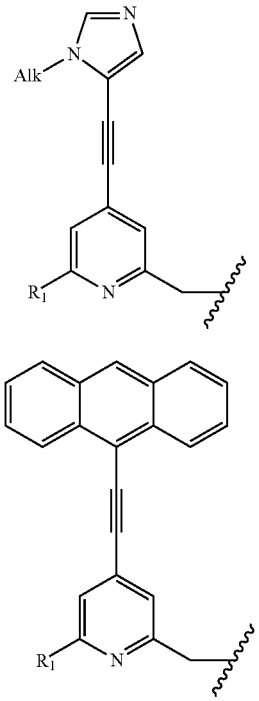

(IIg)

(IIh)

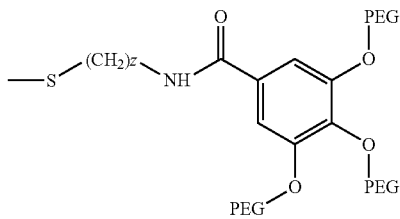

in which z is an integer between 1 and 5;

NHCO-donating groups chosen from: —NHCO-L-G; —NHCO(OAlk); —NHCO(NHAlk); —NHCO(NAlk1Alk2); —NHCO(SAlk); —NHCO(Alk); —NHCO-PEG; —NHCO-phenyl; a group of formula:

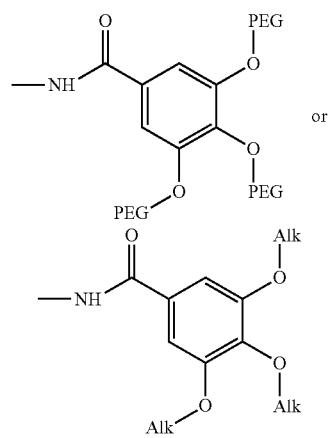

SCO-donating groups chosen from: —SCO-L-G; —SCO(OAlk); —SCO(NHAlk); —SCO(NAlk$_1$Alk$_2$); —SCO(SAlk); —SCO(Alk); —SCO-PEG;

NHCS-donating groups chosen from: —NHCS(OAlk); —NHCS(NHAlk); —NHCS(NAlk$_1$Alk$_2$); —NHCS(SAlk); —NHCS(Alk); —NHCS-PEG; —NHCS-L-G;

SCS-donating groups chosen from: —SCS(OAlk); —SCS(NHAlk); —SCS(NAlk$_1$Alk$_2$); —SCS(SAlk); —SCS(Alk); —SCS-PEG; —SCS-L-G;

PEG is a group of formula —CH$_2$—(CH$_2$OCH$_2$)$_y$—CH$_2$OCH$_3$, y being an integer ranging from 1 to 5;

Alk, Alk1 and Alk2 are each a linear or branched C$_1$-C$_{10}$ alkyl optionally substituted with an —O-PEG group;

L is a spacer arm;

G is a reactive group for linking the complex or the complexing agent to a molecule to be labeled;

it being understood that:

when $R_{22}$ and $R_{21}$ are alkyl groups, d=1 and when one of the groups $R_{22}$ or $R_{21}$ is an alkyl group and the other is a hydrogen atom, d=1 or d=2;

when $R_2$ comprises a group -L-G, $R_3$=$R_4$=$R_5$=H;

when $R_2$ does not comprise a group -L-G, either one of the groups $R_3$, $R_4$ and $R_5$ is a group -L-G or $R_3$=$R_4$=$R_5$=H; and when several groups $R_2$ are present, at least one is in position 4 of the benzene ring.

in which d is an integer ranging from 1 to 3;

each $R_1$ is chosen from the following groups: —COOH, —PO(OH)R$_6$, R$_6$ representing a group chosen from: phenyl, benzyl, methyl, ethyl, propyl, n-butyl, sec-butyl, isobutyl, tert-butyl;

$R_{21}$ and $R_{22}$ represent, independently of each other, a hydrogen atom or a linear or branched alkyl comprising from 1 to 6 carbon atoms;

each $R_2$ is chosen from the following groups:

linear or branched alkyl groups comprising from 1 to 6 carbon atoms optionally substituted with a PEG group;

O-donating groups chosen from: OH; —OPhenyl; —O—CH$_2$—CO—N-Alk; —O—CH$_2$—CO—O-Alk; —O—CH$_2$—CO—NH; —O—CH$_2$—CO—OH; O—CH$_2$—CO—N-LG; —O—CH$_2$—CO—O-L-G; —O-L-G; —O-Alk; —O-PEG; the group of formula:

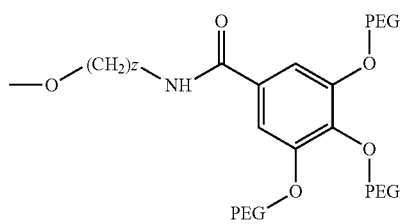

in which z is an integer ranging from 1 to 5;

S-donating groups chosen from: —S-L-G; —S-Alk; —S-PEG; the group of formula:

Preferably, $Chrom_1$, $Chrom_2$ and $Chrom_3$ are identical or different chromophores and all three correspond to only one of the following formulae:

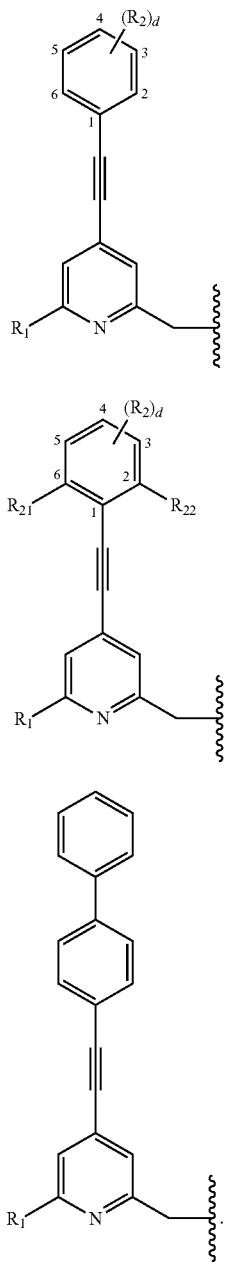

The invention relates in particular to the complexing agents of formula (I):

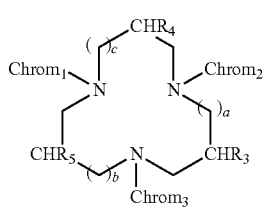

in which:
either $a=b=c=1$ (1,5,9-triazacyclododecane), or $a=b=c=0$ (1,4,7-triazacyclononane), or $a=1$ and $b=c=0$ (1,4,8-triazacyclodecane), or $a=b=1$ and $c=0$ (1,4,8-triazacycloundecane);

$R_3$, $R_4$ and $R_5$ are each chosen from the following groups or atoms: H, -L-G;

$Chrom_1$, $Chrom_2$ and $Chrom_3$ are identical or different chromophores of formula (II):

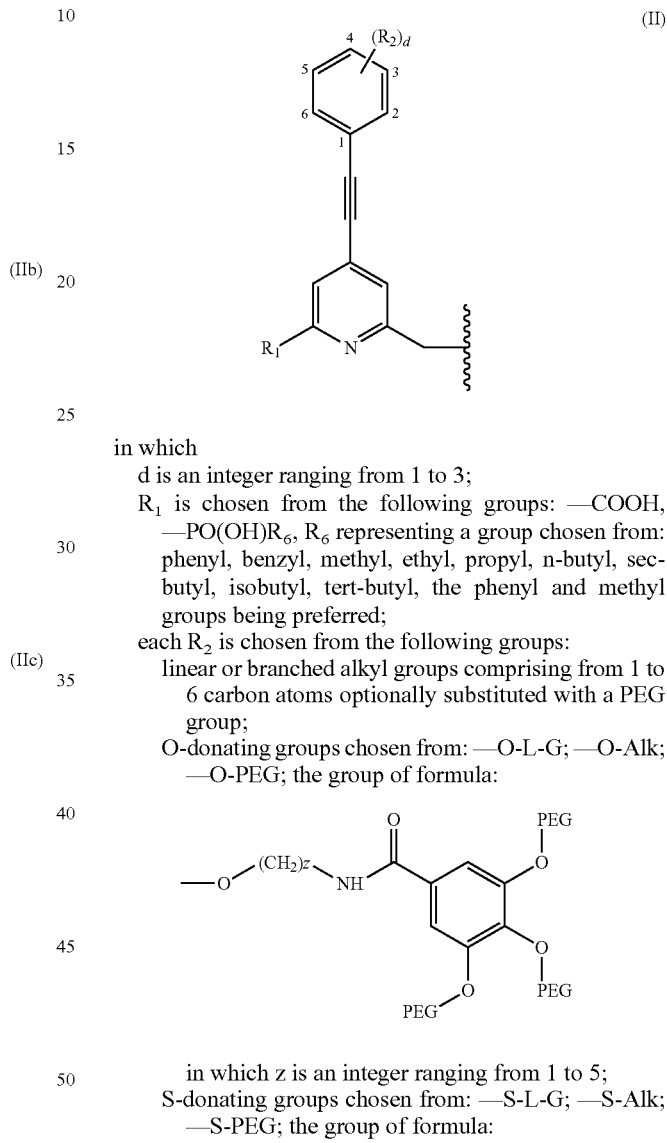

in which
d is an integer ranging from 1 to 3;
$R_1$ is chosen from the following groups: —COOH, —PO(OH)$R_6$, $R_6$ representing a group chosen from: phenyl, benzyl, methyl, ethyl, propyl, n-butyl, sec-butyl, isobutyl, tert-butyl, the phenyl and methyl groups being preferred;
each $R_2$ is chosen from the following groups:
  linear or branched alkyl groups comprising from 1 to 6 carbon atoms optionally substituted with a PEG group;
  O-donating groups chosen from: —O-L-G; —O-Alk; —O-PEG; the group of formula:

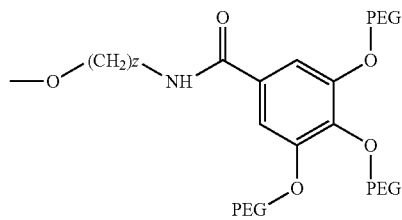

in which z is an integer ranging from 1 to 5;
S-donating groups chosen from: —S-L-G; —S-Alk; —S-PEG; the group of formula:

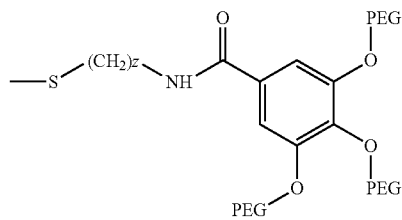

in which z is an integer ranging from 1 to 5;
NHCO-donating groups chosen from: —NHCO-L-G; —NHCO(OAlk); —NHCO(NHAlk); —NHCO(NAlk$_1$Alk$_2$); —NHCO(SAlk); —NHCO(Alk); —NHCO-PEG; the group of formula:

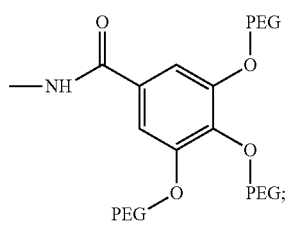

SCO-donating groups chosen from: —SCO-L-G; —SCO(OAlk); —SCO(NHAlk); —SCO(NAlk$_1$Alk$_2$); —SCO(SAlk); —SCO(Alk); —SCO-PEG;

NHCS-donating groups chosen from: —NHCS(OAlk); —NHCS(NHAlk); —NHCS(NAlk$_1$Alk$_2$); —NHCS(SAlk); —NHCS(Alk); —NHCS-PEG; —NHCS-L-G;

SCS-donating groups chosen from: —SCS(OAlk); —SCS(NHAlk); —SCS(NAlk$_1$Alk$_2$); —SCS(SAlk); —SCS(Alk); —SCS-PEG; —SCS-L-G;

PEG is a group of formula —CH$_2$—(CH$_2$OCH$_2$)y-CH$_2$OCH$_3$, y being an integer ranging from 1 to 5;

Alk, Alk1 and Alk2 are each a linear or branched C$_1$-C$_{10}$ alkyl optionally substituted with an —O-PEG group;

L is a spacer arm;

G is a reactive group for linking the complex or the complexing agent to a molecule to be labeled;

it being understood that:
when R$_2$ comprises a group -L-G, R$_3$=R$_4$=R$_5$=H;
when R$_2$ does not comprise a group -L-G, either one of the groups R$_3$, R$_4$ and R$_5$ is a group -L-G, or R$_3$=R$_4$=R$_5$=H; and
when several groups R$_2$ are present, at least one is in position 4 of the benzene ring.

A preferred family of compounds of formula (I) comprises the compounds in which:
either chrom$_1$, chrom$_2$ and chrom$_3$ are identical and are each substituted with one to three groups R$_2$ not comprising a group -L-G, and the groups R$_3$-R$_5$ are hydrogen atoms;
or chrom$_1$, chrom$_2$ and chrom$_3$ are identical and are substituted with one to three groups R$_2$ not comprising a group -L-G, and one of the groups R$_3$-R$_5$ is a group L-G, the others being hydrogen atoms;
or two of the groups chrom$_1$, chrom$_2$ and chrom$_3$ are identical and are each substituted with one to three groups R$_2$ not comprising a group -L-G and the third chromophore is substituted with a group R$_2$ comprising a group -L-G, the groups R$_3$-R$_5$ are hydrogen atoms.

The following subfamilies of complexing agents are preferred:
compounds of formula (I) characterized in that one of the groups R$_2$ comprises a group -L-G;
compounds of formula (I) characterized in that one of the groups R$_3$, R$_4$ or R$_5$ comprises a group -L-G;
compounds of formula (I) characterized in that they do not comprise any group -L-G.

Among the compounds of formula (I) and those belonging to the abovementioned subfamilies, the following compounds are preferred:
those which are characterized in that a=b=c=1 (1,5,9-triazacyclododecane, 159TACD);
those which are characterized in that a=b=c=0 (1,4,7-triazacyclononane, 147TACN);
those which are characterized in that a=1 and b=c=0 (1,4,8-triazacyclodecane, 148TACD);
those which are characterized in that a=b=1 and c=0 (1,4,8-triazacycloundecane, 148TACU).

Among the compounds of formula (I) and those belonging to the abovementioned subfamilies, the compounds having the following characteristics are also preferred:
compounds characterized in that the groups R$_1$ of the chromophores chrom$_1$, chrom$_2$ and chrom$_3$ are —COOH groups;
compounds characterized in that the groups R$_1$ of the chromophores chrom$_1$, chrom$_2$ and chrom$_3$ are groups —PO(OH)R$_6$;
compounds characterized in that the group R$_1$ of the chromophore chrom$_1$ is a —COOH group and the groups R$_1$ of the chromophores chrom$_2$ and chrom$_3$ are groups —PO(OH)R$_6$;
compounds characterized in that the group R$_1$ of the chromophore chrom$_1$ is a group —PO(OH)R$_6$ and the groups R$_1$ of chromophores chrom$_2$ and chrom$_3$ are —COOH groups.

One of the essential technical characteristics of the compounds according to the invention is the presence, on the chromophores, of groups R$_2$ which affect the electron density of the molecule and contribute to the good spectroscopic properties of these compounds. Thus, among the compounds of formula (I) and those belonging to the abovementioned subfamilies, the compounds in which the donating groups R$_2$ are the following are preferred:
compounds characterized in that the groups R$_2$ are linear or branched alkyl groups comprising from 1 to 6 carbon atoms optionally substituted with a PEG group;
compounds characterized in that the groups R$_2$ are O-donating groups chosen from: —O-L-G; —O-Alk; —O-PEG; the group of formula:

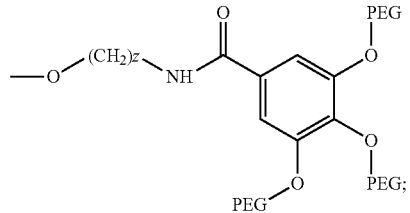

compounds characterized in that the groups R$_2$ are S-donating groups chosen from: —S-L-G; —S-Alk; —S-PEG; the group of formula:

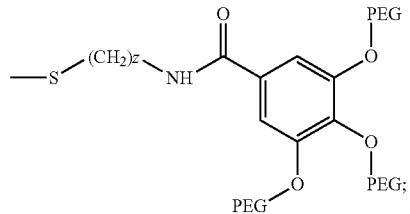

compounds characterized in that the groups R$_2$ are NHCO-donating groups chosen from: —NHCO-L-G; —NHCO(OAlk); —NHCO(NHAlk); —NHCO(NAlk$_1$Alk$_2$); —NHCO(SAlk); —NHCO(Alk); —NHCO-PEG; the group of formula:

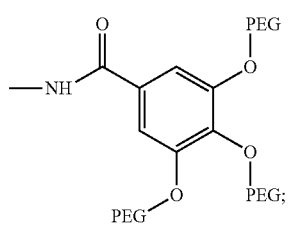

compounds characterized in that the groups $R_2$ are SCO-donating groups chosen from: —SCO-L-G; —SCO(OAlk); —SCO(NHAlk); —SCO(NAlk$_1$Alk$_2$); —SCO(SAlk); —SCO(Alk); —SCO-PEG;

compounds characterized in that the groups $R_2$ are NHCS-donating groups chosen from: —NHCS(OAlk); —NHCS(NHAlk); —NHCS(NAlk$_1$Alk$_2$); —NHCS(SAlk); —NHCS(Alk); —NHCS-PEG; —NHCS-L-G;

compounds characterized in that the groups $R_2$ are SCS-donating groups chosen from: —SCS(OAlk); —SCS(NHAlk); —SCS(NAlk$_1$Alk$_2$); —SCS(SAlk); —SCS(Alk); —SCS-PEG; —SCS-L-G.

The compounds according to the invention comprise from one to three groups $R_2$ per chromophore, and preferably comprise:

only one group $R_2$ in position 4 of the phenyl group, or alternatively a group $R_2$ in position 4 and a group $R_2$ in position 3 of the phenyl group, or alternatively a group $R_2$ in position 4 and a group $R_2$ in position 5 of the phenyl group, or alternatively a group $R_2$ in position 4 and a group $R_2$ in position 2 of the phenyl group, or alternatively a group $R_2$ in position 4 and a group $R_2$ in position 6 of the phenyl group, or alternatively a group $R_2$ in position 4, a group $R_2$ in position 3 and a group $R_2$ in position 5 of the phenyl group, or alternatively a group $R_2$ in position 4, a group $R_2$ in position 2 and a group $R_2$ in position 6 of the phenyl group.

When several groups $R_2$ are present on a chromophore, they are preferably identical.

Finally, the preceding compounds characterized in that they comprise at least one PEG group are also preferred.

Table 1 represents various families of preferred compounds according to the invention: these compounds correspond to the general formula (I) and some of their characteristics are indicated in the first column (type of trinitrogenous macrocycle) and the first line (nature of the substituents $R_2$ and $R_1$ of the chromophores). Each "+" sign represents a preferred family of compounds. Thus, the case corresponding to the intersection of the first column and of the first line denotes the family of compounds comprising a ring 147TACN, the chromophores of which bear groups $R_2$ which are donating alkyl groups and in which the three groups $R_1$ are COOH groups. The abbreviation "$R_1$: (COOH), 2(POOHR$_6$)" means that one of the groups $R_1$ is a COOH group and the other two groups $R_1$ are groups POOHR$_6$).

TABLE 1

| | $R_2$: Alkyl-donating $R_1$: 3(COOH) | $R_2$: Alkyl-donating $R_1$: 3(POOHR$_6$) | $R_2$: Alkyl-donating $R_1$: (COOH) 2(POOHR$_6$) | $R_2$: Alkyl-donating $R_1$: 2(COOH) (POOHR$_6$) | $R_2$: O-donating $R_1$: 3(COOH) | $R_2$: O-donating $R_1$: 3(POOHR$_6$) | $R_2$: O-donating $R_1$: (COOH) 2(POOHR$_6$) | $R_2$: O-donating $R_1$: 2(COOH) (POOHR$_6$) |
|---|---|---|---|---|---|---|---|---|
| 147TACN | + | + | + | + | + | + | + | + |
| 159TACD | + | + | + | + | + | + | + | + |
| 148TACD | + | + | + | + | + | + | + | + |
| 148TACU | + | + | + | + | + | + | + | + |

| | $R_2$: S-donating $R_1$: 3(COOH) | $R_2$: S-donating $R_1$: 3(POOHR$_6$) | $R_2$: S-donating $R_1$: (COOH) 2(POOHR$_6$) | $R_2$: S-donating $R_1$: 2(COOH) (POOHR$_6$) |
|---|---|---|---|---|
| 147TACN | + | + | + | + |
| 159TACD | + | + | + | + |
| 148TACD | + | + | + | + |
| 148TACU | + | + | + | + |

| | $R_2$: NHCO-donating $R_1$: 3(COOH) | $R_2$: NHCO-donating $R_1$: 3(POOHR$_6$) | $R_2$: NHCO-donating $R_1$: (COOH) 2(POOHR$_6$) | $R_2$: NHCO-donating $R_1$: 2(COOH) (POOHR$_6$) | $R_2$: SCO-donating $R_1$: 3(COOH) | $R_2$: SCO-donating $R_1$: 3(POOHR$_6$) | $R_2$: SCO-donating $R_1$: (COOH) 2(POOHR$_6$) | $R_2$: SCO-donating $R_1$: 2(COOH) (POOHR$_6$) |
|---|---|---|---|---|---|---|---|---|
| 147TACN | + | + | + | + | + | + | + | + |
| 159TACD | + | + | + | + | + | + | + | + |
| 148TACD | + | + | + | + | + | + | + | + |
| 148TACU | + | + | + | + | + | + | + | + |

| | $R_2$: NHCS-donating $R_1$: 3(COOH) | $R_2$: NHCS-donating $R_1$: 3(POOHR$_6$) | $R_2$: NHCS-donating $R_1$: (COOH) 2(POOHR$_6$) | $R_2$: NHCS-donating $R_1$: 2(COOH) (POOHR$_6$) | $R_2$: SCS-donating $R_1$: 3(COOH) | $R_2$: SCS-donating $R_1$: 3(POOHR$_6$) | $R_2$: SCS-donating $R_1$: (COOH) 2(POOHR$_6$) | $R_2$: SCS-donating $R_1$: 2(COOH) (POOHR$_6$) |
|---|---|---|---|---|---|---|---|---|
| 147TACN | + | + | + | + | + | + | + | + |
| 159TACD | + | + | + | + | + | + | + | + |
| 148TACD | + | + | + | + | + | + | + | + |
| 148TACU | + | + | + | + | + | + | + | + |

For each of the families of compounds of table 1, the following subfamilies are preferred:

compounds characterized in that one of the groups $R_2$ comprises a group -L-G;

compounds characterized in that one of the groups $R_3$, $R_4$ or $R_5$ comprises a group -L-G;

compounds characterized in that they do not comprise any group -L-G.

Moreover, for each of the families of table 1, the compounds comprise from one to three groups $R_2$ per chromophore, and preferably comprise:

only one group $R_2$ in position 4 of the phenyl group, or alternatively a group $R_2$ in position 4 and a group $R_2$ in position 3 of the phenyl group, or alternatively a group $R_2$ in position 4 and a group $R_2$ in position 5 of the phenyl group, or alternatively a group $R_2$ in position 4 and a group $R_2$ in position 2 of the phenyl group, or alternatively a group $R_2$ in position 4 and a group $R_2$ in position 6 of the phenyl group, or alternatively a group $R_2$ in position 4, a group $R_2$ in position 3 and a group $R_2$ in position 5 of the phenyl group, or alternatively a group $R_2$ in position 4, a group $R_2$ in position 2 and a group $R_2$ in position 6 of the phenyl group.

The compounds of table 1 characterized in that they comprise at least one PEG group are also preferred.

Finally, when the compounds of table 1 comprise a group $R_6$, it is preferentially a methyl or phenyl group.

A subject of the invention is also the compounds, ligands and complexes described in table 2.

The reactive group G borne by a spacer arm L makes it possible to couple the compounds according to the invention with a species which it is desired to make fluorescent, for example an organic molecule, a peptide or a protein. The techniques for conjugating two organic molecules are based on the use of reactive groups and fall within the general knowledge of a person skilled in the art. These standard techniques are described, for example, in Bioconjugate Techniques, G. T. Hermanson, Academic Press, Second Edition 2008, p. 169-211.

Typically, the reactive group is an electrophilic or nucleophilic group which can form a covalent bond when it is placed in the presence of a suitable nucleophilic or electrophilic group, respectively. The conjugation reaction between a compound according to the invention comprising a reactive group and an organic molecule, a peptide or a protein bearing a functional group leads to the formation of a covalent bond comprising one or more atoms of the reactive group.

Preferably, the reactive group G is a group derived from one of the compounds below: an acrylamide, an activated amine (for example a cadaverine or an ethylenediamine), an activated ester, an aldehyde, an alkyl halide, an anhydride, an aniline, an azide, an aziridine, a carboxylic acid, a diazoalkane, a haloacetamide, a halotriazine, such as monochlorotriazine, dichlorotriazine, a hydrazine (including hydrazides), an imido ester, an isocyanate, an isothiocyanate, a maleimide, a sulfonyl halide, or a thiol, a ketone, an amine, an acid halide, a hydroxysuccinimidyl ester, a hydroxysulfosuccinimidyl ester, an azidonitrophenyl, an azidophenyl, a 3-(2-pyridyldithio)propionamide, a glyoxal, a triazine, an acetylenic group, and in particular the groups of formula:

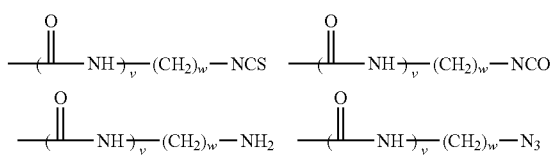

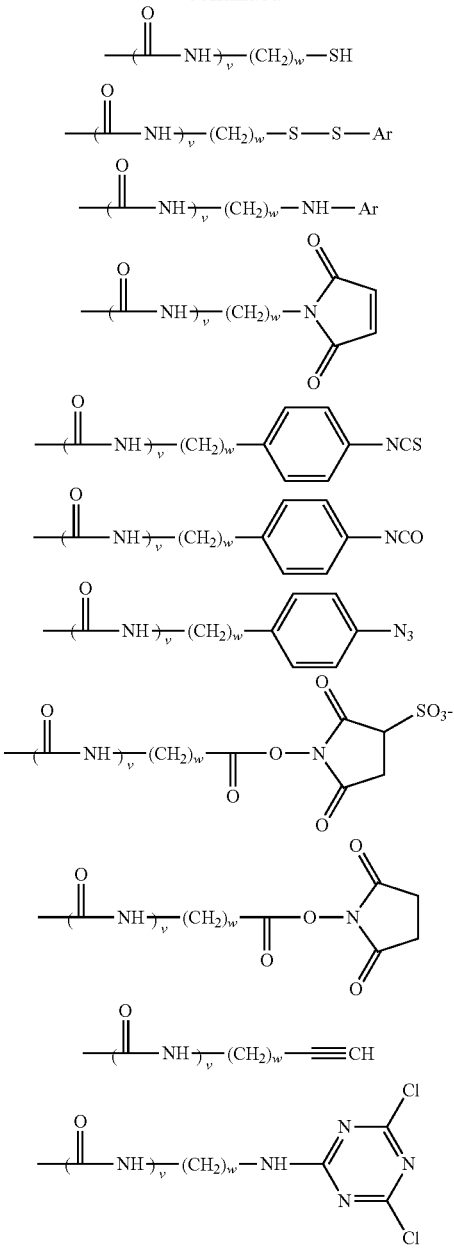

in which w ranges from 0 to 8 and v is equal to 0 or 1, and Ar is a saturated or unsaturated, 5- or 6-membered heterocycle comprising 1 to 3 heteroatoms, optionally substituted with a halogen atom.

Preferably, the reactive group G is a carboxylic acid, an amine, a succinimidyl ester, a haloacetamide, a hydrazine, an isothiocyanate, a maleimide group or an aliphatic amine.

These reactive groups may be directly linked to the complexing agent via a covalent bond or alternatively via a spacer arm advantageously consisting of a divalent organic radical, chosen from linear or branched $C_1$-$C_{20}$ alkylene groups, optionally containing one or more double or triple bonds; $C_5$-$C_8$ cycloalkylene groups and $C_6$-$C_{14}$arylene groups, said alkylene, cycloalkylene or arylene groups optionally containing one or more heteroatoms, such as oxygen, nitrogen, sulfur or phosphorus or one or more carbamoyl or carboxamide groups, and said alkylene, cycloalkylene or arylene groups being optionally substituted with $C_1$-$C_8$ alkyl, $C_6$-$C_{14}$ aryl, sulfonate or oxo groups.

In particular, the spacer arms may be chosen from the following divalent groups:

1)

2)
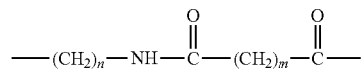

3)

4)
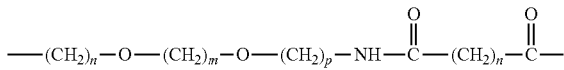

5)
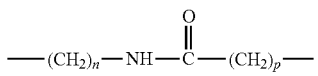

6)
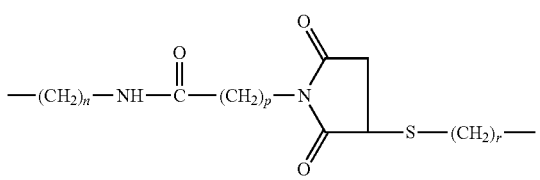

7)
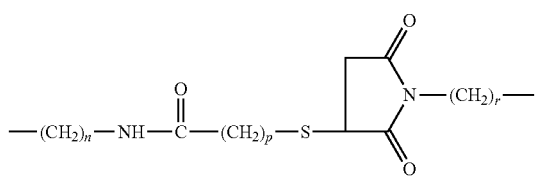

8)
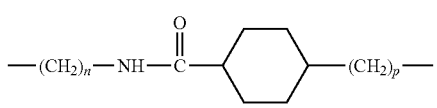

9)
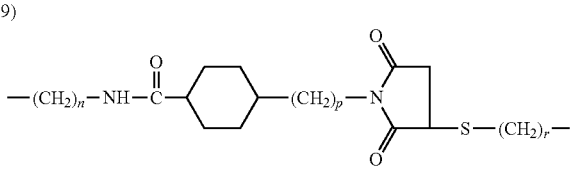

10)
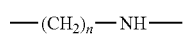

11)
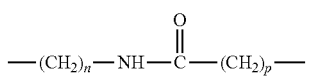

12)

13)
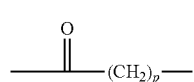

in which n, m, p and r are integers from 1 to 16 and preferably from 1 to 5.

Preferably, the group -LG consists of a reactive group G chosen from: a carboxylic acid, an amine, a succinimidyl ester, a haloacetamide, a hydrazine, an isothiocyanate, a maleimide group, an aliphatic amine, and of a spacer arm L consisting of an alkylene chain comprising from 1 to 5 carbon atoms. Even more preferably, the group -LG is an amine borne by an alkylene chain comprising from 1 to 5 carbon atoms.

An organic molecule, a peptide or a protein that is capable of being labeled with a compound according to the invention will thus comprise a functional group with which will react the reactive group of the lanthanide complex or of the complexing agent. For example, the organic molecule, the protein or the peptide comprises one of the following groups: amine, amide, thiol, alcohol, aldehyde, ketone, hydrazine, hydroxylamine, secondary amine, halide, epoxide, ester (alkyl carboxylate), carboxylic acid, groups comprising double bonds or a combination of these functional groups. The amine or thiol groups naturally present on the proteins are often used for performing the labeling of these molecules.

Complexes

The invention also relates to lanthanide complexes consisting of a lanthanide atom complexed with a complexing agent as described above, the lanthanide being chosen from: $Eu^{3+}$, $Tb^{3+}$, $Gd^{3+}$, $Dy^{3+}$, $Nd^{3+}$, $Er^{3+}$. Preferably, the lanthanide is $Tb^{3+}$ or $Eu^{3+}$ and even more preferably $Eu^{3+}$.

These complexes are prepared by placing the complexing agents according to the invention in contact with a lanthanide salt. Thus, the reaction between one equivalent of complexing agent and 1 to 5 equivalents of lanthanide salt (europium or terbium in the form of chlorides, acetates or triflates) in a solvent (acetonitrile, methanol or another solvent that is compatible with these salts) at reflux for several hours leads to the corresponding complex.

As indicated previously, the fluorescent complexes obtained have excellent photophysical properties, in particular as regards their quantic yield, the life time of their luminescence and their excitation spectrum which is particularly suitable for laser excitation at about 337 nm. Furthermore, the distribution of the bands of their emission spectra is centered at about 620 nm, thus giving the complexes exceptional and very favorable properties in a FRET use with acceptors of cyanine or allophycocyanine type (such as XL665 sold by Cisbio Bioassays). Due to the great stability of these complexes in biological media containing divalent cations ($Mn^{2+}$, $Ca^{2+}$, $Mg^{2+}$, etc.) or EDTA, their luminescence remains excellent when compared with the complexes of the prior art.

Conjugates

The complexing agents and complexes according to the invention comprising a reactive group are particularly suitable for the labeling of organic or biological molecules comprising a functional group that is capable of reacting with the reactive group to form a covalent bond. Thus, the invention also relates to the use of complexes for the labeling of biological molecules (proteins, antibodies, enzymes, hormones, etc.).

The invention also relates to molecules labeled with a complex according to the invention. Any organic or biological molecule may be conjugated with a complex according to the invention if it bears a functional group that is capable of reacting with the reactive group. In particular, the conjugates according to the invention comprise a complex according to the invention and a molecule chosen from: an amino acid, a peptide, a protein, an antibody, a sugar, a carbohydrate chain, a nucleoside, a nucleotide, an oligonucleotide, an enzyme substrate (in particular a suicide enzyme substrate such as a benzylguanine or a benzylcytosine (enzyme substrates sold under the names SNAP-TAG® (a self-labeling protein tag) and CLIP-TAG® (a self-labeling protein tag)), a chloroalkane (enzyme substrate sold under the name HALOTAG® (a protein fusion tag)), coenzyme A (enzyme substrate sold under the name ACPtag or MCPtag).

Synthesis

The preparation of the complexing agents (ligands) and of the complexes according to the invention is described schematically hereinbelow, and in a more detailed manner in the experimental section.

Synthesis of the macrocycles 1,4,7-triazacyclononane (147TACN), 1,5,9-triazacyclododecane (TACD), 1,4,8-triazacyclodecane (1,4,8TACD) and 1,4,8-triazacycloundecane (148TACU)

Several processes for synthesizing the rings 147TACN and 159TACD have been described and the trihydrochloride salts of 147TACN and 159TACD are commercially available. The azamacrocycles 148TACD and 148TACU may be prepared using the procedure described by Anders et al. (European Journal Inorganic Chemistry (2006) 1444-1455).

When the three chromophores grafted on the macrocycle are not identical, i.e. when one of them bears a reactive group -L-G to allow conjugation of the product with a compound to be labeled, the synthesis of the products according to the invention requires the use of trinitrogenous macrocycles, one or two of the secondary amines of which are protected with protecting groups. Parker et al. have described the synthesis of TACN compounds in which one of the amines is protected with a benzoyl group (Journal Chemical Society Perkin Trans 1 (1990) 2567), but the deprotection of the amine is not compatible with the synthesis of the compounds according to the invention.

The compounds 147TACN, 159TACD, 148TACD and 148TACU monoprotected according to the invention bear an amine protected with a group that is resistant to hydrogenation, for example with a carbamate group (Boc). These compounds are not commercially available, the elements published in the literature do not allow their synthesis (absence of experimental procedures) and it is also impossible to prepare them directly and in a suitable yield since the formation of the di- and trisubstituted macrocycles is favored (Kovacs et al. Journal Chemical Society, Chemical Communication 36 (1995) 9269-9272). In the light of these technical problems, another strategy was developed (SCHEME 4). It is based on the preference of the trinitrogenous macrocycles (147TACN, 159TACD, 148TACD and 148TACU) for disubstitution by first protecting two amines of the macrocycles with a protecting group P, orthogonal to the Boc group or to any other group that is resistant to hydrogenation, i.e. whose deprotection conditions are different from those of the Boc group. The choice of the group P led to the protecting group Cbz as proposed in the literature by using Cbz-ON (2-benzyloxycarbonyloxyimino)-2-phenylacetonitrile) as precursor. However, since this compound is not commercial, the synthesis was developed using one of its analogs, Moz-ON ((2-(4-methoxybenzyloxycarbonyloxyimino)-2-phenylacetonitrile), which is, itself, available.

As described with Cbz-ON, two equivalents of Moz-ON were condensed on the trinitrogenous macrocycle to give the disubstituted compounds in suitable yields. The purification of these products proved to be difficult since the Moz group is acid-sensitive. Even the acidity of silica is sufficient to bring about degradation of the products during purification on a chromatography column. To avoid this degradation, the reaction media were purified on a column of neutral alumina, which made it possible to give, for example, compounds 28a and 28b in respective yields of 74% and 34%. In the following step, the Boc group is introduced by means of N-(tert-butoxycarbonyloxy)succinimide to give, for example, the trisubstituted trinitrogenous macrocycles 29a and 29b. Finally, the amines bearing the Moz groups are deprotected by hydrogenolysis. The use of 10% Pd/C as catalyst did not make it possible to deprotect the amines when the reaction medium is hydrogenated for 48 hours at a pressure of 3.45 bar. On the other hand, the use of the Pearlman catalyst (Pd(OH)$_2$/C) made it possible to obtain monoprotected trinitrogenous macrocycles. In order easily to isolate these products, the hydrochloride salts were formed by addition of a small amount of cold hydrochloric acid, the salts being collected by precipitation from diethyl ether. This methodology now makes it possible to prepare on a scale of several grams compounds (147TACN, 159TACD, 148TACD and 148TACU) monoprotected with a Boc group, for example 30a and 30b.

The method for synthesizing the monoprotected trinitrogenous macrocycles according to the invention thus comprises the following steps:
  (i) protection of two of the three amines of the trinitrogenous macrocycle with a hydrogenation-sensitive protecting group Pg$_1$;
  (ii) purification of the disubstituted compounds on a column chosen from: a basic alumina column; a silica column which has undergone a pretreatment with triethylamine or ammonia; a basic or neutral alumina column, the latter being preferred;
  (iii) protection of the third amine of said trinitrogenous macrocycle with a second hydrogenation-insensitive protecting group Pg$_2$;
  (iv) deprotection of the amines protected with the protecting groups Pg$_1$ by hydrogenation, preferably with Pearlman's catalyst;
  (v) purification of the monoprotected products, for example by formation of dihydrochloride salts by adding cold hydrochloric acid and precipitation from diethyl ether.

Pg$_1$ and Pg$_2$ are chosen from amine-protecting groups, which are known to those skilled in the art, as described in Protecting Groups P. J. Kocieński, Corrected Edition (2000) 185-244: Carbobenzyloxy (Cbz), p-Methoxybenzylcarbonyl (Moz) tert-Butyloxycarbonyl (Boc), 9-Fluorenylmethyloxycarbonyl (Fmoc), Acetyl (Ac), Benzoyl (Bz), Benzyl (Bn), p-Methoxybenzyl (PMB), 3,4-Dimethoxybenzyl (DMPM), p-methoxyphenyl (PMP), Tosyl (Ts), Nosyl (Ns), trifluoroacetamides, alkoxycarbonyls, allyloxycarbonyl (Aloc), 2-(trimethylsilyl)ethoxycarbonyl, 2,2,2-trichloroethoxycarbonyl (Troc), 2-(trimethylsilyl)ethoxycarbonyl (Teoc), B-(trimethylsilyl)ethanesulfonyl (SES), benzhydryl, trityl, 9-phenylfluorenyl and N-silyl imines.

Pg$_1$ is preferentially a Cbz or Moz group.

As regards Pg$_2$, the Fmoc, Tosyl, Nosyl and Boc(trimethylsilyloxy) groups are preferred, the Boc group being even more preferred.

The compound obtained is a compound having the following formula:

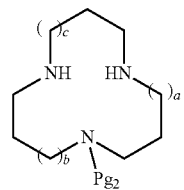

in which a=b=c=0 or a=b=c=1. The compound in which Pg$_2$ is the Boc group is preferred. It is understood on reading the synthetic method just described above, and in particular step (v), that the monoprotected trinitrogenous macrocycles according to the invention are in the form of the dihydrochloride salt.

The preparation of the complexing agents of formula (I) in which R$_3$, R$_4$ or R$_5$ is a group -L-G requires the use of particular macrocycles in which carbon 2 or 3 is substituted with the group -L-G, or with a precursor of this group, especially a precursor in which the reactive group is in protected form. The synthesis of some of these azamacrocycles is described especially in international patent application WO 2005/058877, and also by Hovinen et al. (Tetrahedron Letters 46 (2005) 4387-4389). The methodology developed in these two references is based on condensation between a trinosyl derivative and a diol using a Mitsunobu reaction. However, this method has the drawback of generating a large amount of byproducts that are not always easy to separate from the reaction medium, but above all does not allow the synthesis of azamacrocycles of functionalized 147TACN type as described in the Honiven article. Another strategy under less mild conditions was published by the group of Wu et al. (Synthetic Communications, 34 (2004) 845-851, Synthetic Communications 25 (1995) 1427-1437, Chinese Journal of Chemistry, 16 (1998) 538-541) for obtaining azamacrocycles by condensing a tritosyl derivative with the corresponding diol, in yields in the region of 50%. A major drawback of this second methodology lies in the deprotection of the tosyl groups, which is generally performed under very harsh conditions (100° C., hydrobromic acid, in 33% acetic acid, or at 100° C. in 96% concentrated sulfuric acid).

The complexing agents in which the group -LG is linked to the macrocycle were thus prepared here according to a strategy based on the condensation of a trinosyl derivative with a dibromo derivative using cesium carbonate as base in acetonitrile. The experimental conditions used are similar to those described by Fukuyama et al. (Tetrahedron, 58 (2002) 6267-6276) and are described in SCHEME 4 and the experimental section.

Synthesis of the Chromophores

The chromophores may be manufactured according to an approach as presented in scheme A, and in which the groups $R_1$ and $R_2$ will optionally be protected, depending on their nature, in particular if they are carboxylate or phosphate groups or reactive groups.

This approach was employed for the synthesis of chromophores similar to those which may be used for the preparation of the complexing agents according to the invention, for instance by:

Picot et al. (Inorganic Chemistry 46 (2007), 2659-2665): phenylethynylpyridine chromophore, hexyloxy group on the phenyl group;

Picot et al. (Journal of American Chemical Society 130 (2008) 1532-1533): phenylethynylpyridine chromophore bearing a tris(triethylene glycol)phenyl group ensuring the solubility of the compounds; and D'Aléo et al. (Sensitization of Eu(III) luminescence by donor-phenylethynyl-functionalized DTPA and DO3A macrocycles, C. R. Chimie 2010): phenylethynylpyridine bearing an OPeg group.

The preparation of the reagents required for this synthesis falls within the general knowledge of a person skilled in the art, when these reagents are not commercially available.

Synthesis of the substituted alkynes is described in SCHEMES 1 and 13, and also in the experimental section.

The synthesis of the "carboxylate" chromophores is described in SCHEME 2 and in the experimental section.

The synthesis of the phosphinate" chromophores is described in SCHEME 3 and in the experimental section.

Grafting of the Chromophores onto the Macrocycle

The synthesis of the complexing agents of formula (I) not comprising a reactive group -L-G may be performed by alkylation of a trinitrogenous macrocycle with a derivative of the desired chromophore (Scheme B) comprising a liberable group, such as a mesylate (—OMs), triflate (—OTf) or tosylate (—OTs) group, or alternatively a chlorine, bromine or iodine atom. It may be necessary to protect the groups $R_1$ that may react during the alkylation or that may pose solubility or even polarity problems. For example, when $R_1$ is a carboxylate or phosphinate group, corresponding esterified derivatives may be used.

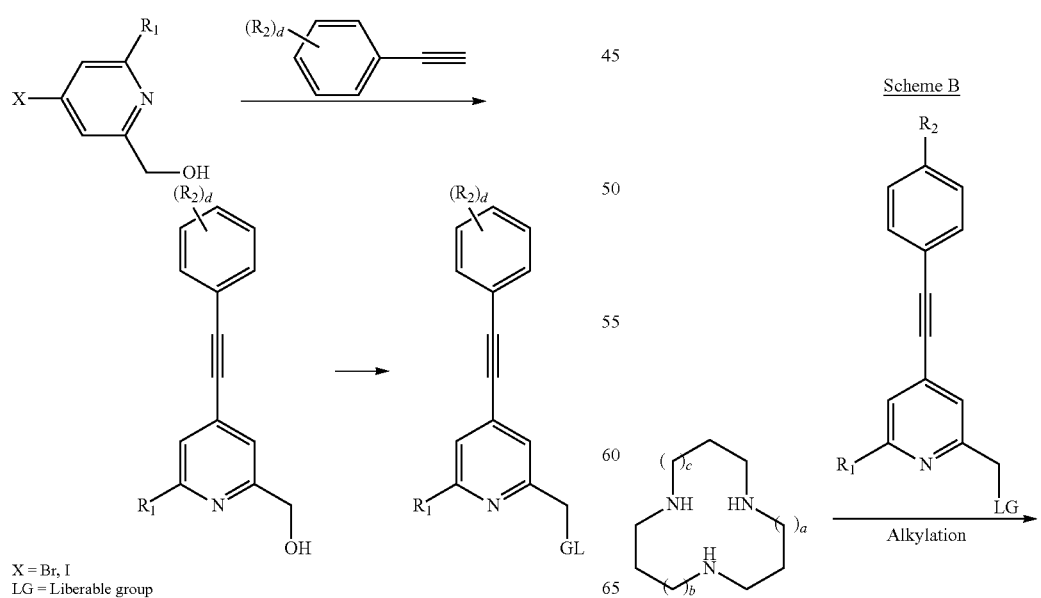

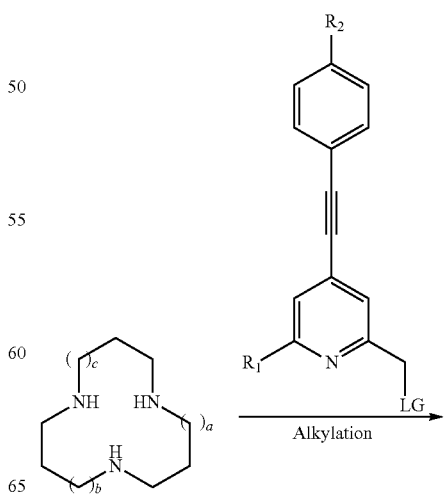

-continued

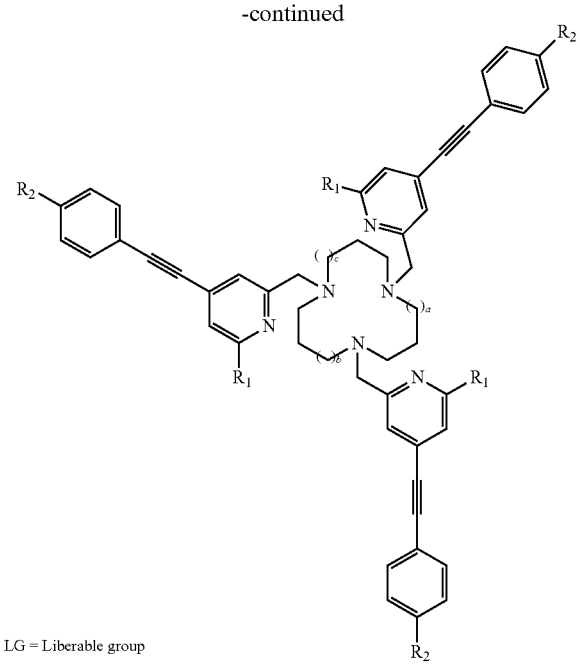

LG = Liberable group

This synthesis is described in greater detail in SCHEME 5 and the experimental section.

The same approach is used when the group -L-G is directly linked to the macrocycle, for example for the complexing agents of formula (I) in which one of the groups $R_3$, $R_4$ or $R_5$ is a group -L-G.

The preparation of complexes in which one of the chromophores comprises a group -L-G may be performed in the same manner, by alkylation of a trinitrogenous macrocycle comprising a protected amine function, prepared, for example, according to a process such as that described above. Once the two chromophores have been grafted onto the macrocycle, the third chromophore bearing the group -L-G (included in the group $R_2$) may in turn be grafted after deprotection of the protected amine (Scheme C).

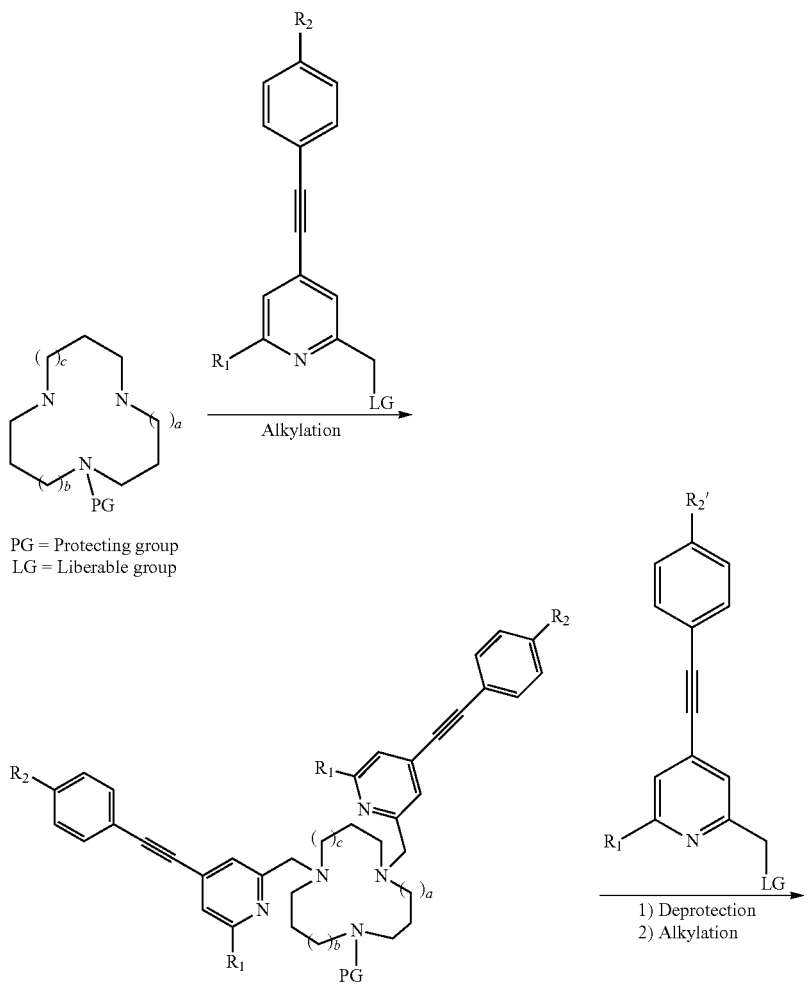

-continued

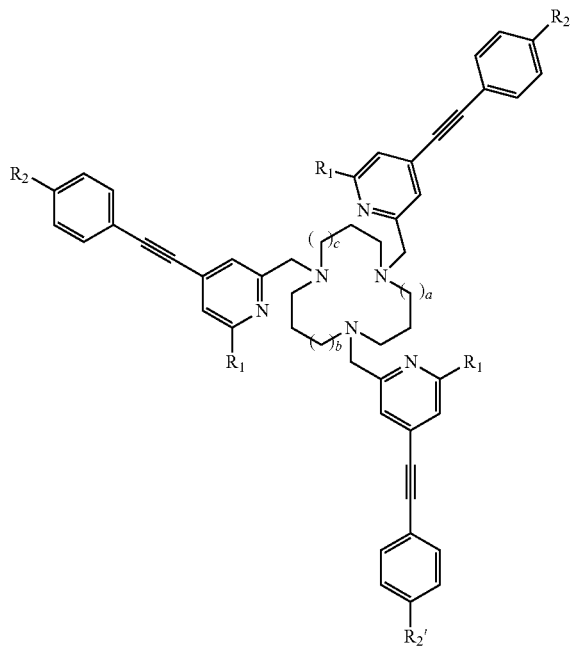

(R'$_2$ is as defined for R$_2$ above).

This synthesis is described in greater detail in SCHEMES 6, 7, 8 and 9 and the experimental section.

A reverse strategy may be envisaged, in which a chromophore comprising a masked reactive group L-G is first introduced onto a diprotected azamacrocycle, using an alkylation reaction. The two protecting groups of the macrocycle orthogonal to the group protecting the reactive function L-G are removed and the other two chromophores are then introduced by simple alkylation, leading to the backbone of the complexing agent (Scheme D).

Scheme D

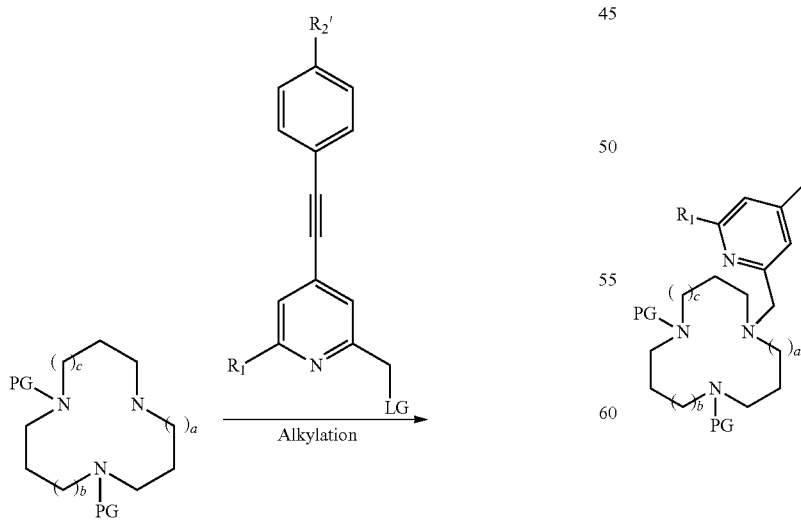

PG = Protecting group
LG = Liberable group

-continued

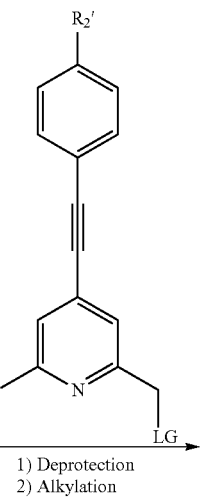

1) Deprotection
2) Alkylation

-continued

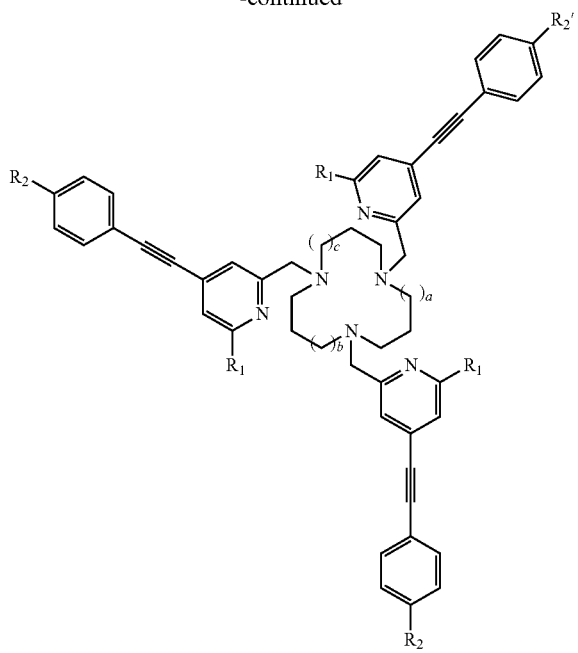

(R'₂ is as defined for R₂ above).

The synthesis of the compounds according to the invention is detailed in precise manner in the following experimental section.

ABBREVIATIONS USED

Figure 1:
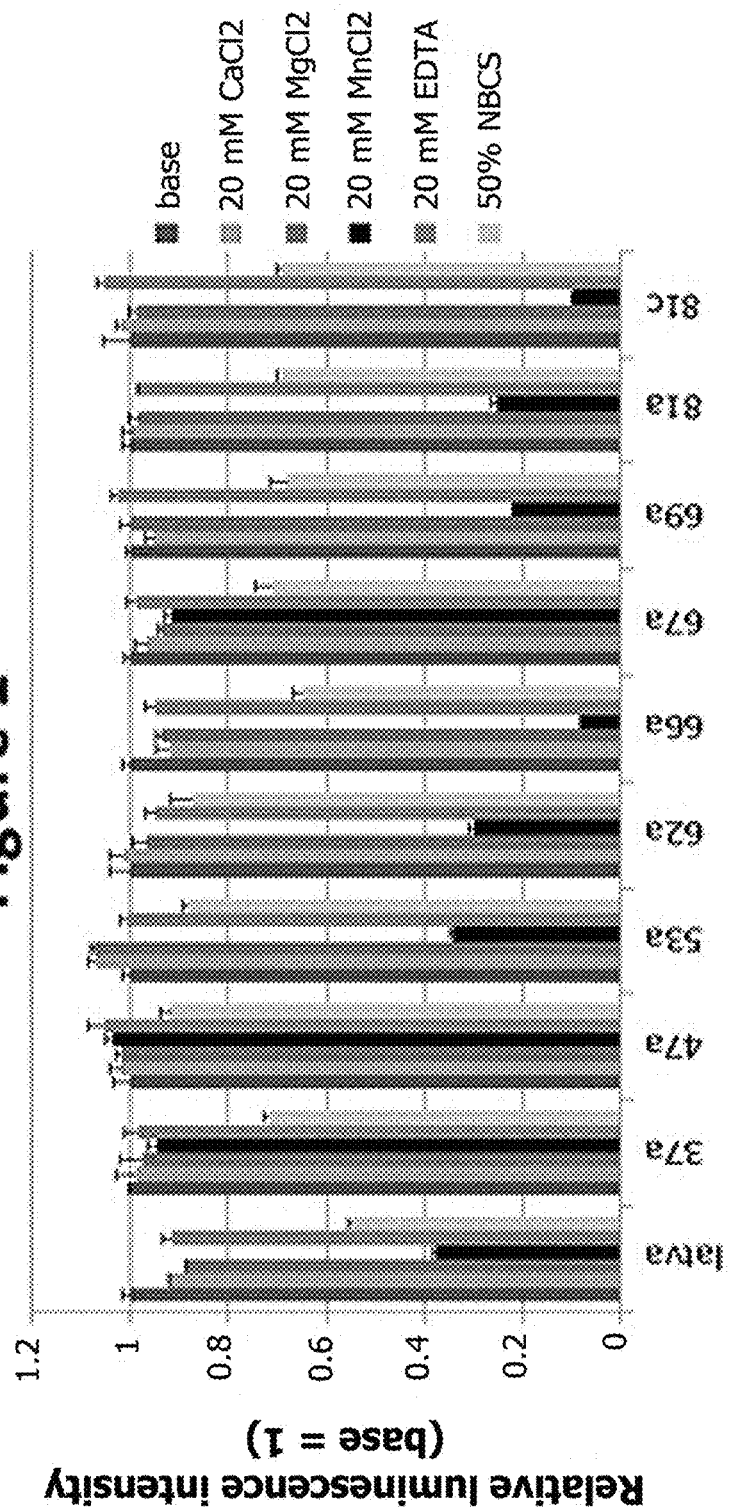
FIG. 1 shows the luminescence of the compounds of the invention in the presence of divalent cations or EDTA.

Ms: Mesyl
Boc: tert-Butyloxycarbonyl
PEG: polyethylene glycol
NHS: N-hydroxysuccinimide
NMR: nuclear magnetic resonance
TLC: thin-layer chromatography
DMF: dimethylformamide
THF: tetrahydrofuran
DCM: dichloromethane
HPLC: high-performance liquid chromatography
HRMS: high-resolution mass spectroscopy
TEA/Et₃N: triethylamine
DIPEA: diisopropylethylamine
NBS: N-bromosuccinimide
NIS: N-iodosuccinimide
TsCl: tosyl chloride
MeCN: acetonitrile
MeOH: methanol
MS: mass spectrometry
ESI: electrospray ionization
m-CPBA: meta-chloroperbenzoic acid
EtOH: ethanol
Moz-ON: ((2-(4-methoxybenzyloxycarbonyloxy imino)-2-phenylacetonitrile)
Boc-OSu: N-(tert-butoxycarbonyloxy)succinimide
TFA: trifluoroacetic acid
Ph: phenyl
TMS=trimethylsilyl
TSTU: O—(N-Succinimidyl)-1,1,3,3-tetramethyluronium tetrafluoroborate
DCC: dicyclohexylurea
m.p.: melting point
δ: chemical shift
ppm: parts per million
Hz: Hertz
min: minute
h: hour
cAMP: cyclic adenosyl monophosphate
Mops: 3-(N-morpholino)propanesulfonic acid
HTRF: Homogeneous Time-Resolved Fluorescence

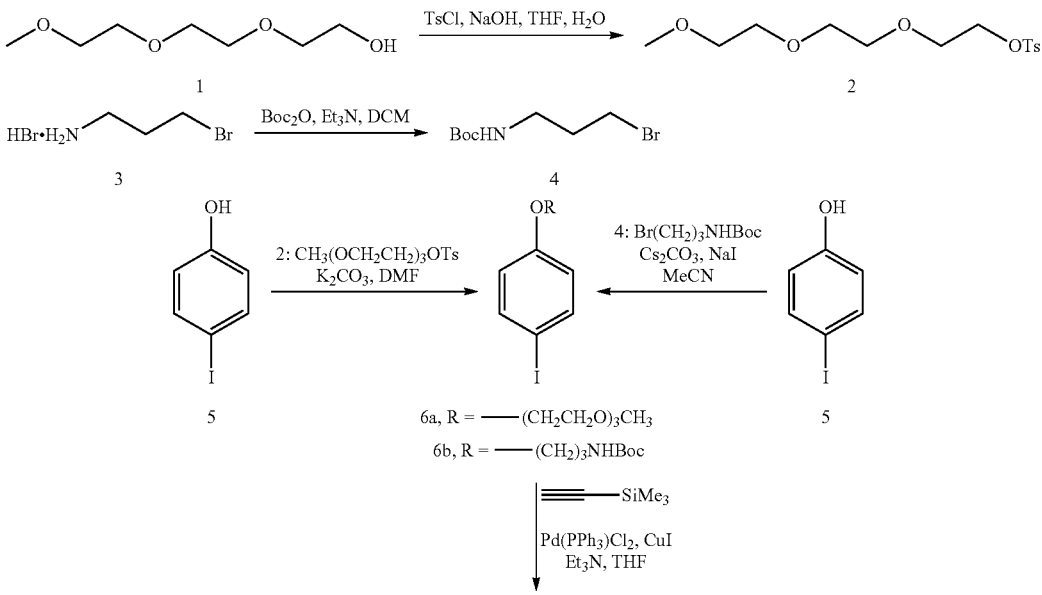

SCHEME 1: SYNTHESIS OF THE SUBSTITUTED ALKYNES

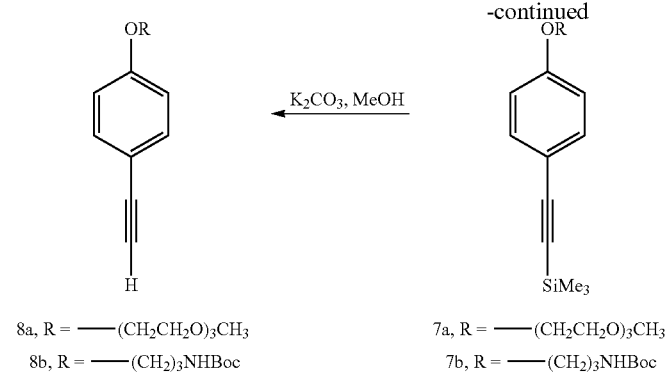

8a, R = —(CH₂CH₂O)₃CH₃
8b, R = —(CH₂)₃NHBoc

7a, R = —(CH₂CH₂O)₃CH₃
7b, R = —(CH₂)₃NHBoc

The general strategy for synthesizing the chromophores involves a Sonogashira coupling which has been widely described in the literature (Sonogashira et al. Tetrahedron Letters, 50 (1975) 4467-4470, Rossi et al. Organic Preparation and Procedure International 27 (1995) 129-160). This reaction makes it possible to couple a true alkyne with an aromatic halide (preferably an iodo or bromo derivative) or a tosyl. The true alkynes (8a and 8b) are not commercially available. They were prepared according to the synthesis described in scheme 1 and detailed in the experimental section. Thus, the polyethylene glycol derivative 1 was activated in the form of the tosyl compound. Protection of the amine 3 with a Boc protecting group was necessary to avoid polyalkylation. The two alkylations of the iodophenol led to the two phenol ethers 6a and 6b in suitable yields of 51% and 75%, respectively. The Sonogashira couplings using trimethylsilylacetylene followed by deprotection of the TMS group led to the two desired true alkynes 8a and 8b.

SCHEME 2: SYNTHESIS OF THE "CARBOXYLATE" CHROMOPHORES

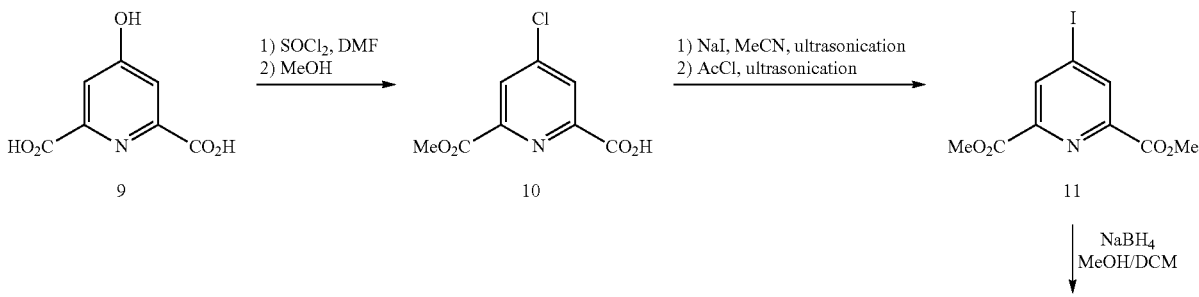

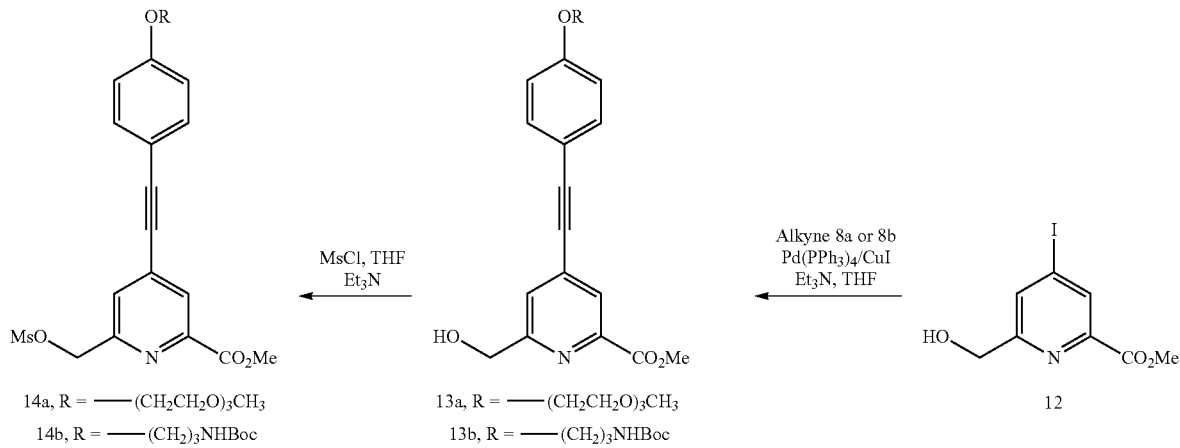

14a, R = —(CH₂CH₂O)₃CH₃
14b, R = —(CH₂)₃NHBoc

13a, R = —(CH₂CH₂O)₃CH₃
13b, R = —(CH₂)₃NHBoc

The synthesis of the "carboxylate" chromophores is described in scheme 2. Chelidamic acid 9 is converted into the chloro diester 10 as described by Maury et al. (Inorganic Chemistry 50 (2011) 4987-4999). The chlorine-iodine exchange is performed in the presence of sodium iodide with ultrasonication to give compound 11. The key step of this synthesis consists in selectively reducing the diester 11 in the presence of sodium borohydride at 0° C. to obtain the monoalcohol monoester in a yield of 60%. Finally, the backbone of the chromophore is obtained by using a second Sonogashira reaction, thus leading to the compounds 13a and 13b. Finally, activation of the alcohols was performed via a mesylation reaction.

SCHEME 3: SYNTHESIS OF THE "PHOSPHINATE" CHROMOPHORES

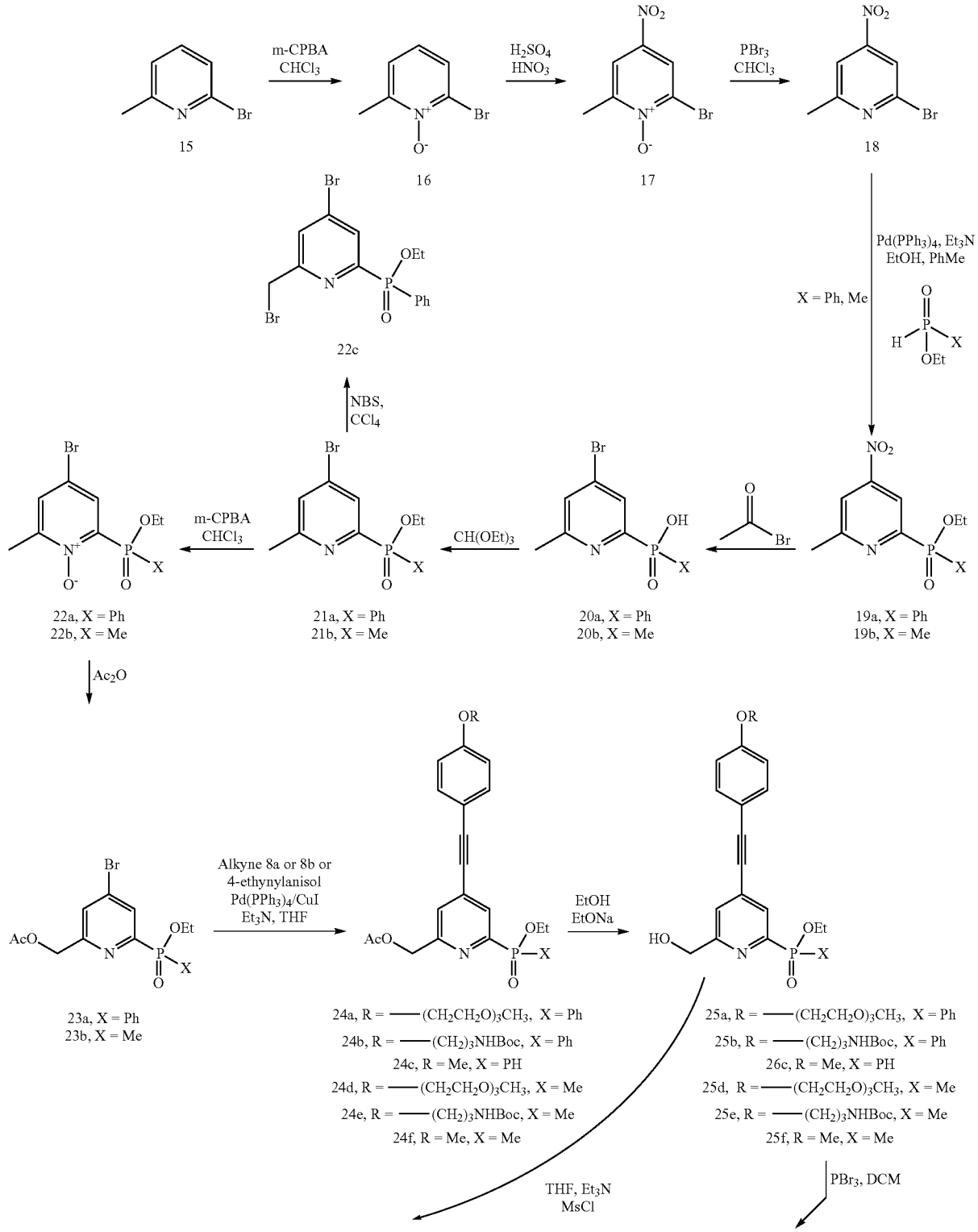

-continued

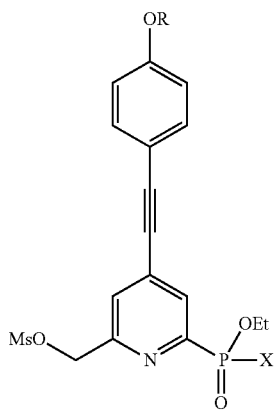

26g, R = ——(CH₂CH₂O)₃CH₃, X = Ph
26h, R = ——(CH₂)₃NHBoc, X = Ph
26i, R = Me, X = PH
26j, R = ——(CH₂CH₂O)₃CH₃, X = Me
26k, R = ——(CH₂)₃NHBoc, X = Me
26l, R = Me, X = Me

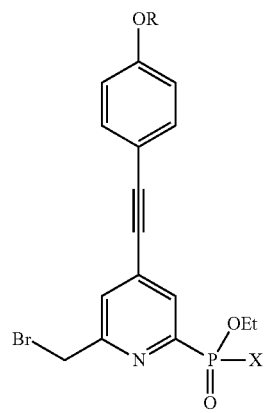

26a, R = ——(CH₂CH₂O)₃CH₃, X = Ph
26b, R = ——(CH₂)₃NHBoc, X = Ph
26c, R = Me, X = PH
26d, R = ——(CH₂CH₂O)₃CH₃, X = Me
26e, R = ——(CH₂)₃NHBoc, X = Me
26f, R = Me, X = Me

The preparation of the "phosphinate" chromophores is described in scheme 3. The goal of the synthesis consists in providing an orthogonally trisubstituted pyridine derivative. Thus, the commercially available 2-bromo-6-methylpyridine is oxidized to the N-oxide analog 16 via simple oxidation in the presence of meta-chloroperbenzoic acid (m-CPBA). Activation of this nitrogenous heterocycle enables easy introduction of the nitro group into position 4, corresponding to the third functional group. The N-oxide is then removed using phosphorus tribromide, leading to the free pyridyl derivative. Introduction of the phosphinate group was performed using a palladium coupling in the presence of commercial phenylphosphinic acid. As regards pyridine methylphosphinate, it is obtained by coupling the ethyl methyl phosphinate derivative, which is itself obtained by hydrolysis of diethyl methyl phosphonite using 1 equivalent of water. The development of these coupling reactions proved to be particularly difficult and finally made it possible to obtain the desired compounds 19a and 19b using microwaves as an energy source, but also thermally. The rest of the description of the synthesis was performed, for example, on the phenyl phosphinate series, but the results are extrapolable to the methyl phosphinates since these two types of compound have identical reactivities. The substitution of the nitro group with a bromine atom was performed in the presence of acetyl bromide. Although this reagent is efficient in this reaction, it gives rise to the formation of hydrobromic acid, which hydrolyzes the phosphinate group. This is reintroduced immediately afterwards by using ethyl orthoformate. The functionalization of the methyl in position 6 of the pyridine is performed using a rearrangement described by Ginsburg et al. (Journal American Chemical Society 79 (1957) 481-485). The pyridine is oxidized a second time using the same conditions described previously. This N-oxide function is sufficiently nucleophilic to react with acetic anhydride, which intermediately undergoes a rearrangement, thus making it possible to insert an acetate group into position 6 leading to the key intermediates for the synthesis 23a and 23b. The backbone of the phosphinate chromophore is developed using the Sonogashira reaction in the presence of the true alkynes described previously. The ester (acetate) is hydrolyzed to the corresponding alcohol, which is converted into the bromo derivative leading to the activated phosphinate chromophores 26a-f. Alternatively, it is also possible to prepare the corresponding mesyl derivatives as described previously for the "carboxylate" chromophores, thus leading to the derivatives 26g-l.

SCHEME 4: SYNTHESIS OF THE MONOBoc MACROCYCLES AND DISSYMMETRIC AZAMACROCYCLES

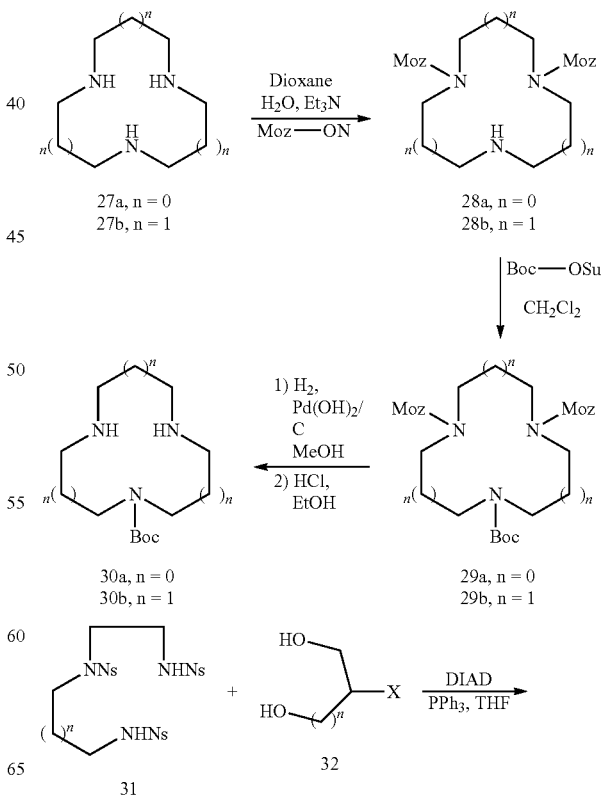

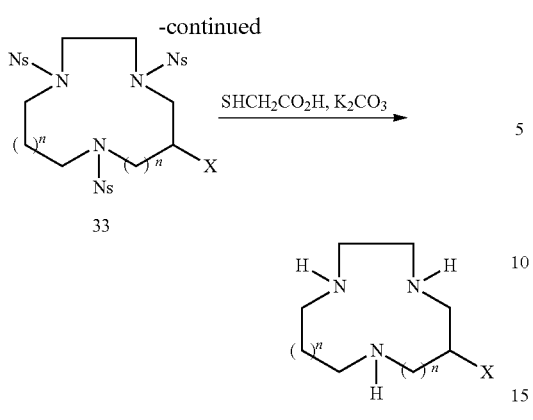

X = H, OH
n = 0, 1

As regards the dissymmetric azamacrocycles (series 34) optionally bearing a functional group X, they were prepared by condensation of the diol derivative with a dinosyl compound 31 using the Mitsunobu conditions. The deprotection of the nosyl groups is performed conventionally in the presence of thioglycolic acid and potassium carbonate. This reaction sequence makes it possible to obtain, for example, all the substituted or unsubstituted variants of the azamacrocycles (147TACN, 159TACD, 148TACD and 148TACU).

SCHEME 5: SYNTHESIS OF THE NON-FUNCTIONALIZED LANTHANIDE COMPLEXES OF "PHOSPHINATE" TYPE

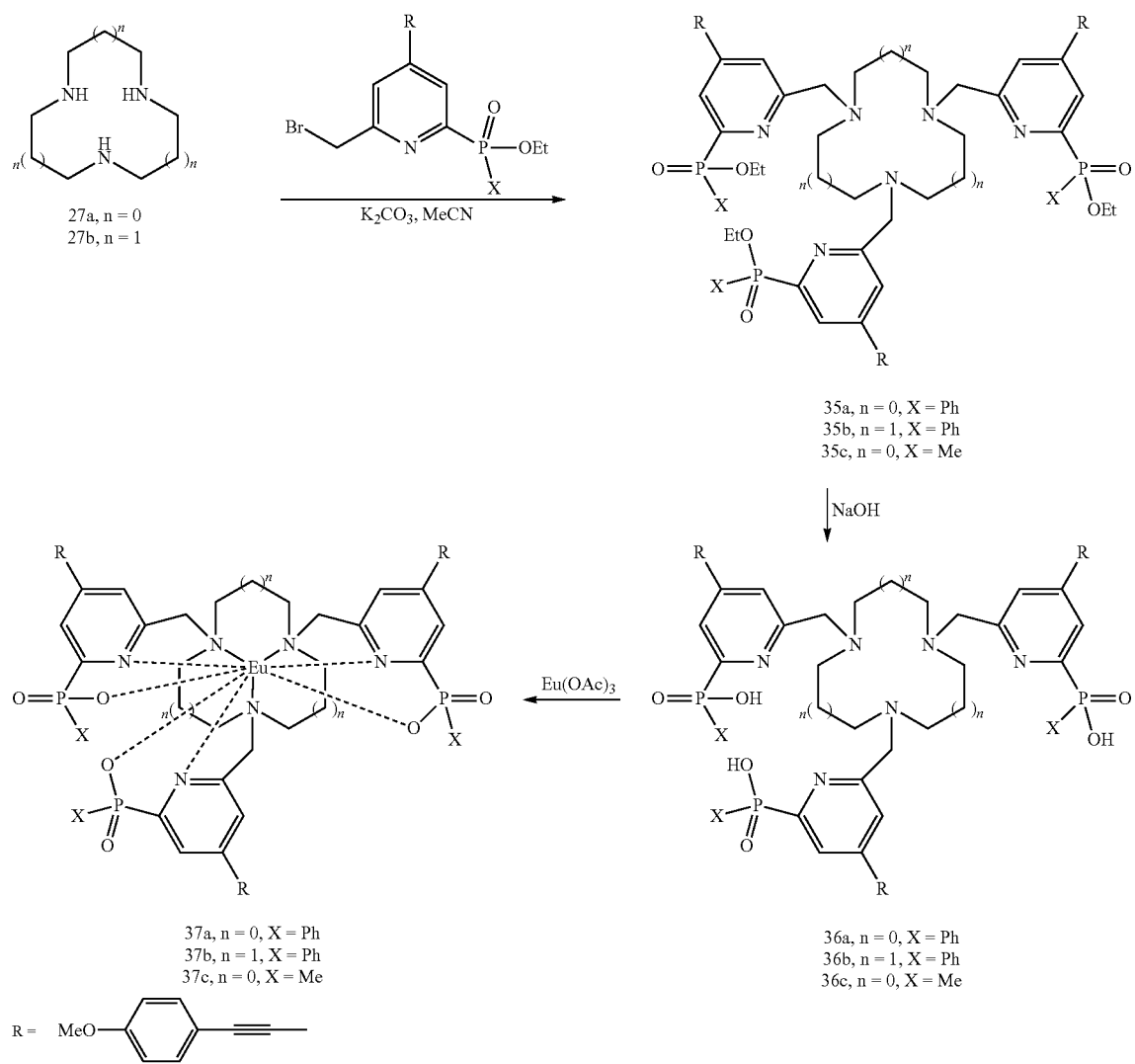

A first example of non-functionalized phosphinate complex is described in scheme 5. The azamacrocycle is condensed onto the bromo phosphinate chromophore in the presence of potassium carbonate. The phosphinate esters are hydrolyzed with potassium or lithium hydroxide to give the ligands, which are then used to form the europium complexes 37a-c.

The europium complexes are prepared according to schemes 6 and 7. Starting with the mono-substituted macrocycles 147TACN and 159TACD, two "carboxylate or phosphinate "OPEG" chromophores" are condensed, leading to the derivatives 42a-b or 47a-c. In terms of yield, comparable results were obtained with the bromo or mesyl phosphinate chromophores. The Boc protecting group is deprotected in SCHEME 6: SYNTHESIS OF THE FUNCTIONALIZED LANTHANIDE COMPLEXES OF "CARBOXYLATE" TYPE

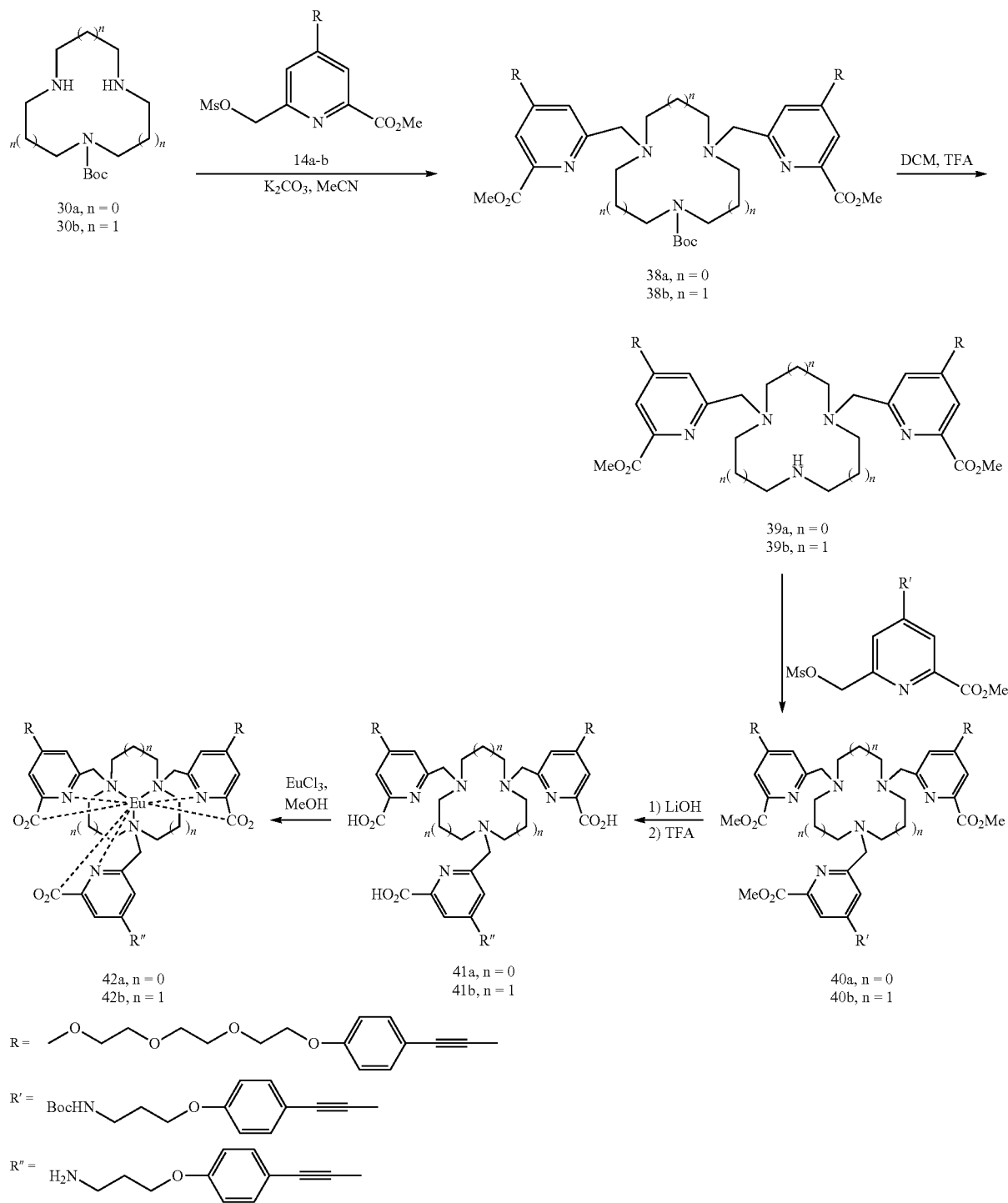

the presence of trifluoroacetic acid, followed by alkylation of the third chromophore comprising a masked $NH_2$ group, which is useful for conjugation to a biomolecule. The three ester functions (carboxylate or phosphinate) are then hydro- lyzed and the Boc group is removed in acidic medium. The formation of the lanthanide complex is performed by reacting the ligands 41 and 46 with the corresponding lanthanide salts, in the present case europium chloride or acetate.

SCHEME 7: SYNTHESIS OF THE FUNCTIONALIZED LANTHANIDE COMPLEXES OF "PHOSPHINATE" TYPE

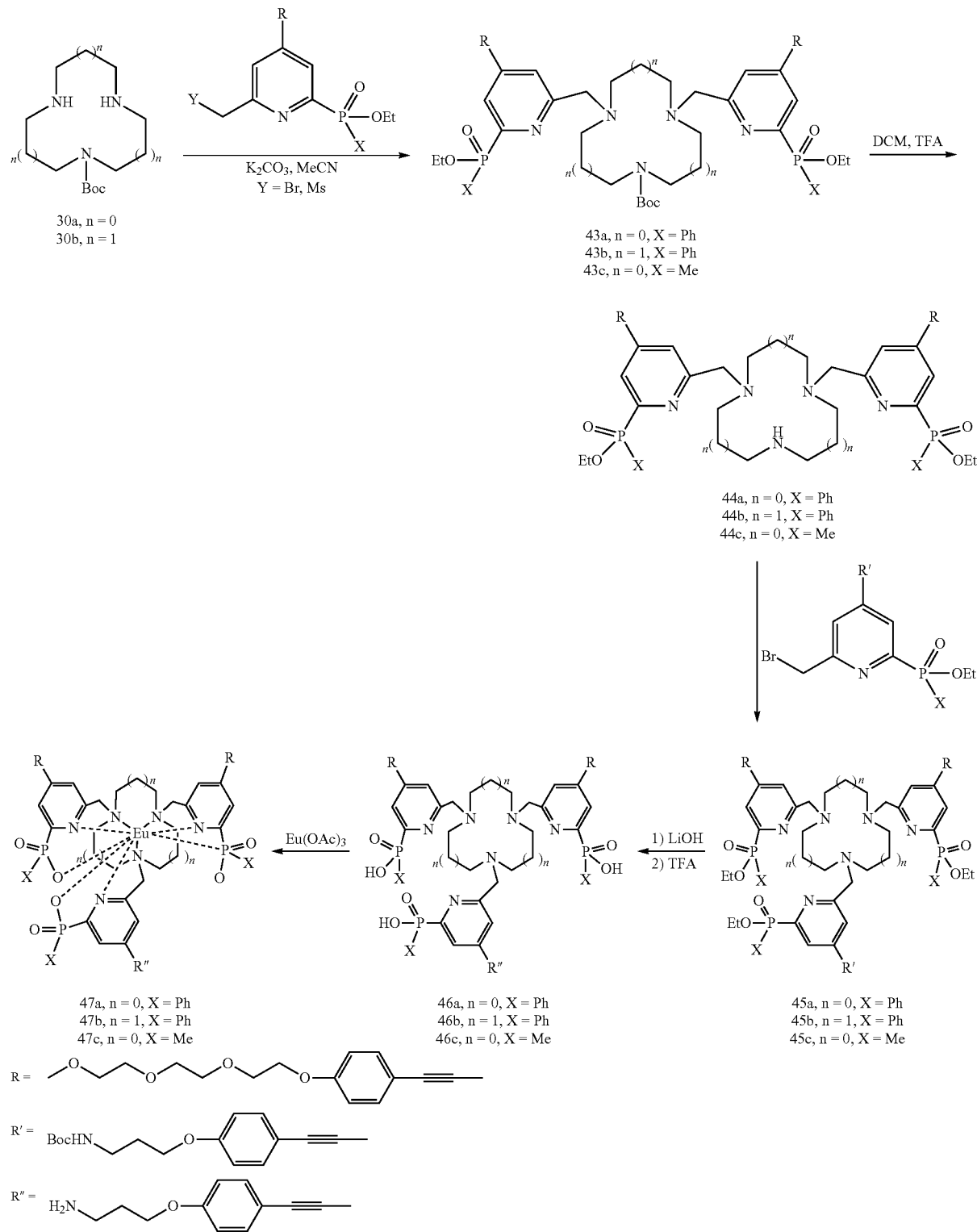

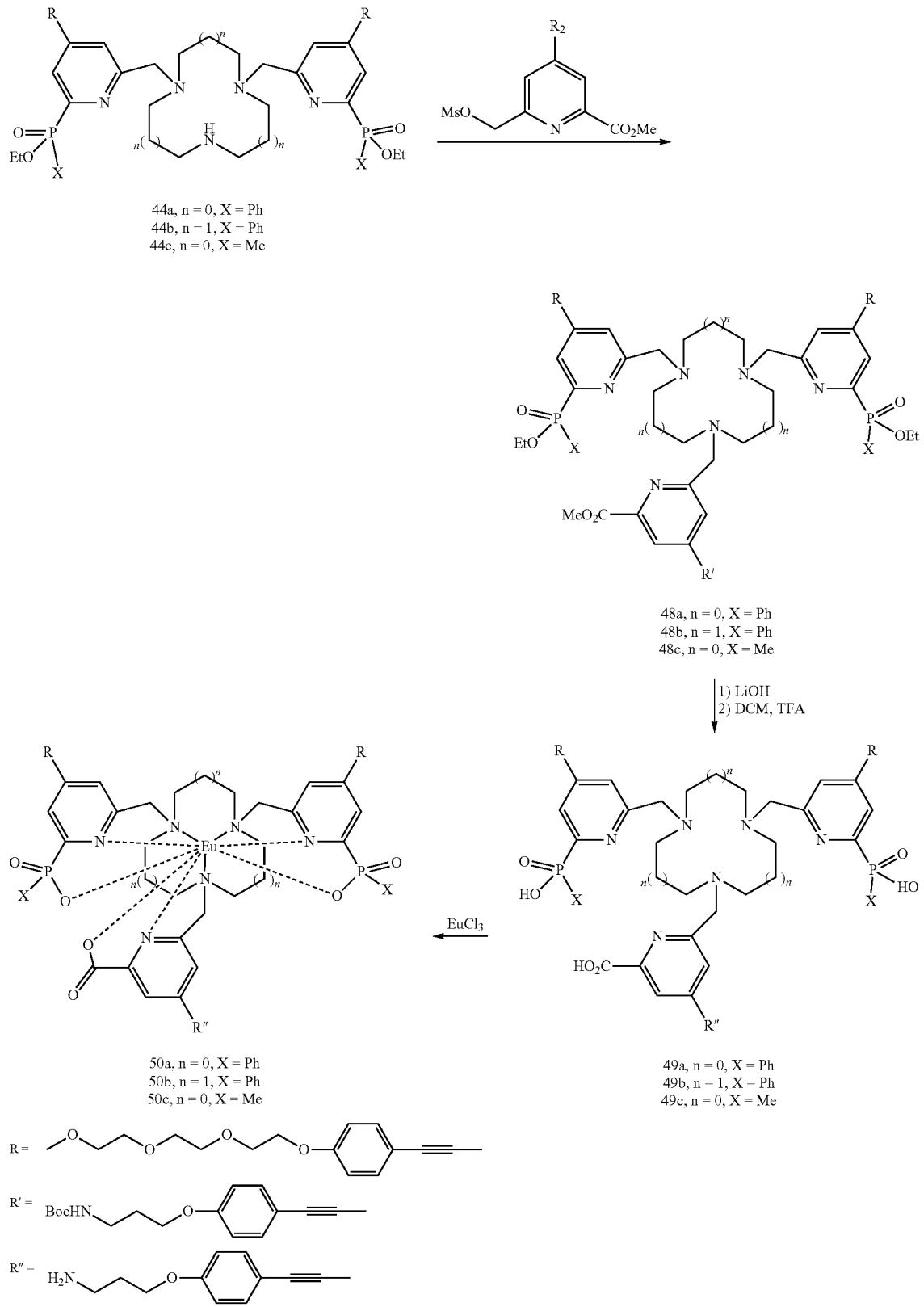

SCHEME 9: SYNTHESIS OF THE HYBRID FUNCTIONALIZED LANTHANIDE COMPLEXES OF "BICARBOXYLATE MONOPHOSPHINATE" TYPE
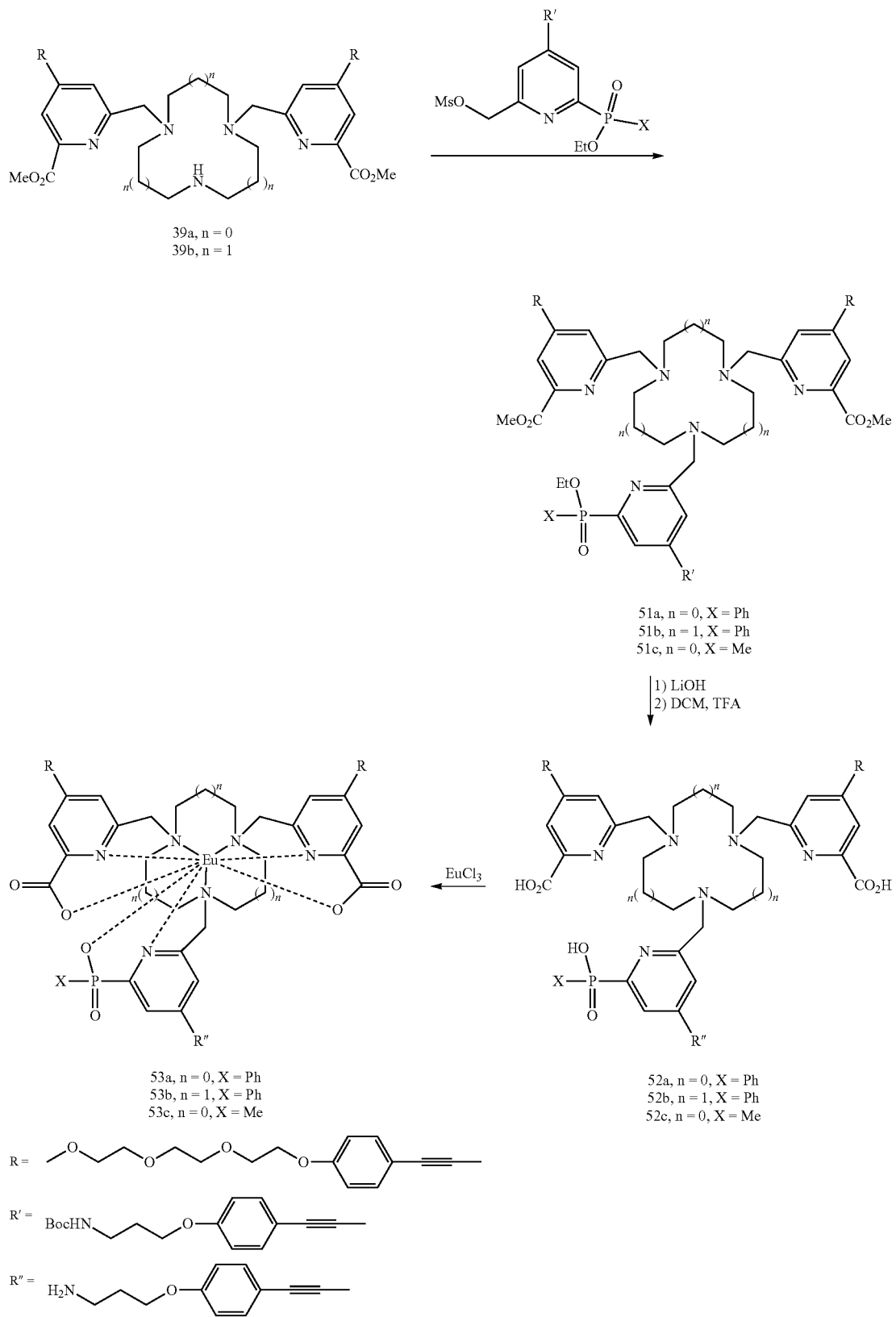

The methodology for preparing the hybrid complexes is described on the two schemes 9 and 10. It consists in using synthons prepared previously in the context of the synthesis of the phosphinate or carboxylate complexes.

Starting with the dialkyl derivatives (dicarboxylate-OPEG or diphosphinate-OPEG) the mesyl phosphinate derivatives (for the dicarboxylates) or the mesyl carboxylate derivatives (for the diphosphinates) are condensed. These reactions lead to the hybrid ligands, which are then hydrolyzed and complexed with the rare-earth metal and in particular with europium using europium chloride or acetate.

SCHEME 10: FUNCTIONALIZATION OF THE LANTHANIDE COMPLEXES FOR A BIOCONJUGATION REACTION

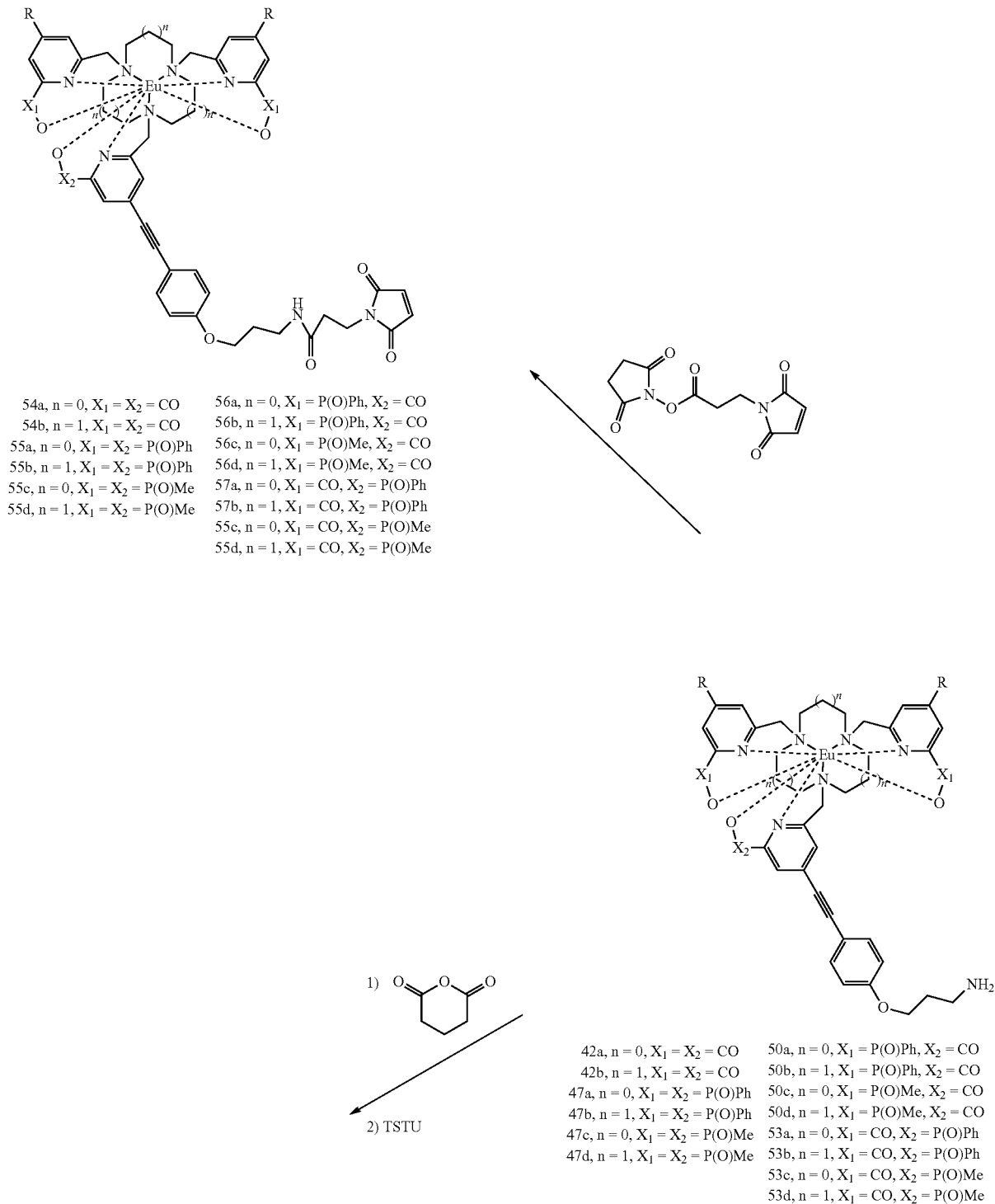

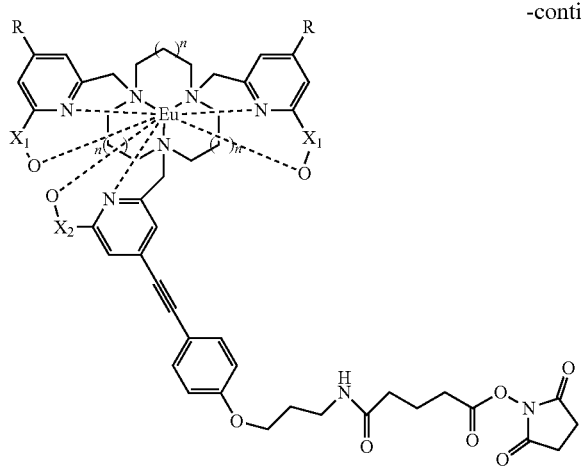

58a, n = 0, X₁ = X₂ = CO  
58b, n = 1, X₁ = X₂ = CO  
59a, n = 0, X₁ = X₂ = P(O)Ph  
59b, n = 1, X₁ = X₂ = P(O)Ph  
59c, n = 0, X₁ = X₂ = P(O)Me  
59d, n = 1, X₁ = X₂ = P(O)Me 60a, n = 0, X₁ = P(O)Ph, X₂ = CO  
60b, n = 1, X₁ = P(O)Ph, X₂ = CO  
60c, n = 0, X₁ = P(O)Me, X₂ = CO  
60d, n = 1, X₁ = P(O)Me, X₂ = CO 61a, n = 0, X₁ = CO, X₂ = P(O)Ph  
61b, n = 1, X₁ = CO, X₂ = P(O)Ph  
61c, n = 0, X₁ = CO, X₂ = P(O)Me  
61d, n = 1, X₁ = CO, X₂ = P(O)Me

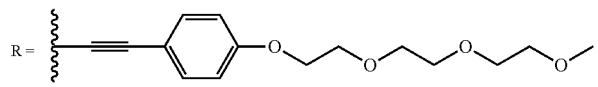

The NH₂-functionalized complex cannot be used in the present state to be bioconjugated to a biomolecule: proteins, antibodies, peptides, sugars, etc. To perform these bioconjugations, it is necessary to convert this NH₂ group into a biocompatible functional group. The methodology is described hereinbelow:

For the maleimide complexes, they are prepared directly using a difunctional commercial reagent: N-[β-maleimidopropyloxy]succinimidyl, which leads to the desired functionalization. As regards the production of the complexes functionalized in NHS ester form, it is necessary to convert the amine function beforehand into a carboxylic acid derivative (condensation of glutaric anhydride onto the amino group), and then to activate this function in NHS ester form using either TSTU or the standard conditions DCC, NHS.

SCHEME 11: COUPLING OF THE LANTHANIDE COMPLEXES ONTO A BENZYLGUANINE DERIVATIVE

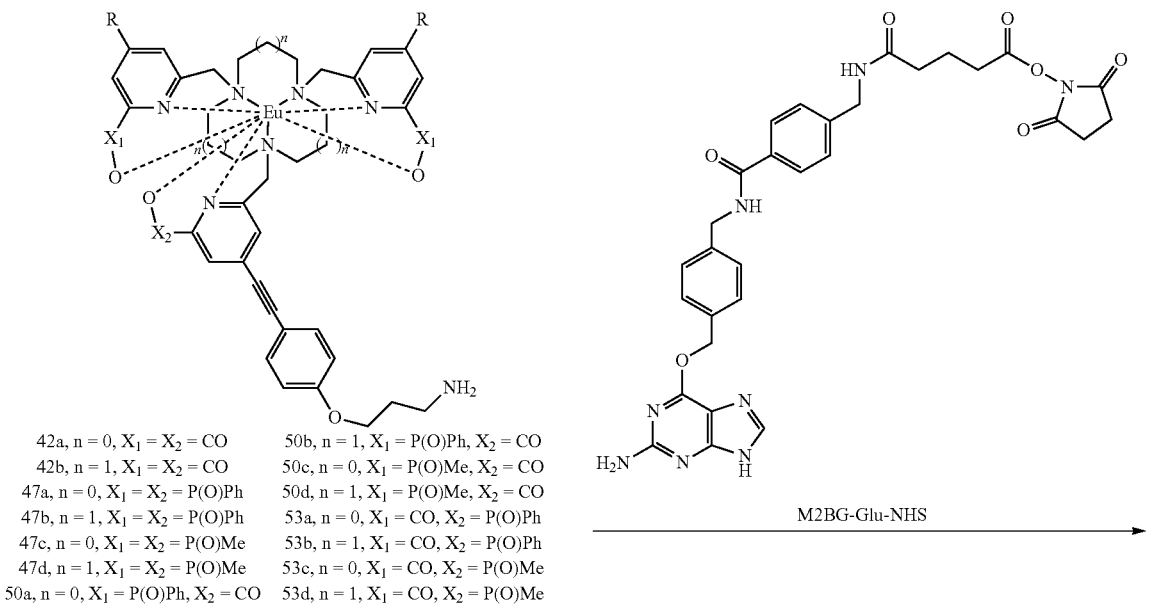

42a, n = 0, X₁ = X₂ = CO  
42b, n = 1, X₁ = X₂ = CO  
47a, n = 0, X₁ = X₂ = P(O)Ph  
47b, n = 1, X₁ = X₂ = P(O)Ph  
47c, n = 0, X₁ = X₂ = P(O)Me  
47d, n = 1, X₁ = X₂ = P(O)Me  
50a, n = 0, X₁ = P(O)Ph, X₂ = CO 50b, n = 1, X₁ = P(O)Ph, X₂ = CO  
50c, n = 0, X₁ = P(O)Me, X₂ = CO  
50d, n = 1, X₁ = P(O)Me, X₂ = CO  
53a, n = 0, X₁ = CO, X₂ = P(O)Ph  
53b, n = 1, X₁ = CO, X₂ = P(O)Ph  
53c, n = 0, X₁ = CO, X₂ = P(O)Me  
53d, n = 1, X₁ = CO, X₂ = P(O)Me

M2BG-Glu-NHS

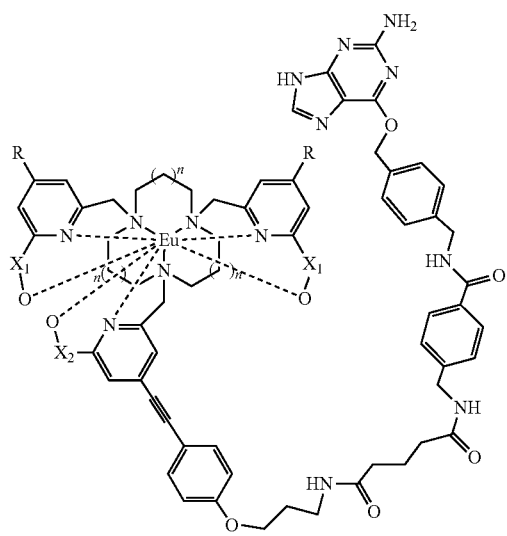

| | | | |
|---|---|---|---|
| 62a, n = 0, X₁ = X₂ = CO | 63c, n = 0, X₁ = X₂ = P(O)Me | 64c, n = 0, X₁ = P(O)Me, X₂ = CO | 65b, n = 1, X₁ = CO, X₂ = P(O)Ph |
| 62b, n = 1, X₁ = X₂ = CO | 63d, n = 1, X₁ = X₂ = P(O)Me | 64d, n = 1, X₁ = P(O)Me, X₂ = CO | 65c, n = 0, X₁ = CO, X₂ = P(O)Me |
| 63a, n = 0, X₁ = X₂ = P(O)Ph | 64a, n = 0, X₁ = P(O)Ph, X₂ = CO | 65a, n = 0, X₁ = CO, X₂ = P(O)Ph | 65d, n = 1, X₁ = CO, X₂ = P(O)Me |
| 63b, n = 1, X₁ = X₂ = P(O)Ph | 64b, n = 1, X₁ = P(O)Ph, X₂ = CO | | |

(Using $X_1$, $X_2$, $n$ subscripts; formulas as shown.)

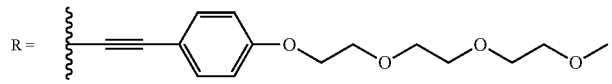

The condensation of the complexes onto the derivative M2BG-Glu-NHS, the synthesis of which is described in patent application WO 2010/034931, leads to the conjugated complexes, which may be used in a Snap protein labeling reaction.

SCHEME 12: COUPLING OF THE LANTHANIDE COMPLEXES ONTO A CYCLIC AMP DERIVATIVE

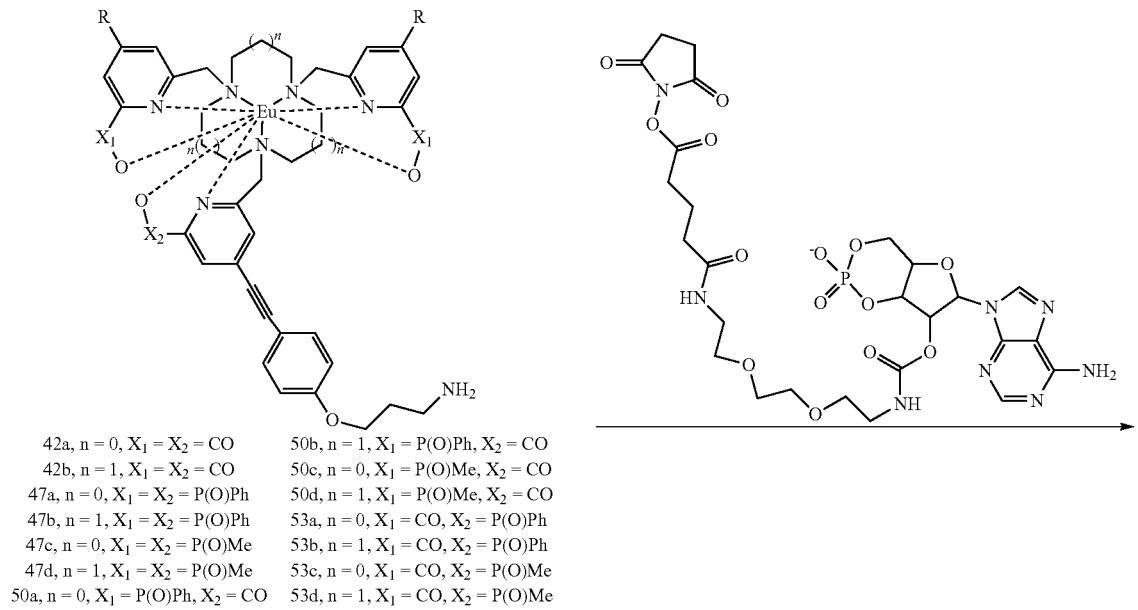

| | |
|---|---|
| 42a, n = 0, X₁ = X₂ = CO | 50b, n = 1, X₁ = P(O)Ph, X₂ = CO |
| 42b, n = 1, X₁ = X₂ = CO | 50c, n = 0, X₁ = P(O)Me, X₂ = CO |
| 47a, n = 0, X₁ = X₂ = P(O)Ph | 50d, n = 1, X₁ = P(O)Me, X₂ = CO |
| 47b, n = 1, X₁ = X₂ = P(O)Ph | 53a, n = 0, X₁ = CO, X₂ = P(O)Ph |
| 47c, n = 0, X₁ = X₂ = P(O)Me | 53b, n = 1, X₁ = CO, X₂ = P(O)Ph |
| 47d, n = 1, X₁ = X₂ = P(O)Me | 53c, n = 0, X₁ = CO, X₂ = P(O)Me |
| 50a, n = 0, X₁ = P(O)Ph, X₂ = CO | 53d, n = 1, X₁ = CO, X₂ = P(O)Me |

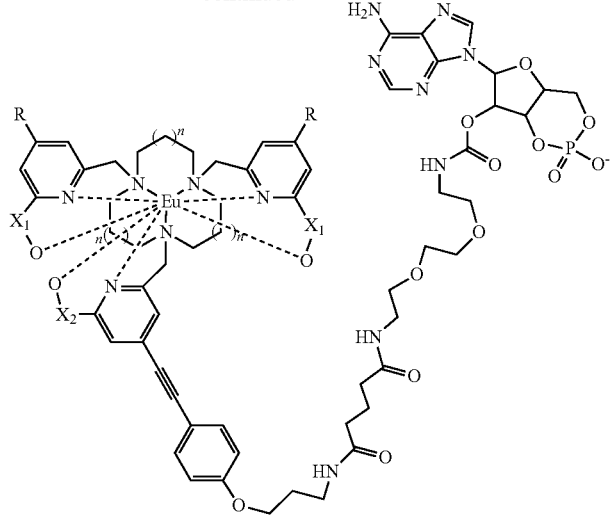

66a, n = 0, X₁ = X₂ = CO
66b, n = 1, X₁ = X₂ = CO
67a, n = 0, X₁ = X₂ = P(O)Ph
67b, n = 1, X₁ = X₂ = P(O)Ph 67c, n = 0, X₁ = X₂ = P(O)Me
67d, n = 1, X₁ = X₂ = P(O)Me
68a, n = 0, X₁ = P(O)Ph, X₂ = CO
68b, n = 1, X₁ = P(O)Ph, X₂ = CO 68c, n = 0, X₁ = P(O)Me, X₂ = CO
68d, n = 1, X₁ = P(O)Me, X₂ = CO
69a, n = 0, X₁ = CO, X₂ = P(O)Ph 69b, n = 1, X₁ = CO, X₂ = P(O)Ph
69c, n = 0, X₁ = CO, X₂ = P(O)Me
69d, n = 1, X₁ = CO, X₂ = P(O)Me

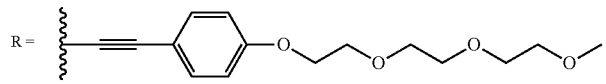

30

The condensation of the complexes onto the cAMP derivative makes it possible to obtain a whole series of complexes conjugated to cAMP. These complexes all have the same photophysical properties and may be used in the HTRF tests developed by Cisbio Bioassays.

SCHEME 13: PREPARATION OF THE ALKYNES

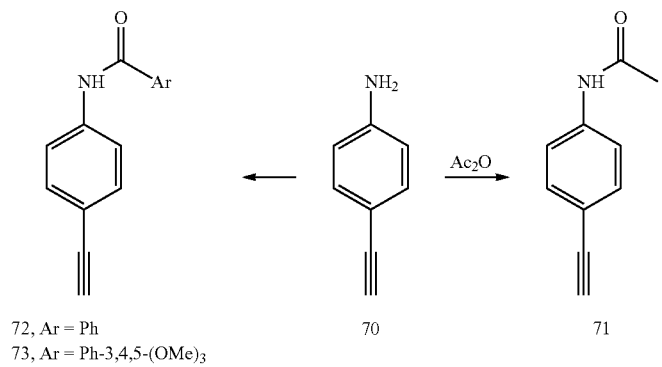

72, Ar = Ph
73, Ar = Ph-3,4,5-(OMe)₃

70

71

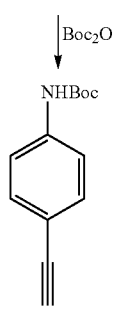

74

Method A

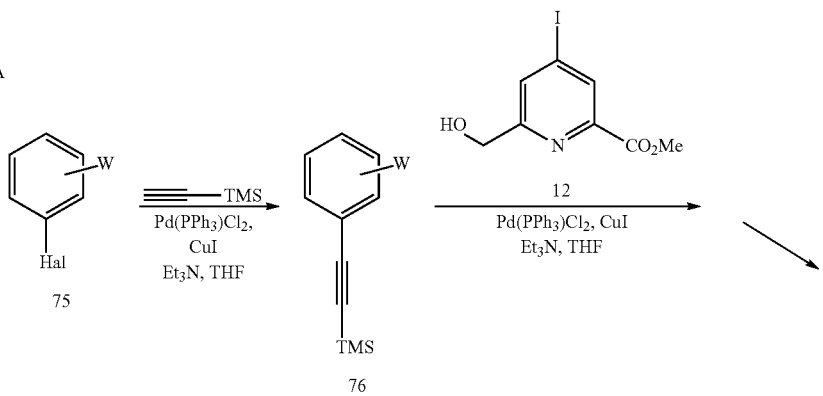

Method B

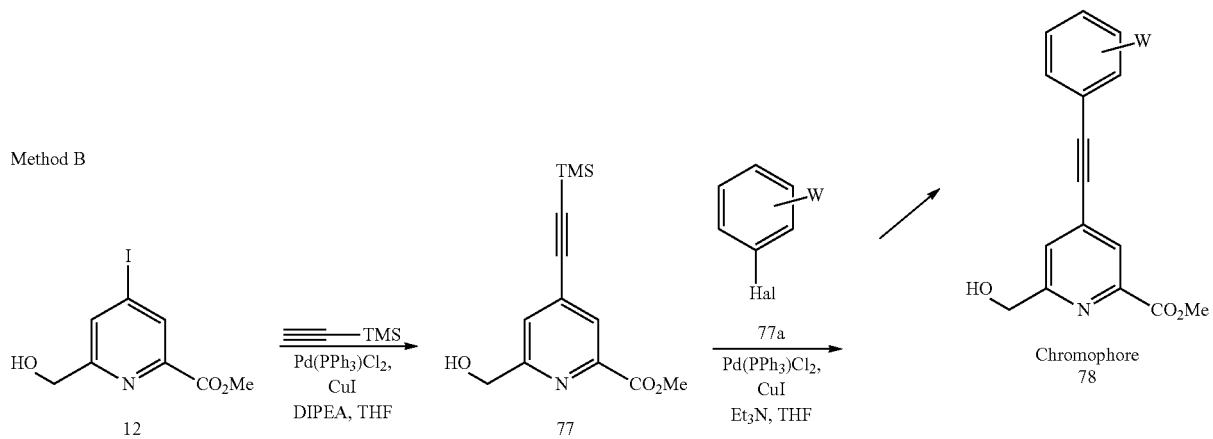

Hal = I or Br

The nature of the group W depends on the chromophore to be synthesized and has no influence on the synthesis of the chromophores.

As regards the acetylated acetylenic derivative 71, it was obtained by simple acetylation reaction in the presence of acetic anhydride using the corresponding commercial precursor.

The chromophores that are not commercially available were prepared simply according to method A or B.

Method A breaks down into three steps: halogenation of the commercial aromatic derivative, followed by a Sonogashira coupling with trimethylsilylacetylene leading to the derivative 76, deprotection of the trimethylsilyl protecting group may be performed in situ or otherwise during the second Sonogashira reaction, which makes it possible to obtain the chromophore 78. According to method B, the reaction sequence is performed in the reverse order, namely: Sonogashira reaction with the iodopyridine derivative 12 leading to the derivative 77, which is deprotected in situ during the second coupling thus leading to the chromophore 78.

SCHEME 14: SYNTHESIS OF THE COMPLEXES COMPRISING VARIOUS DONATING GROUPS

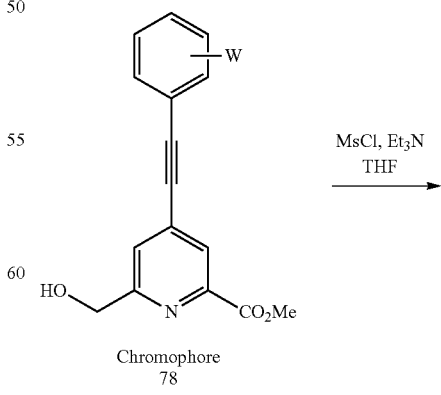

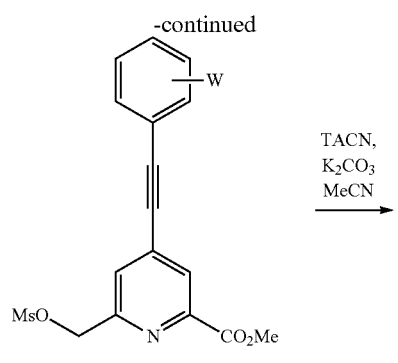

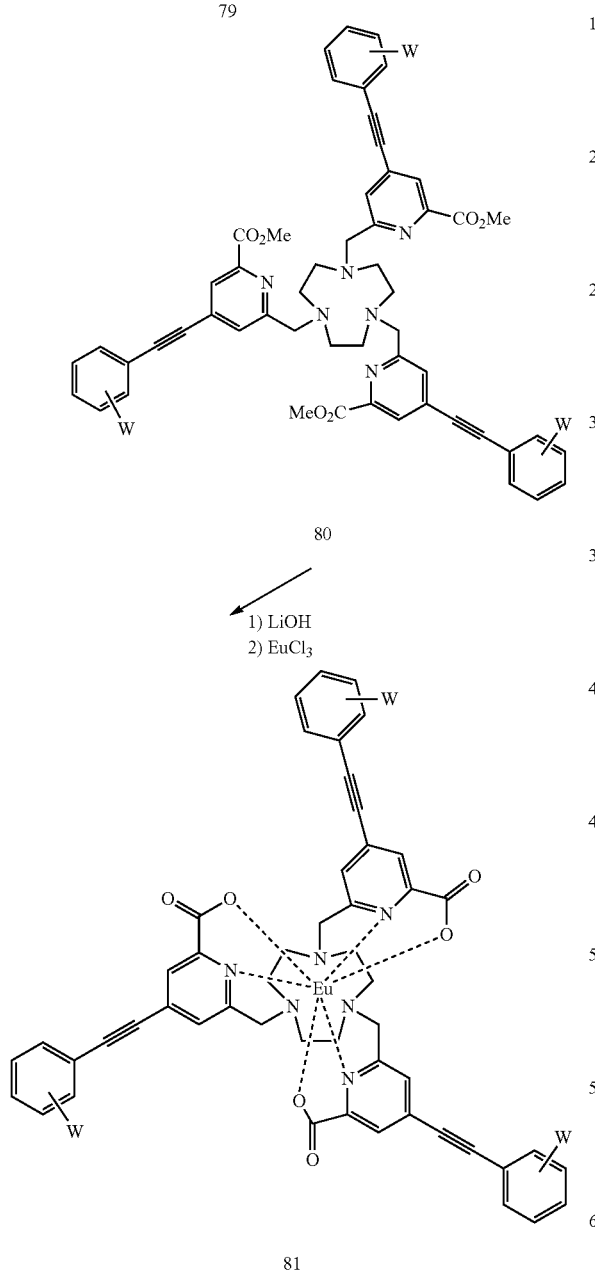

The general methodology for obtaining symmetrical complexes is described in scheme 14: the chromophores are mesylated and then introduced onto the nitrogenous macrocycle (in this case, for example, triazacyclononane). Hydrolysis of the three ester functions to carboxylic acids followed by complexation with europium leads to the corresponding complex. This approach rapidly makes it possible to discriminate a certain number of complexes having the desired photophysical properties and avoids the more fastidious preparation of functionalized dissymmetric complexes. In point of fact, it was determined that the photophysical properties of a symmetrical europium complex (TACN or TACD complex) (three identical chromophores) were the same as those for a dissymmetric europium complex (two identical chromophores and one chromophore bearing a group -LG allowing conjugation with a biomolecule).

EXPERIMENTAL SECTION

General Information
Chromatography

The thin-layer chromatographies were performed on Merck 60 $F_{254}$ silica gel plates on a sheet of aluminum or on Merck 60 $F_{254}$ neutral aluminum oxide plates (type E) on a sheet of aluminum.

The analytical and preparative high-performance liquid chromatographies (HPLC) were performed on two machines:
  Analytical HPLC: ThermoScientific, P4000 quaternary pump, UV 1000 detector with a deuterium lamp (190-350 nm), Waters XBridge C18, 3.5 µm, 4.6×100 mm analytical column.
  Preparative HPLC: Shimadzu, 2 LC-8A pumps, Varian ProStar UV diode array detector, Waters XBridge prep. C18, 5 µm: 19×100 mm or 50×150 mm preparative column.

The chromatographies on a column of silica were performed on Merck 60 silica gel (0.040-0.063 mm). The chromatographies on an alumina column were performed on Sigma-Aldrich aluminum oxide, neutral, activated, Brochmann I.

Spectroscopy
a. Nuclear Magnetic Resonance

The NMR spectra ($^1$H, $^{13}$C and $^{31}$P) were acquired using a Bruker Avance 400 MHz NanoBay spectrometer (9.4 Tesla magnet), equipped with a BBFO measuring probe, multicore 5 mm in diameter, of gradient Z and $^2$H lock. The chemical shifts (δ) are expressed in parts per million (ppm). The following abbreviations are used:
  s: singlet, bs: broad singlet, d: doublet, t: triplet, q: quartet, m: multiplet, dd: doubled doublet, td: double triplet, dq: doubled quartet, ddd: doublet of doubled doublets.

b. Mass Spectrometry

The mass spectra (LC-MS) were acquired using a single quadrupole Waters ZQ 2000 spectrometer with ESI/APCI multimode source equipped with a Waters XBridge C18, 3.5 µm, 4.6×100 mm column.

c. High-Resolution Mass Spectrometry

The analyses were performed using a QStar Elite mass spectrometer (Applied Biosystems SCIEX) equipped with a pneumatically-assisted atmospheric pressure ionization (API) source. The sample was ionized in positive electrospray mode under the following conditions: electrospray voltage (ISV): 5500 V; orifice voltage (OR): 20 V; spraying gas (air) pressure: 20 psi. The high-resolution mass spectrum (MS) was obtained with a time of flight (TOF) analyzer. The exact mass measurement was performed in triplicate with an internal double calibration.

Various
  Melting point machine: the melting points were acquired using a B-540 Büchi melting point machine.

Compound (2)

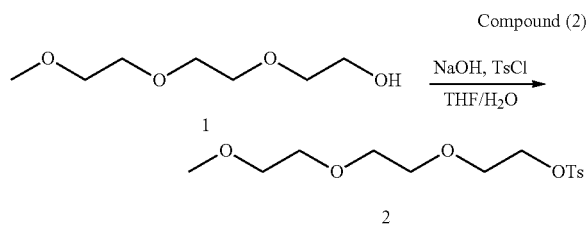

A solution of sodium hydroxide (14.56 g of sodium hydroxide in 60 mL of water, 0.36 mol) was added dropwise to a solution of triethylene glycol monomethyl ether 1 (33.2 g, 0.2 mol) in tetrahydrofuran (50 mL). The reaction medium was cooled to 0° C. and a solution of 4-toluenesulfonyl chloride in tetrahydrofuran (38.5 g in 60 mL, 0.2 mol) was added dropwise. At the end of the addition, the reaction medium was stirred at room temperature for 12 hours. The reaction progress was monitored by TLC. After this period, the reaction was complete. The reaction medium was extracted with diethyl ether (3×100 mL). The organic phases were combined, dried over sodium sulfate and filtered. The solvent was removed under reduced pressure to give compound 2 in the form of a slightly yellow oil. The compound was sufficiently pure to be used in the rest of the synthesis without further purification (57.22 g, 89%). $^1$H NMR (200 MHz, CDCl$_3$): δ: 7.77 (d, J=8.3 Hz, 2H), 7.31 (d, J=8.3 Hz, 2H), 4.13 (m, 2H), 3.57 (m, 10H), 3.33 (s, 3H), 2.41 (s, 3H).

Compound (4)

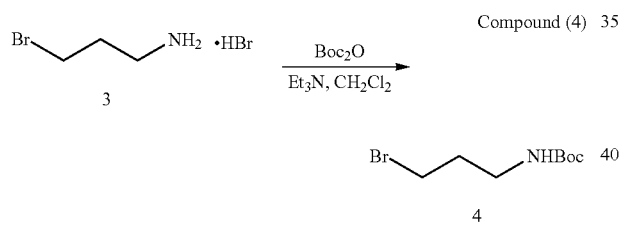

Di-tert-butyl dicarbonate (3.71 g, 16 9 mmol) and triethylamine (10 mL). were added to a solution of 3-bromopropylamine hydrobromide 3 (3.72 g, 16.9 mmol) in dichloromethane (100 mL). The reaction mixture was stirred at room temperature for 12 hours. The reaction progress was monitored by TLC. After this period, the reaction was complete. The solvent was removed under reduced pressure. Saturated sodium chloride solution (100 mL) was added to this residue and the mixture was extracted with diethyl ether (2×50 mL). The organic phases were combined, washed with saturated sodium chloride solution (3×50 mL) and dried over sodium sulfate. After filtration, the solvent was removed under reduced pressure to give compound 4 in the form of a slightly brown solid. The compound was sufficiently pure to be used in the rest of the synthesis without further purification (3.50 g, 87%). $^1$H NMR (200 MHz, CDCl$_3$) δ: 4.63 (s, 1H), 3.42 (t, J=6.5 Hz, 2H), 3.26 (td, J=6.5; 6.5 Hz, 2H), 2.03 (m, J=6.5 Hz, 2H), 1.43 (s, 9H). HMRS (ESI) calculated for C$_8$H$_{16}$NO$_2$Br [M+H$^+$], m/z 255.0703. found: 255.0695.

Compound (6a)

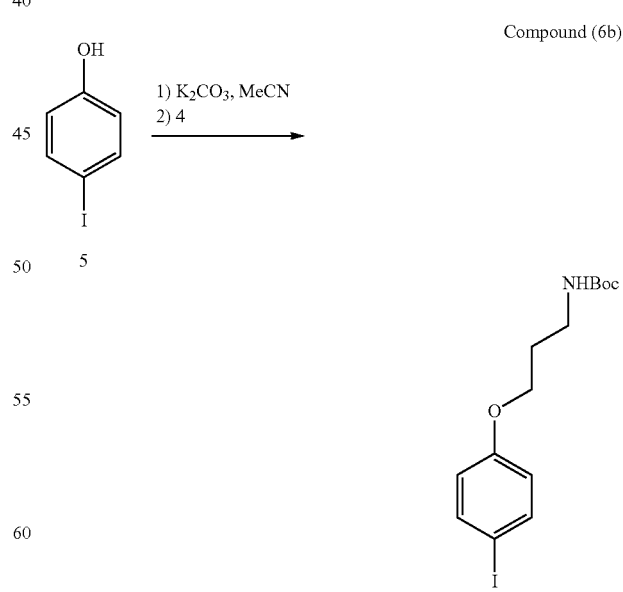

The tosyl derivative 2 (8.7 g, 27 mmol) was added to a suspension of 4-iodophenol 5 (4.0 g, 18 mmol) and potassium carbonate (12.4 g, 90 mmol) in dimethylformamide (50 mL). The reaction mixture was refluxed for 36 hours. The reaction progress was monitored by TLC. After this period, the reaction was complete. The reaction mixture was cooled to room temperature and filtered through a sinter funnel. The filtrate was concentrated under reduced pressure and the residue was purified by chromatography on a column of silica (cyclohexane/ethyl acetate from 95/5 to 50/50 in 5% increments) to give compound 6a in the form of a yellow oil (3.38 g, 51%). $^1$H NMR (200 MHz, CDCl$_3$) δ: 7.52 (d, J=9.0 Hz, 2H), 6.68 (d, J=9.0 Hz, 2H), 4.07 (t, J=6.0 Hz, 2H), 3.82 (t, J=5.2 Hz, 2H), 3.62 (m, 6H), 3.54 (m, 2H), 3.36 (s, 3H). $^{13}$C NMR (50 MHz, CDCl$_3$) δ: 158.7; 138.2; 117.1; 82.9; 71.9; 70.9; 70.7; 70.6; 69.6; 67.6; 50.1. HMRS (ESI) calculated for C$_{13}$H$_{19}$O$_4$I [M+H$^+$], m/z 384.0666. found: 384.0668.

Compound (6b)

Sodium carbonate (5.65 g, 40.9 mmol) was added to a solution of 4-iodophenol 5 (3.00 g, 13.6 mmol) in anhydrous acetonitrile (100 mL). The reaction was refluxed for 1 hour and the bromo derivative 4 (2.60 g, 10.9 mmol) was then added to this suspension. The reaction mixture was refluxed for 12 hours. The reaction progress was monitored by TLC. After this period, the reaction was complete. The reaction mixture was cooled to room temperature and the solvent was removed under reduced pressure. Water (100 mL) was added to this residue, and the mixture was extracted with dichloromethane (2×50 mL). The organic phases were combined, dried over sodium sulfate and filtered. The solvent was removed under reduced pressure and the residue was purified by chromatography on a column of silica (dichloromethane) to give compound 6b in the form of a white solid (3.10 g, 75%). m.p.: 79-80° C. $^1$H NMR (500 MHz, CDCl$_3$) δ: 7.52 (d, J=8.9 Hz, 2H), 6.64 (d, J=8.9 Hz, 2H), 4.69 (s, 1H), 3.95 (t, J=6.2 Hz, 2H), 3.29 (td, J=6.2; 6.2 Hz, 2H), 1.94 (m, J=6.2 Hz, 2H), 1.41 (s, 9H), $^{13}$C NMR (125 MHz, CDCl$_3$) δ: 158.7; 155.9; 138.2; 116.9; 82.9; 65.9; 37.9. HMRS (ESI) calculated for C$_{14}$H$_{20}$NO$_3$I [M+H$^+$], m/z 378.0561. found: 378.0559.

by chromatography on silica (95/5 to 90/10 dichloromethane/ethyl acetate) to give compound 7a in the form of a slightly yellow oil (0.64 g, 70%). $^1$H NMR (200 MHz, CDCl$_3$) δ: 7.36 (d, J=8.8 Hz, 2H), 6.82 (d, J=8.8 Hz, 2H), 4.11 (t, J=5.8 Hz, 2H), 3.83 (t, J=5.1 Hz, 2H), 3.64 (m, 6H), 3.53 (m, 2H), 3.34 (s, 3H), 0.24 (s, 9H). $^{13}$C NMR (50 MHz, CDCl$_3$) δ: 159.0; 133.3; 115.4; 114.4; 105.2; 92.3; 71.9; 70.8; 70.6; 70.5; 69.6; 67.4; 58.9; 0.1. HMRS (ESI) calculated for C$_{18}$H$_{28}$O$_4$Si [M+H$^+$], m/z 337.1830. found: 337.1828.

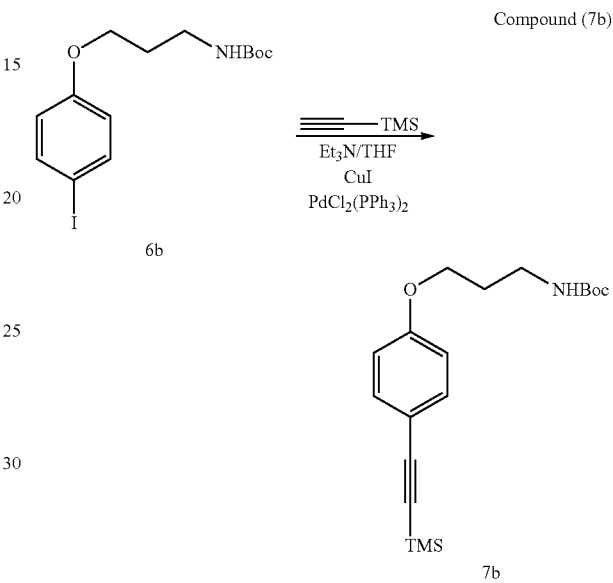

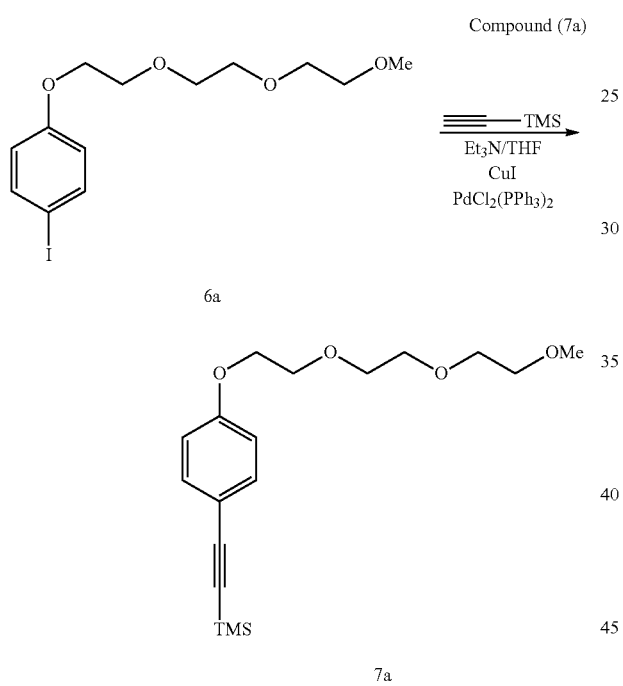

A solution of iodo compound 6a (1.00 g, 2.7 mmol) in a mixture of tetrahydrofuran (20 mL) and triethylamine (20 mL) was degassed with stirring for 20 minutes. Trimethylsilylacetylene (0.8 g, 8.2 mmol) was added to this solution, followed by addition of bis(triphenylphosphine)palladium (II) dichloride (19 mg, 0.02 mmol) and copper iodide(I) (10 mg, 0.054 mmol). The reaction mixture was stirred at room temperature for 12 hours. The reaction progress was monitored by TLC. After this period, the reaction was complete. The solvents were removed under reduced pressure. Saturated ammonium chloride solution (50 mL) was added to the residue, and the mixture was extracted with dichloromethane (2×25 mL). The organic phases were combined and washed with saturated ammonium chloride solution (50 mL) and then with sodium chloride solution (2×50 mL) and were finally dried over sodium sulfate. After filtration, the solvent was removed under reduced pressure and the residue was purified A solution of iodo derivative 6b (2.50 g, 6.6 mmol) in a mixture of tetrahydrofuran (20 mL) and triethylamine (20 mL) was degassed with stirring for 20 minutes. Trimethylsilylacetylene (1.95 g, 19.8 mmol) was added to this solution, followed by addition of bis(triphenylphosphine)palladium (II) dichloride (46 mg, 0.06 mmol) and copper(I) iodide (25 mg, 0.13 mmol). The reaction was stirred at room temperature for 12 hours. The reaction progress was monitored by TLC. After this period, the reaction was complete. The solvents were removed under reduced pressure. Saturated ammonium chloride solution (50 mL) was added to the residue, and the mixture was extracted with dichloromethane (2×25 mL). The organic phases were combined and washed with saturated ammonium chloride solution (50 mL) and then with saturated sodium chloride solution (2×50 mL) and finally dried over sodium sulfate. After filtration, the solvent was removed under reduced pressure and the residue was purified by chromatography on a column of silica (1/1 dichloromethane/pentane and then dichloromethane) to give compound 7b in the form of a white solid (1.50 g, 65%). m.p.: 92-93° C. $^1$H NMR (200 MHz, CDCl$_3$) δ: 7.37 (d, J=8.7 Hz, 2H), 6.78 (d, J=8.7 Hz, 2H), 4.69 (s, 1H), 3.99 (t, J=6.2 Hz, 2H), 3.29 (td, J=6.2 Hz and J=6.2 Hz, 2H), 1.95 (m, J=6.2 Hz, 2H), 1.42 (s, 9H), 0.22 (s, 9H). $^{13}$C NMR (100 MHz, CDCl$_3$) δ: 159.08; 156.13; 133.61; 115.54; 114.44; 105.28; 92.63; 79.41; 65.92; 38.06; 29.66; 28.54; 0.20. HMRS (ESI) calculated for C$_{19}$H$_{29}$NO$_3$Si [M+H$^+$], m/z 348.1989. found: 348.1993.

Compound (8a)

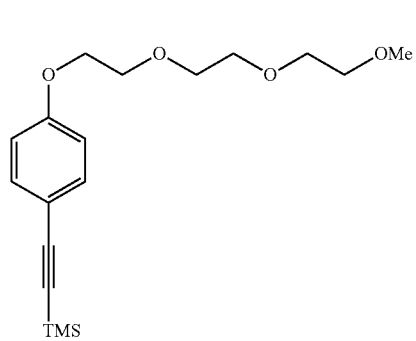

Potassium carbonate (7.0 g, 58 mmol) was added to a solution of silyl derivative 7a (5.7 g, 17 mmol) in a mixture of tetrahydrofuran (60 mL) and methanol (60 mL). The reaction medium was stirred at room temperature for 2 hours. The reaction progress was monitored by TLC. After this period, the reaction was complete. The reaction mixture was filtered and the filtrate was concentrated under reduced pressure. The residue was purified by chromatography on a column of silica (95/5 and then 90/10 dichloromethane/ethyl acetate) to give compound 8a in the form of a yellow oil (3.9 g, 87%). $^1$H NMR (200 MHz, CDCl$_3$) δ: 7.40 (d, J=8.8 Hz, 2H), 6.84 (d, J=8.8 Hz, 2H), 4.12 (t, J=5.1 Hz, 2H), 3.84 (t, J=4.5 Hz, 2H), 3.64 (m, 6H), 3.54 (m, 2H), 3.36 (s, 3H), 2.98 (s, 1H). $^{13}$C NMR (50 MHz, CDCl$_3$) δ: 159.4; 133.7; 114.8; 114.5; 83.9; 76.5; 72.1; 71.0; 70.8; 70.7; 69.8; 67.7; 59.1.

Compound (8b)

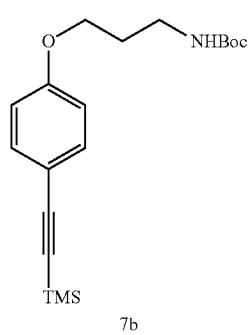

Potassium carbonate (1.52 g, 11.0 mmol) was added to a solution of silyl derivative 7b (1.27 g, 3.7 mmol) in a mixture of tetrahydrofuran (30 mL) and methanol (30 mL). The reaction medium was stirred at room temperature for 2 hours. The reaction progress was monitored by TLC. After this period, the reaction was complete. The reaction mixture was filtered and the filtrate was concentrated under reduced pressure. The residue was purified by chromatography on a column of silica (pentane/dichloromethane, 50/50 up to 100% in 10% increments) to give compound 8b in the form of a white solid (0.86 g, 85%). $^1$H NMR (200 MHz, CDCl$_3$) δ: 7.39 (d, J=8.7 Hz, 2H), 6.81 (d, J=8.7 Hz, 2H), 4.69 (s, 1H), 3.99 (t, J=6.2 Hz, 2H), 3.29 (td, J=6.2 Hz and J=6.2 Hz, 2H), 2.97 (s, 1H), 1.95 (m, J=6.2 Hz, 2H), 1.42 (s, 9H).

Compound (10)

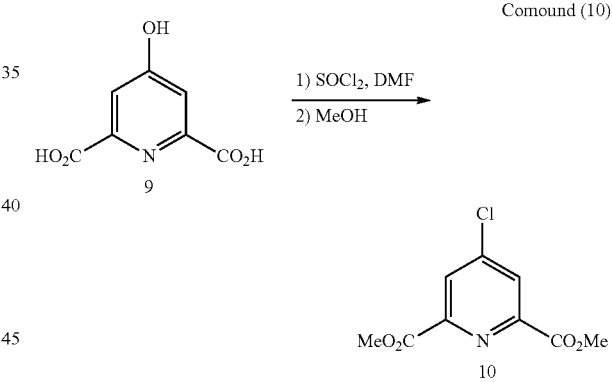

A few drops of dimethylformamide were added to a solution of chelidamic acid 9 (17 g, 93 mmol) in thionyl chloride (95 mL). This solution was heated at 100° C. for 48 hours. The thionyl chloride was moved under reduced pressure. Dichloromethane (50 mL) was added to this residue, and the mixture was cooled to 0° C. Anhydrous methanol (40 mL) was added dropwise to this mixture over a period of 10 minutes, and the mixture was allowed to warm to room temperature overnight. The solvents were removed under reduced pressure and saturated sodium bicarbonate solution (100 mL) was added to this residue. The mixture was filtered and the filtrate was extracted with dichloromethane (3×50 mL), the organic phases were combined, dried over sodium sulfate, filtered and evaporated under reduced pressure to give a white solid identified as compound 10. The product was sufficiently pure to be used in the rest of the synthesis without further purification (13.3 g, 63%). $^1$H NMR (300 MHz, CDCl$_3$) δ: 8.32 (s, 2H), 4.06 (s, 6H).

Compound (11)

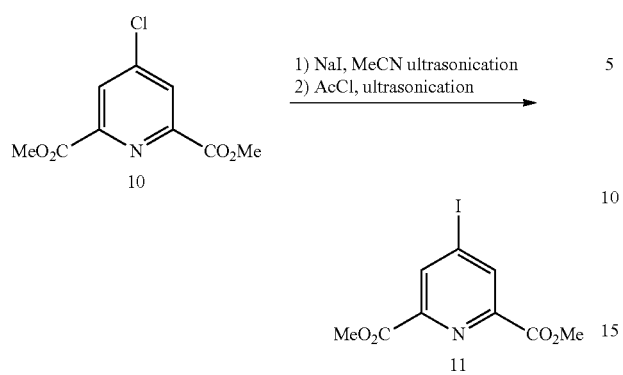

Sodium iodide (39 g, 262 mmol) was added to a solution of compound 10 (6.0 g, 26.2 mmol) in anhydrous acetonitrile (140 mL) and the mixture was ultrasonicated for 20 minutes. Acetyl chloride (5.55 mL, 78.6 mmol) was added to this mixture, and the mixture was ultrasonicated for 5 hours. Saturated sodium bicarbonate solution (75 mL) was added to this solution, cooled to 0° C., followed by addition of water (100 mL). The mixture was extracted with ethyl acetate (2×50 mL) and the organic phases were combined, washed with 0.2 M thiosulfate solution and finally dried over sodium sulfate, filtered and then concentrated under reduced pressure. Methanol (40 mL) was added to this residue, and the mixture was stirred for 20 minutes and then filtered to give a white solid identified as compound 11. The product was sufficiently pure to be used in the rest of the synthesis without further purification (6.9 g, 82%). $^1$H NMR (300 MHz, CDCl$_3$) δ: 8.68 (s, 2H), 4.05 (s, 6H).

Compound (12)

Methanol (35 mL) was added to a solution of diester 11 (7.0 g, 21.8 mmol) in dichloromethane (50 mL), cooled to 0° C., followed by addition of sodium borohydride (540 mg, 14.2 mmol). The mixture was stirred for 2 hours at 0° C., followed by addition of 1 M hydrochloric acid solution (20 mL). The solvent was removed under reduced pressure and saturated sodium bicarbonate solution (100 mL) was added to the residue, and the mixture was then extracted with ethyl acetate (4×30 mL). The organic phases were combined, dried over sodium sulfate, filtered and concentrated under reduced pressure. The residue was purified by chromatography on a column of silica (cyclohexane/ethyl acetate, 60/40 up to 0/100 in 10% increments) to give compound 12 as a white solid (3.8 g, 60%). $^1$H NMR (300 MHz, CDCl$_3$) δ: 8.41 (s, 1H), 7.99 (s, 1H), 4.85 (s, 2H), 4.02 (s, 3H). $^{13}$C NMR (75 MHz, CDCl$_3$) δ: 164.44; 161.44; 147.31; 133.34; 133.06; 106.97; 64.31; 53.29.

Compound (13a)

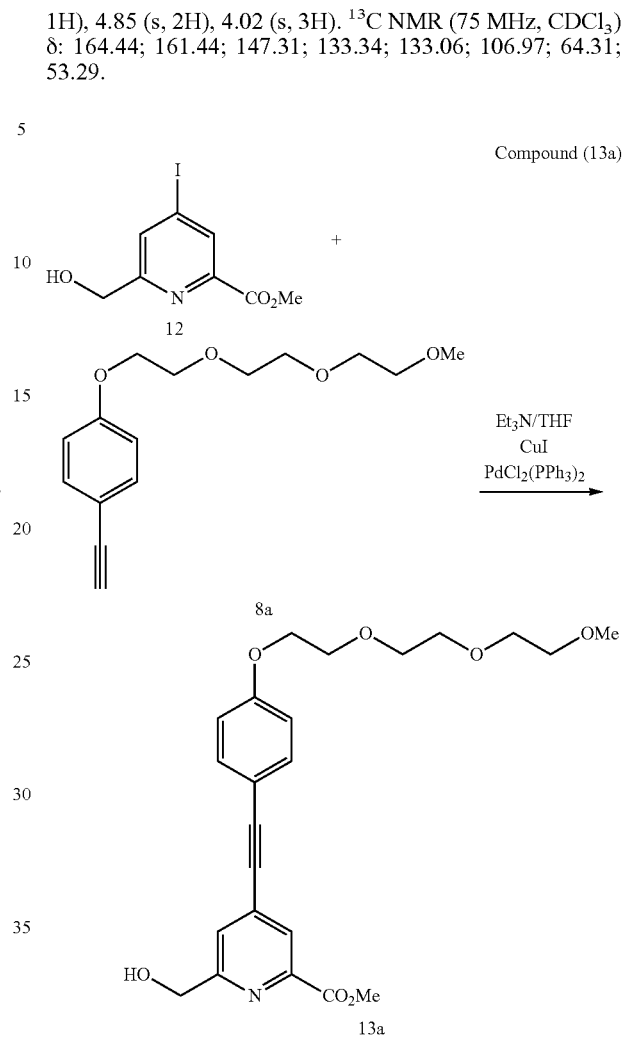

A solution of acetylenic derivative 8a (3.9 g, 15 mmol) and of iodo derivative 12 (2.8 g, 9.6 mmol) in a mixture of tetrahydrofuran (20 mL) and triethylamine (20 mL) was degassed with stirring for 20 minutes. Bis(triphenylphosphine)palladium(II) dichloride (104 mg, 0.15 mmol) and copper(I) iodide (56 mg, 0.29 mmol) were added to this solution. The reaction was stirred at room temperature for 12 hours. The reaction progress was monitored by TLC. After this period, the reaction was complete. The solvents were removed under reduced pressure. Saturated ammonium chloride solution (50 mL) was added to the residue and the mixture was extracted with dichloromethane (2×25 mL). The organic phases were combined, washed with saturated ammonium chloride solution (50 mL) and then with saturated sodium chloride solution (2×50 mL) and then dried over sodium sulfate. After filtration, the solvent was removed under reduced pressure and the residue was purified by chromatography on a column of silica (1/1 dichloromethane/methanol) to give product 13a in the form of a yellow solid (3.2 g, 78%). m.p.: 47° C. $^1$H NMR (500 MHz, CDCl$_3$) δ: 8.04 (s, 1H), 7.56 (s, 1H), 7.45 (d, J=8.8 Hz, 2H), 6.89 (d, J=8.8 Hz, 2H), 4.82 (s, 2H), 4.13 (m, 2H), 3.97 (s, 3H), 3.84 (m, 3H), 3.71 (m, 2H), 3.64 (m, 4H), 3.52 (m, 2H), 3.35 (s, 3H), 1.89 (s, 1H). $^{13}$C NMR (50 MHz, CDCl$_3$) δ: 165.4; 160.7; 160.1; 147.3; 134.1; 133.8; 125.8; 125.5; 115.1; 114.1; 95.9; 85.4; 72.1. HMRS (ESI) calculated for $C_{23}H_{27}NO_7$ [M+H$^+$], m/z 430.1860. found: 430.1858.

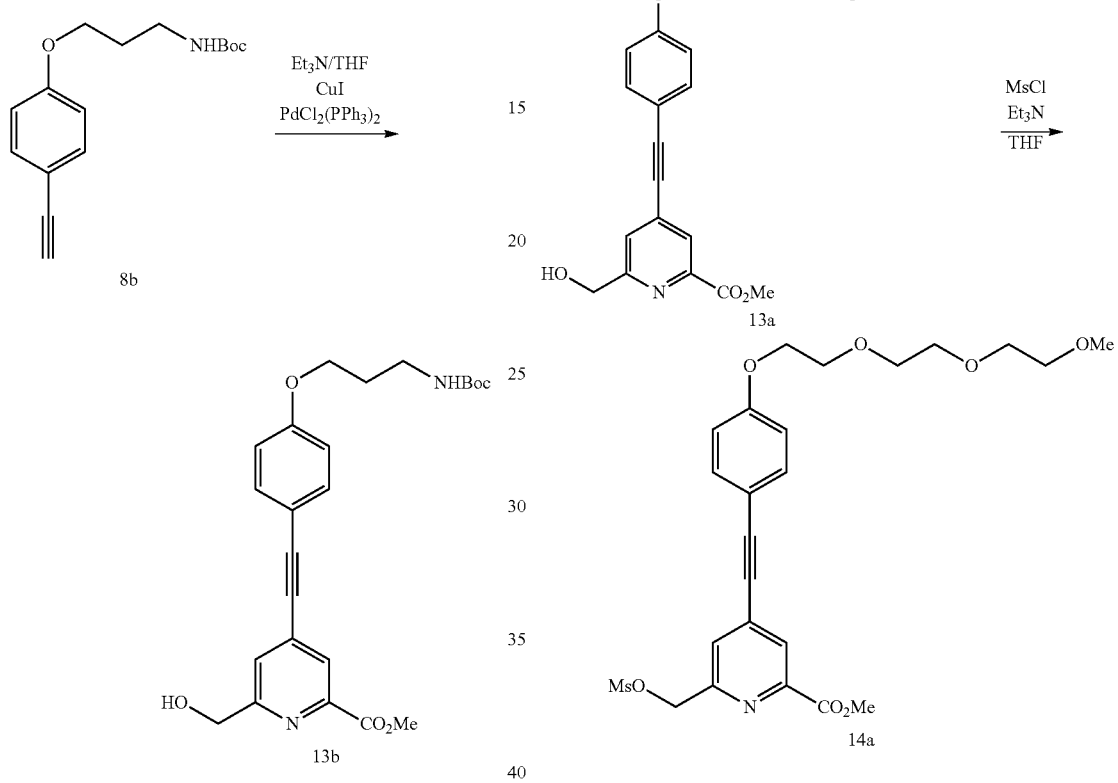

A solution of acetylenic derivative 8b (0.864 g, 3.1 mmol) and of iodo derivative 12 (0.735 g, 2.5 mmol) in a mixture of tetrahydrofuran (20 mL) and of triethylamine (20 mL) was degassed with stirring for 20 minutes. Bis(triphenylphosphine)palladium(II) dichloride (22 mg, 0.031 mmol) and copper(I) iodide (12 mg, 0.063 mmol) were added to this solution. The reaction was stirred at room temperature for 12 hours. The reaction progress was monitored by TLC. After this period, the reaction was complete. The solvents were removed under reduced pressure. Saturated ammonium chloride solution (50 mL) was added to the residue, and the mixture was extracted with dichloromethane (2×25 mL). The organic phases were combined, washed with saturated ammonium chloride solution (50 mL) and then with saturated sodium chloride solution (2×50 mL) and then dried over sodium sulfate. After filtration, the solvent was removed under reduced pressure and the residue was purified by chromatography on a column of silica (98/2 dichloromethane/methanol) to give compound 13b in the form of a white solid (0.910 g, 82%). m.p.: 143-144° C. $^1$H NMR (500 MHz, CDCl$_3$) δ: 8.04 (s, 1H), 7.58 (s, 1H), 7.45 (d, J=8.7 Hz, 2H), 6.86 (d, J=8.7 Hz, 2H), 4.83 (d, J=5.4 Hz, 2H), 4.75 (s, 1H), 4.01 (t, J=6.1 Hz, 2H), 3.97 (s, 3H), 3.31 (td, J=6.1; 6.1 Hz, 2H), 1.96 (m, J=6.1 Hz, 2H), 1.41 (s, 9H). $^{13}$C NMR (125 MHz, CDCl$_3$) δ: 165.4; 160.8; 160.1; 156.2; 147.3; 134.1; 133.8; 125.8; 125.4; 114.9; 113.9; 95.9; 85.4; 66.1; 64.8; 53.2; 38.1; 29.7; 28.6. HMRS (ESI) calculated for C$_{24}$H$_{28}$N$_2$O$_6$ [M+H$^+$], m/z 441.2020. found: 441.2021.

Triethylamine (212 mg, 0.21 mmol) and then mesyl chloride (88 mg, 0.77 mmol) were added to a solution, cooled to 5° C., of alcohol 13a (300 mg, 0.7 mmol) in tetrahydrofuran (20 mL). The reaction medium was stirred at 0° C. for 30 minutes and then at room temperature for 12 hours. The reaction progress was monitored by TLC. After this period, the reaction was complete. The solvent was removed under reduced pressure. Water (30 mL) was added to the residue, and the mixture was extracted with dichloromethane (2×30 mL). The organic phases were combined, washed with water (30 mL) and dried over sodium sulfate. After filtration, the solvent was removed under reduced pressure and the residue was purified by chromatography on a column of silica (8/2 dichloromethane/ethyl acetate) to give compound 14a in the form of a slightly yellow solid (330 mg, 93%). $^1$H NMR (500 MHz, CDCl$_3$) δ: 8.09 (s, 1H), 7.66 (s, 1H), 7.45 (d, J=8.7 Hz, 2H), 6.88 (d, J=8.7 Hz, 2H), 5.37 (s, 2H), 4.12 (m, 2H), 3.97 (s, 3H), 3.83 (m, 2H), 3.69 (m, 2H), 3.62 (m, 4H), 3.51 (m, 2H), 3.33 (s, 3H), 3.13 (s, 3H), $^{13}$C NMR (50 MHz, CDCl$_3$) δ: 164.9; 160.1; 154.6; 147.8; 134.6; 133.7; 126.6; 126.3; 114.9; 113.6; 96.8; 84.9; 71.9; 70.9; 70.7; 70.6; 69.6; 67.6; 59.1; 53.1; 38.1. HMRS (ESI) calculated for C$_{24}$H$_{29}$NO$_9$S [M+H$^+$], m/z 508.1636. found: 508.1637.

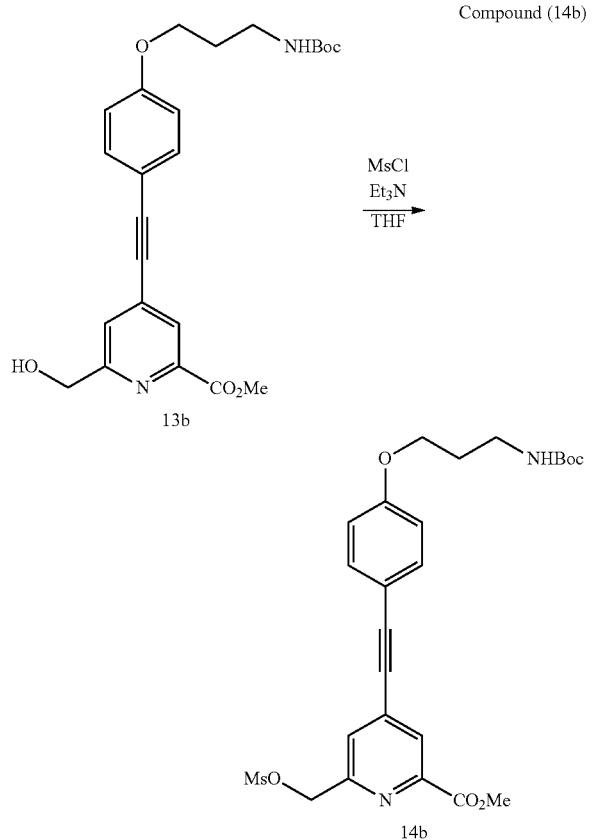

Compound (14b)

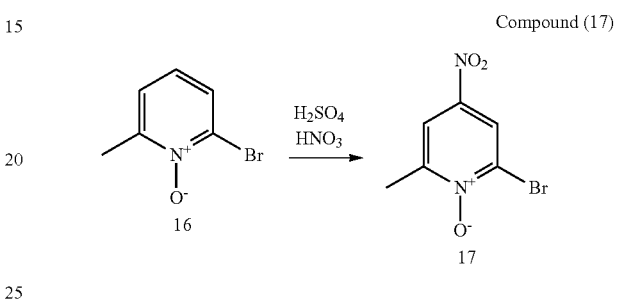

Triethylamine (18.1 mg, 150 µmol) was added dropwise to a solution of alcohol 13b (21.9 mg, 50 µmol) in anhydrous tetrahydrofuran (1 mL) under an inert atmosphere. A solution of mesyl chloride (6 µL, 75 µmol) in anhydrous tetrahydrofuran (0.2 mL) was added dropwise to this mixture, cooled to 4° C. The reaction progress was monitored by TLC. After 20 minutes, the reaction was complete. The solvent was removed under reduced pressure. The residue was dissolved in dichloromethane (4 mL) and this solution was washed with water (3×5 mL). The organic phase was dried over magnesium sulfate, filtered and concentrated under reduced pressure to give a green-yellow oil (26.9 mg, quantitative). Product 14b was sufficiently pure to be used in the rest of the synthesis without further purification.

Compound (16)

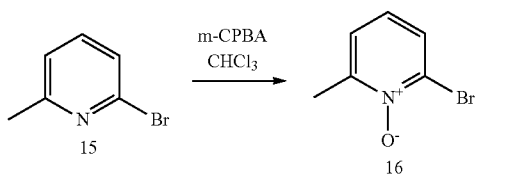

m-Chloroperbenzoic acid (62 g, 261 mmol) was added at room temperature to a solution of 2-bromo-6-methylpyridine 15 (30 g, 174 mmol) in chloroform (300 mL). The mixture was heated at 65° C. for 20 hours and then cooled to 0° C. for 3 hours. After filtration of the precipitate, the filtrate was concentrated under reduced pressure. Aqueous sodium hydroxide solution (2N, 75 mL) was added to this residue, and this solution was extracted with dichloromethane (3×100 mL). The organic phases were combined, dried over sodium sulfate, filtered and concentrated under reduced pressure to give compound 16 in the form of a yellow solid, which is used in the rest of the synthesis without further purification (15 g, 67%); m.p.: 48-55° C.; $^1$H NMR (400 MHz, CDCl$_3$) δ: 7.55 (dd, J=7.9 Hz, 1.6 Hz, 1H), 7.23 (dd, J=7.9 Hz, 1.6 Hz, 1H), 7.01 (t, J=7.9 Hz, 1H), 2.57 (s, 3H); $^{13}$C NMR (100 MHz, CDCl$_3$) δ: 151.2; 133.5; 128.7; 125.3; 125.2; 19.3. HMRS (ESI) calculated for C$_6$H$_7$NOBr [M+H$^+$], m/z 187.9711. found: 187.9698.

Compound (17)

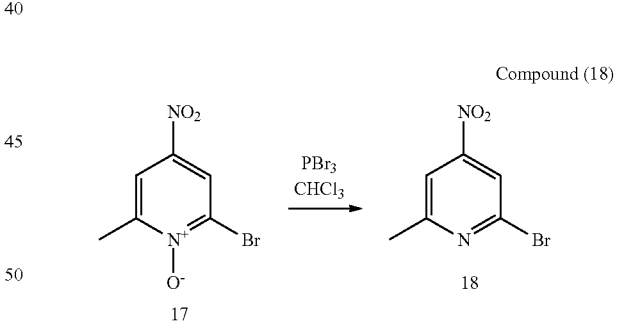

Fuming nitric acid (10.4 mL, 252 mmol) was added dropwise to a solution of compound 16 (10 g, 53 mmol) in concentrated sulfuric acid (14.1 mL, 265 mmol), cooled to 0° C. The mixture was stirred at room temperature for 15 minutes and then heated at 85° C. for 16 hours. The solution was then cooled to room temperature and poured onto crushed ice (60 g). After stirring for 15 minutes, the precipitate was filtered off and washed with water. The yellow solid was dissolved in dichloromethane and the solution was dried over sodium sulfate, filtered and concentrated under reduced pressure to give compound 17 in the form of a yellow solid, which was used in the rest of the synthesis without further purification. m.p.: 137-138° C.

Compound (18)

Phosphorus tribromide (14.2 mL, 150 mmol) was added to a solution of N-oxide compound 17 (11.7 g, 50 mmol) in chloroform (300 mL), and the mixture was heated at 60° C. under argon for 16 hours. The solution was cooled to room temperature and concentrated under reduced pressure, and was then poured into an ice-cold 2M sodium hydroxide solution (260 mL). The mixture was extracted with dichloromethane (3×100 mL), and the organic phases were combined, dried over sodium sulfate and concentrated under reduced pressure. The resulting oil was purified by chromatography on a column of silica, using dichloromethane as eluent, thus giving compound 18 in the form of a yellow solid (8.4 g, 78%). m.p. 51-52° C.

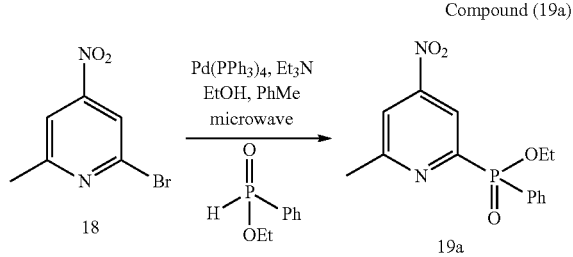 [SMILES: Cc1cc([N+](=O)[O-])cc(Br)n1 ; CCO[PH](=O)c1ccccc1 ; CCOP(=O)(c1ccccc1)c1cc([N+](=O)[O-])cc(C)n1]

Compound (19a)

Ethyl phenylphosphinate (0.95 g, 5.60 mmol) and triethylamine (2.6 mL, 19.0 mmol) were added to a solution of 2-bromo-6-methyl-4-nitropyridine 18 (1.01 g, 4.68 mmol) in anhydrous toluene (10 mL). The mixture was degassed via three freezing-thawing cycles. Tetrakis(triphenylphosphine)palladium(0) (83 mg, 0.07 mmol) was added to this solution and the mixture was degassed again three times, before being stirred at reflux for 16 hours under argon. The reaction progress was monitored by TLC. After this period, the reaction was complete. The solution was cooled and diluted with dichloromethane (20 mL). The mixture was washed with aqueous hydrochloric acid solution (1 M, 2×15 mL), followed by washing with water (3×15 mL). The organic phase was dried over potassium carbonate, filtered, and the solvent was removed under reduced pressure to give a dark residue, which was purified by chromatography on a column of silica (dichloromethane/0.5% methanol), thus giving compound 19a in the form of a yellow oil (645 mg, 45%). $^1$H NMR (400 MHz, CDCl$_3$) δ: 8.55 (dd, J=5.6 Hz, J=1.4 Hz, 1H), 7.97 (ddd, J=11.2 Hz, 7.7 Hz, 1.4 Hz, 2H), 7.90 (d, J=1.4 Hz, 1H), 7.55 (td, J=7.7 Hz, 1.4 Hz, 1H), 7.46 (td, J=7.7 Hz, 3.5 Hz, 2H), 4.15 (qd, J=7.0 Hz, 4.2 Hz, 2H), 2.72 (s, 3H), 1.38 (t, J=7.0 Hz, 3H); $^{13}$C NMR (100 MHz, CDCl$_3$) δ: 163.0 (d, J=21 Hz), 158.1 (d, J=167 Hz), 154.0 (d, J=13 Hz), 132.9 (d, J=3 Hz), 132.5 (d, J=10 Hz), 129.1 (d, J=140 Hz), 128.5 (d, J=13 Hz), 117.6 (d, J=24 Hz), 117.5 (d, J=3 Hz), 62.2 (d, J=6 Hz), 24.9, 16.4; $^{31}$P NMR (162 MHz, CDCl$_3$) δ: 23.7. HMRS (ESI) calculated for $C_{14}H_{16}N_2O_4P$ [M+H$^+$], m/z 307.0848. found: 307.0851.

Compound (19b)

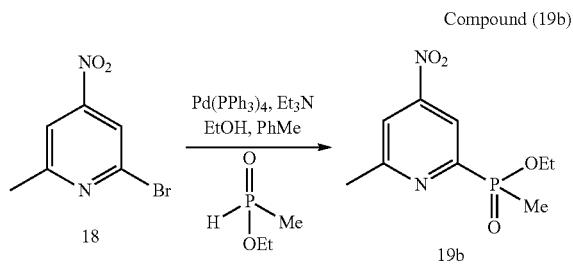 [SMILES: Cc1cc([N+](=O)[O-])cc(Br)n1 ; CCO[PH](C)=O ; CCOP(C)(=O)c1cc([N+](=O)[O-])cc(C)n1]

Water (264 μL, 14.7 mmol) was added, at 0° C., without particular precaution, to diethyl methyl phosphonite (2 g, 14.7 mmol). The reaction mixture was warmed to room temperature over 1 hour and then stirred for 16 hours. A solution of 2-bromo-6-methyl-4-nitropyridine 18 (2.1 g, 12.3 mmol) in anhydrous toluene (20 mL) and triethylamine (6 mL, 43.0 mmol) was added to this mixture. The mixture was degassed via three freezing-thawing cycles. Tetrakis(triphenylphosphine)palladium(0) (320 mg, 0.27 mmol) was added to this solution, and the mixture was again degassed three times, before being stirred at reflux for 16 hours under argon. The reaction progress was monitored by TLC. After this period, the reaction was complete. The solution was cooled and diluted with dichloromethane (20 mL). The mixture was washed with aqueous hydrochloric acid solution (1 M, 2×15 mL), followed by washing with water (3×15 mL). The organic phase was dried over potassium carbonate and filtered, and the solvent was removed under reduced pressure to give a dark residue, which was purified by chromatography on a column of silica (dichloromethane/1.6% methanol with 0.1% increments) thus giving compound 19b in the form of a colorless oil (700 mg, 29%). $^1$H NMR (400 MHz, CDCl$_3$) δ 7.75 (dd, J=7.0 Hz $^3$J$_{H-P}$ 10 Hz, 1H), 7.59 (td, $^3$J=7.0 Hz J=4.8 Hz, 1H), 7.16 (d, J=7.0 Hz, 1H), 3.86 (dqd, J=80 Hz J=7.0 Hz J=4.5 Hz, 2H), 2.50 (s, 3H), 1.66 (d, J=15 Hz, 3H), 1.61 (t, J=7.0 Hz, 3H); δ$_C$ (CDCl$_3$) 159.4 (d, J=20 Hz), 153.7 (d, J=158 Hz), 136.0 (d, J=10 Hz), 125.6 (d, J=3 Hz), 124.6 (d, J=22 Hz), 60.8 (d, J=6 Hz), 24.5, 16.3, 13.3 (d, J=103 Hz); δ$_P$ (CDCl$_3$)+41.2; m/z HMRS (ESI) calculated for $C_9H_{14}NO_2P$ [M+H$^+$], m/z 200.0858. found: 200.0862.

Compound (20a)

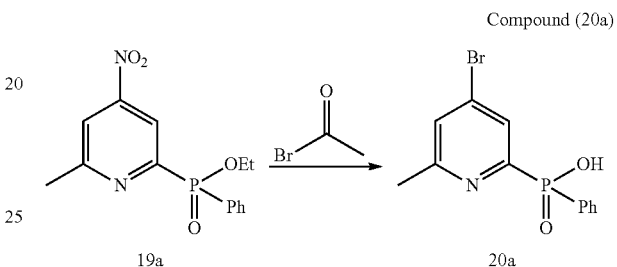

Acetyl bromide (15 mL, 0.2 mol) was added to the nitro derivative 19a (2.00 g, 6.54 mmol) and the mixture was stirred at 70° C. for 16 hours under argon. In the course of this period, a pale brown precipitate formed. The precipitate and the solution were added dropwise, cautiously, into methanol (100 mL) cooled to 0° C. The solvent was removed under reduced pressure to give the desired compound in the form of a pale brown solid, which was used directly in the rest of the synthesis without purification (1.81 g, 90%); $^1$H NMR (400 MHz, CD$_3$OD) δ: 8.33 (dd, J=7.2 Hz, 2.0 Hz, 1H), 8.23 (d, J=2.0 Hz, 1H), 7.95 (ddd, J=13.2 Hz, 7.6 Hz, 1.6 Hz, 2H), 7.63 (1H, td, J=7.6 Hz, 1.6 Hz, 1H), 7.55 (2H, td, J=7.6 Hz, 3.6 Hz), 2.77 (3H, s); $^{13}$C NMR (100 MHz, CD$_3$OD): δ 159.4 (d, J=20 Hz), 151.7 (d, J=160 Hz), 145.1 (d, J=10 Hz), 134.8 (d, J=3 Hz), 133.3 (d, J=10 Hz), 131.0 (d, J=24 Hz), 130.6 (d, J=3 Hz), 130.2 (d, J=140 Hz), 129.6 (d, J=12 Hz), 20.4; $^{31}$P NMR (162 MHz, CD$_3$OD) δ: 14.3. HMRS (ESI) calculated for $C_{12}H_{10}NO_2P$ [M+H$^+$], m/z 309.9633. found: 309.9648.

Compound (21a)

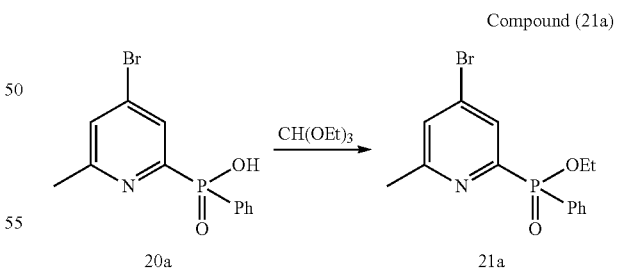

Ethyl orthoformate (50 mL) was added to the phosphinic acid 20a (1.80 g, 5.80 mmol) and the mixture was stirred at 140° C. for 72 hours under argon. The reaction progress was monitored by TLC. After this period, the reaction was complete. The solution was cooled to room temperature and the solvent was removed under reduced pressure. The residue was purified by chromatography on a column of silica (dichloromethane/0.5% methanol) to give compound 21a in the form of a yellow oil (1.08 g, 55%); $^1$H NMR (400 MHz, CDCl$_3$) δ: 8.04 (dd, J=6.3 Hz, 1.4 Hz, 1H), 7.95 (ddd, J=11.2 Hz, 7.0 Hz, 1.4 Hz, 2H), 7.51 (1H, td, 7.0 Hz, 1.4 Hz, 1H), 7.43 (td, J=7.0 Hz, 3.5 Hz, 2H), 7.37 (d, J=1.4 Hz, 1H), 4.11 (qd, J=7.0 Hz, 4.2 Hz, 2H), 2.52 (s, 3H), 1.34 (t, J=7.0 Hz, 3H); $^{13}$C NMR (100 MHz, CDCl$_3$) δ: 161.2 (d, J=22 Hz), 155.7 (d, J=165 Hz), 133.5 (d, J=15 Hz), 132.7 (d, J=3 Hz), 132.6 (d, J=10 Hz), 130.0 (d, J=139 Hz), 128.5 (d, J=3 Hz), 128.4 (d, J=23 Hz), 128.3 (d, J=13 Hz), 62.1 (d, J=6 Hz), 24.5, 16.7; $^{31}$P NMR (162 MHz, CDCl$_3$) δ: 25.5. HMRS (ESI) calculated for C$_{14}$H$_{16}$NO$_2$BrP [M+H$^+$], m/z 340.0102. found: 340.0102.

Compound (22a)

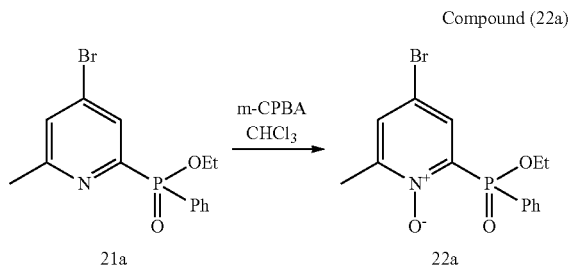 [SMILES: CCOP(=O)(c1ccccc1)c1cc(Br)cc(C)n1 ; "m-CPBACHCl3" ; CCOP(=O)(c1ccccc1)c1cc(Br)cc(C)[n+]1[O-]]

meta-Chloroperbenzoic acid (1.27 g, 7.35 mmol) was added to a solution of pyridyl derivative 21a (1.25 g, 3.68 mmol) in chloroform (20 mL). The resulting solution was stirred at 65° C. for 16 hours under argon. The reaction progress was monitored by TLC. After this period, the reaction was complete. The mixture was cooled to room temperature and the solvent was removed under reduced pressure to give a yellow oil. This oil was dissolved in dichloromethane and washed with sodium bicarbonate solution (0.5 M, 50 mL). The phases were separated and the aqueous phase was extracted with dichloromethane (3×30 mL). The organic phases were combined and dried over magnesium sulfate, and the solvent was removed under reduced pressure. The resulting yellow oil was purified by chromatography on a column of silica (dichloromethane/methanol, 0 to 2% in 0.1% increments) to give a yellow oil corresponding to compound 22a (1.11 g, 75%). $^1$H NMR (400 MHz, CDCl$_3$) δ: 8.05 (dd, J=7.7 Hz, 2.1 Hz, 1H), 7.98 (dd, J=7.7 Hz, 13.3 Hz, 2H), 7.50 (t, 7.7 Hz, 1H), 7.44 (d, J=2.1 Hz, 1H), 7.41 (td, J=7.7 Hz, 4.2 Hz, 2H), 4.13 (qd, J=5.6 Hz, 4.9 Hz, 2H), 2.32 (s, 3H), 1.34 (t, J=5.6 Hz, 3H); $^{13}$C NMR (100 MHz, CDCl$_3$) δ: 151.0 (d, J=4 Hz), 144.2 (d, J=149 Hz), 133.2 (d, J=11 Hz), 133.1 (d, J=4 Hz), 133.0 (d, J=11 Hz), 132.2 (d, J=4 Hz), 129.0 (d, J=152 Hz), 128.4 (d, J=14 Hz), 117.4 (d, J=12 Hz), 62.3 (d, J=6 Hz), 17.5, 16.7; $^{31}$P NMR (162 MHz, CDCl$_3$) δ: +21.2. HMRS (ESI) calculated for C$_{14}$H$_{16}$O$_3$BrNP [M+H$^+$], m/z 356.0051. found: 356.0061.

Compound (22c)

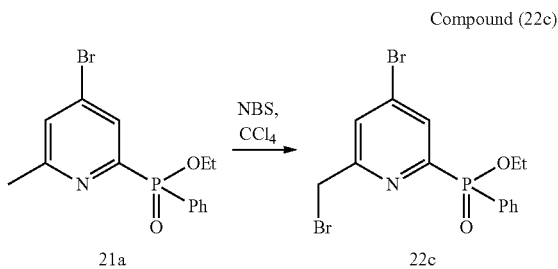

N-Bromosuccinimide (0.92 g, 5.21 mmol) was added to a solution of methylpyridyl derivative 21a (1.18 g, 3.47 mmol) in carbon tetrachloride (50 mL), followed by benzoyl peroxide (30 mg, 1.2 mmol). The mixture was refluxed under an inert atmosphere and with irradiation using a 100 W lamp for 16 hours. The reaction progress was monitored by $^1$H NMR. After this period, the reaction was complete. The reaction mixture was cooled to room temperature, the solvent was removed under reduced pressure and the residue was dissolved in dichloromethane (30 mL) and then washed with potassium carbonate solution (25 mL). The organic phase was dried over magnesium sulfate and filtered, and the solvent was removed under reduced pressure. The crude product was purified by chromatography on a column of silica (cyclohexane/ethyl acetate from 0% up to 30% in 2% increments) to give compound 22c in the form of a colorless oil (466 mg, 32%). $^1$H NMR (400 MHz, CDCl$_3$) δ: 8.16 (dd, J=6.0 Hz, J=1.6 Hz, 1H), 7.96 (ddd, J=12.4 Hz, J=6.8 Hz, J=1.6 Hz, 2H), 7.69 (d, J=1.6 Hz, 1H), 7.53 (td, J=6.8 Hz, J=1.6 Hz, 1H), 7.44 (td, J=6.8 Hz J=3.6 Hz, 2H), 4.49 (s, 2H), 4.12 (qd, J=6.8 Hz, J=4.2 Hz, 2H), 1.36 (t, J=6.8 Hz, 3H); $^{13}$C NMR (100 MHz, CDCl$_3$) δ: 159.2 (J=21 Hz), 156.1 (d, J=163 Hz), 134.5 (J=14 Hz), 133.0 (J=3 Hz), 132.7 (J=10 Hz), 130.8 (J=23 Hz), 129.4 (J=139 Hz), 128.7 (J=3 Hz), 128.6 (J=13 Hz), 62.4 (d, J=6 Hz), 32.5, 16.7; $^{31}$P NMR (162 MHz, CDCl$_3$) δ: 24.9; HMRS (ESI) calculated for C$_{14}$H$_{15}$NO$_2$PBr$_2$ [M+H$^+$], m/z 417.9207. found: 417.9212.

Compound (23a)

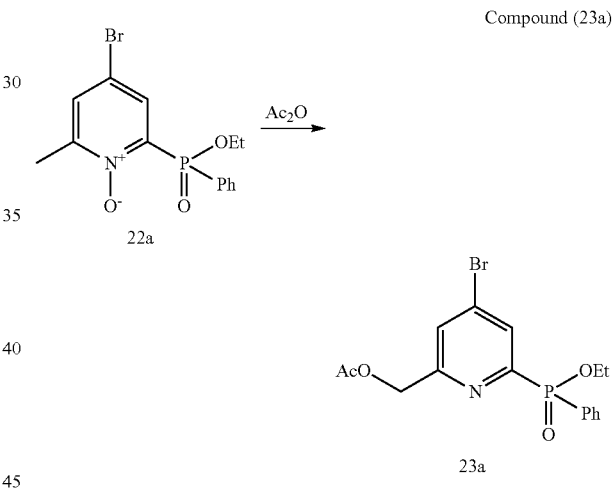

Acetic anhydride (35 mL) was added to the pyridyl N-oxide derivative 22a (1.8 g, 5.1 mmol) and the solution was heated at 120° C. for 3 hours with stirring. The reaction progress was monitored by $^{31}$P NMR. After this period, the reaction was complete. The solution was cooled to room temperature and the solvent was removed under reduced pressure. The residue was purified by chromatography on a column of silica (dichloromethane/methanol from 0 to 1% in 0.1% increments) to give a yellow oil corresponding to compound 23a (0.66 g, 33%); $^1$H NMR (400 MHz, CDCl$_3$) δ: 8.16 (dd, J=7.7 Hz, 2.1 Hz, 1H), 7.93 (dd, J=7.7 Hz, 13.3 Hz, 2H), 7.55 (d, J=2.1 Hz, 1H), 7.51 (t, J=7.7 Hz, 1H), 7.43 (td, J=7.7 Hz, 4.2 Hz, 2H), 5.18 (s, 2H), 4.09 (qd, J=5.6 Hz, 4.9 Hz, 2H), 2.12 (s, 3H), 1.33 (t, J=5.6 Hz, 3H); $^{13}$C NMR (100 MHz, CDCl$_3$) δ: 170.5, 158.6 (d, J=4 Hz), 156.0 (d, J=149 Hz), 134.3 (d, J=25 Hz), 132.9 (d, J=5 Hz), 132.7 (d, J=10 Hz), 130.5 (d, J=23 Hz), 129.5 (d, J=139 Hz), 128.6 (d, J=13 Hz), 126.6 (d, J=3 Hz), 66.0, 62.2 (d, J=6 Hz), 21.0, 16.7; $^{31}$P NMR (162 MHz, CDCl$_3$) δ: +25.0. HMRS (ESI) calculated for C$_{16}$H$_{18}$O$_4$BrNP [M+H$^+$], m/z 398.0151. found: 398.0157.

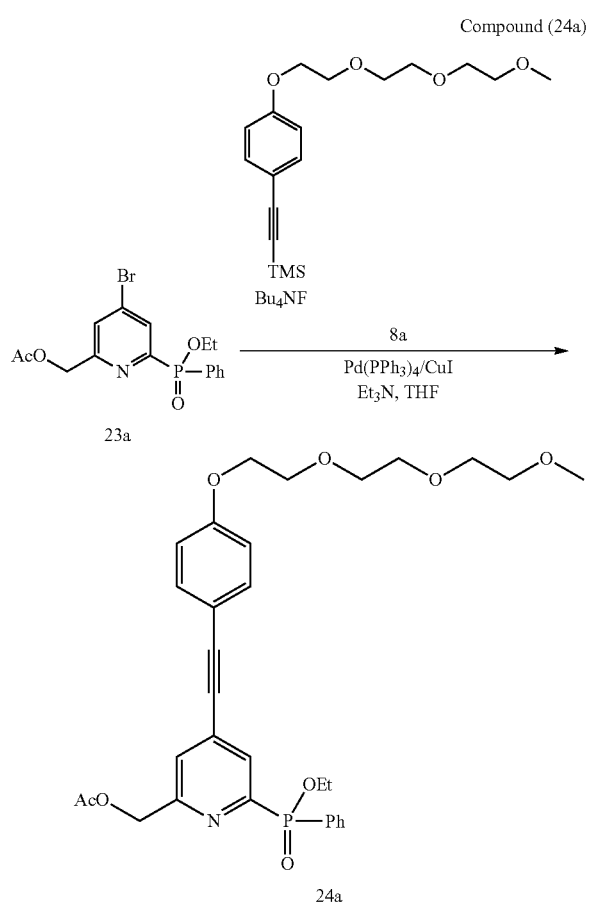

Compound (24a)

23a

24a

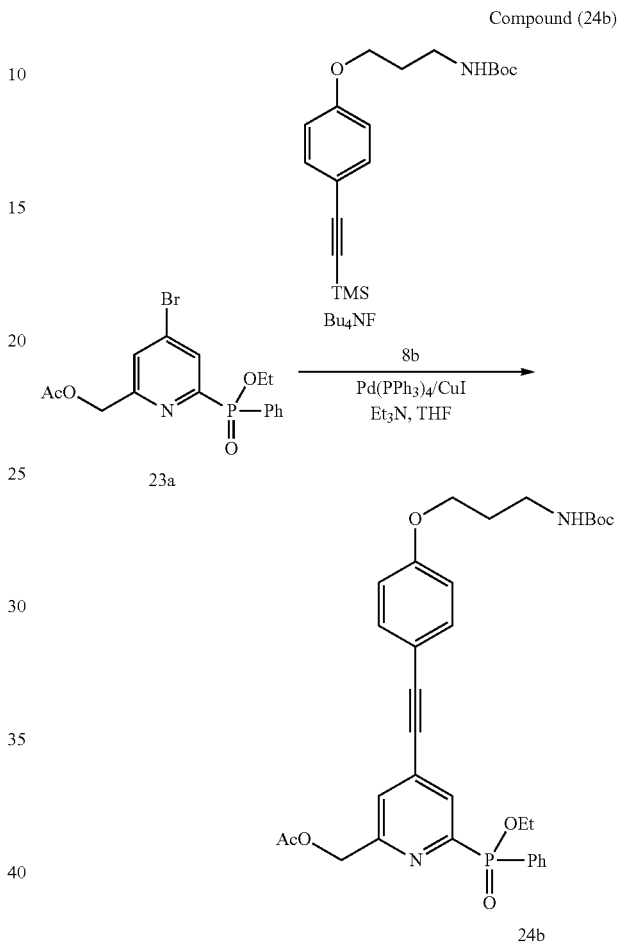

Compound (24b)

23a

24b

Anhydrous tetrahydrofuran (8 mL) was added to the bromo derivative 23a (540 mg, 1.36 mmol) and the solution was degassed via three freezing-thawing cycles. Acetylenic derivative 8a (456 mg, 1.36 mmol) was added to this solution, followed by addition of triethylamine (4 mL), and the solution was degassed again. Tetrakis(triphenylphosphine)palladium(0) (156 mg, 0.136 mmol) and copper iodide (26 mg, 0.136 mmol) were added to this solution. This new solution was degassed again three times and was then stirred under argon, and, immediately after, a tetrabutylammonium fluoride solution (1 M in tetrahydrofuran, 1.9 mL, 2.04 mmol) was added to this mixture. A color change from yellow to dark blue was observed, and the mixture was stirred at 65° C. under argon. The reaction progress was monitored by TLC. After 3 hours, the reaction was complete. The reaction mixture was cooled, the solvent was removed under reduced pressure and the crude product was purified by chromatography on a column of silica (dichloromethane/methanol 0 to 1.5% in 0.1% increments) to give a yellow oil corresponding to compound 24a (575 mg, 73%). $^1$H NMR (400 MHz, CDCl$_3$) δ: 8.05 (dd, J=6.0 Hz, 1.6 Hz, 1H), 7.96 (dd, J=8.4 Hz, 12.4 Hz, 2H), 7.50 (t, J=8.4 Hz, 1H), 7.44 (d, J=8.8 Hz, 2H), 7.43 (2H, td, J=8.4 Hz, 4.2 Hz, 2H), 7.42 (d, J=1.6 Hz, 1H), 6.88 (d, J=8.8 Hz, 2H), 5.21 (s, 2H), 4.12 (qd, J=5.6 Hz, 4.8 Hz, 2H), 4.11 (t, J=4.8 Hz, 2H), 3.83 (t, J=4.8 Hz, 2H), 3.71 (t, J=4.8 Hz, 2H), 3.65 (t, J=4.8 Hz, 2H), 3.63 (t, J=4.8 Hz, 2H), 3.61 (t, J=4.8 Hz, 2H), 3.34 (s, 3H), 2.13 (s, 3H), 1.34 (t, J=5.6 Hz, 3H); $^{13}$C NMR (100 MHz, CDCl$_3$) δ: 170.6; 160.1; 157.3 (d, J=20 Hz); 154.7 (d, J=165 Hz); 133.8; 133.2 (d, J=12 Hz), 132.7 (d, J=5 Hz); 132.6 (d, J=10 Hz), 130.1 (d, J=139 Hz); 128.8 (d, J=22 Hz), 128.6 (d, J=12 Hz), 124.6 (d, J=3 Hz), 115.1; 114.1; 96.2; 85.5 (d, J=2 Hz), 72.2; 71.1; 70.9; 70.8; 69.8; 67.8; 66.5; 62.1 (d, J=6 Hz), 59.3; 21.1; 16.7; $^{31}$P NMR (162 MHz, CDCl$_3$) δ:+26.0. HMRS (ESI) calculated for $C_{31}H_{37}O_8NP$ [M+H$^+$], m/z 582.2257. found: 582.2260.

Anhydrous tetrahydrofuran (3 mL) was added to the bromo derivative 23a (170 mg, 0.43 mmol) and the solution was degassed via three freezing-thawing cycles. Acetylenic derivative 8b (148 mg, 0.43 mmol) and triethylamine (1.5 mL) were added to this solution and the solution was degassed again. Tetrakis(triphenylphosphine)palladium(0) (49 mg, 0.043 mmol) and copper iodide (8 mg, 0.043 mmol) were added to this solution. This new solution was degassed again three times and was then stirred under argon, and, immediately after, a tetrabutylammonium fluoride solution (1 M in THF, 0.6 mL, 0.64 mmol) was added to this mixture. A color change from yellow to dark blue was observed, and the mixture was stirred at 65° C. under argon. The reaction progress was monitored by TLC. After 3 hours, the reaction was complete. The reaction mixture was cooled to room temperature and the solvent was removed under reduced pressure. The crude product was purified by chromatography on a column of silica (dichloromethane/methanol 0 to 1.5% in 0.1% increments) to give a yellow oil corresponding to compound 24b (174 mg, 69%); $^1$H NMR (400 MHz, CDCl$_3$) δ: 8.09 (dd, J=6.0 Hz, 2.0 Hz, 1H), 7.99 (dd, J=8.4 Hz J=12.4 Hz, 2H), 7.54 (t, J=8.4 Hz, 1H), 7.47 (d, J=8.4 Hz, 2H), 7.45 (td, J=8.4 Hz, 4.2 Hz, 2H), 7.45 (d, J=2.0 Hz, 1H), 6.88 (d, J=8.4 Hz, 2H), 5.24 (s, 2H), 4.75 (se, 1H), 4.14 (qd, J=5.6 Hz; 4.8 Hz, 2H), 4.05 (t, J=6 Hz, 2H), 3.33 (m, 2H), 2.17 (s, 3H), 1.92 (q, J=6 Hz, 2H), 1.44 (s, 9H), 1.38 (t, J=5.6 Hz, 3H); $^{13}$C NMR (100 MHz, CDCl$_3$) δ: 170.7; 160.0; 157.3 (d, J=20.3 Hz), 156.2; 154.6 (d, J=167 Hz), 133.9; 133.2 (d, J=12 Hz), 132.7 (d, J=5 Hz), 132.6 (d, J=10 Hz), 130.1 (d, J=138 Hz), 129.1 (d, J=23 Hz), 128.6 (d, J=13 Hz), 124.6 (d, J=3 Hz), 114.9; 114.1; 96.2; 85.5 (d, J=2 Hz), 79.5; 66.5; 66.1; 62.1 (d, J=6 Hz), 38.1; 29.7; 28.6; 21.1; 16.7; $^{31}$P NMR (162 MHz, CDCl$_3$) δ: +26.1. HMRS (ESI) calculated for C$_{32}$H$_{38}$O$_7$N$_2$P [M+H$^+$], m/z 593.2417 found: 593.2435.

Compounds (24c), (24d), (24e), (24f)

These compounds were obtained according to the procedure used for compounds 24a and 24b.

Hz), 4.75 (s, 2H), 4.14 (qd, J=5.6 Hz 4.8 Hz, 2H), 4.11 (t, J=4.8 Hz, 2H), 3.86 (t, J=4.8 Hz, 2H), 3.73 (t, J=4.8 Hz, 2H), 3.68 (t, J=4.8 Hz, 2H), 3.66 (t, J=4.8 Hz, 2H), 3.63 (t, J=4.8 Hz, 2H), 3.37 (s, 3H), 1.37 (t, J=5.6 Hz, 3H); $^{13}$C NMR (100 MHz, CDCl$_3$) δ: 160.4 (d, J=19 Hz), 159.9; 154.0 (d, J=165 Hz), 133.6, 133.0 (d, J=12 Hz), 132.6 (d, J=5 Hz), 132.3 (d, J=10 Hz), 129.7 (d, J=128 Hz), 128.6 (d, J=22 Hz), 128.4 (d, J=12 Hz), 123.8 (d, J=3 Hz), 114.9, 113.8, 96.0, 85.3 (d, J=2 Hz), 71.9, 70.9, 70.7, 70.6, 69.6, 67.5, 63.9, 61.8 (d, J=6 Hz), 59.1, 16.5; $^{31}$P NMR (162 MHz, CDCl$_3$) δ: +26.6. HMRS (ESI) calculated for C$_{24}$H$_{29}$NO$_9$S [M+H$^+$], m/z 540.2151 found: 540.2142.

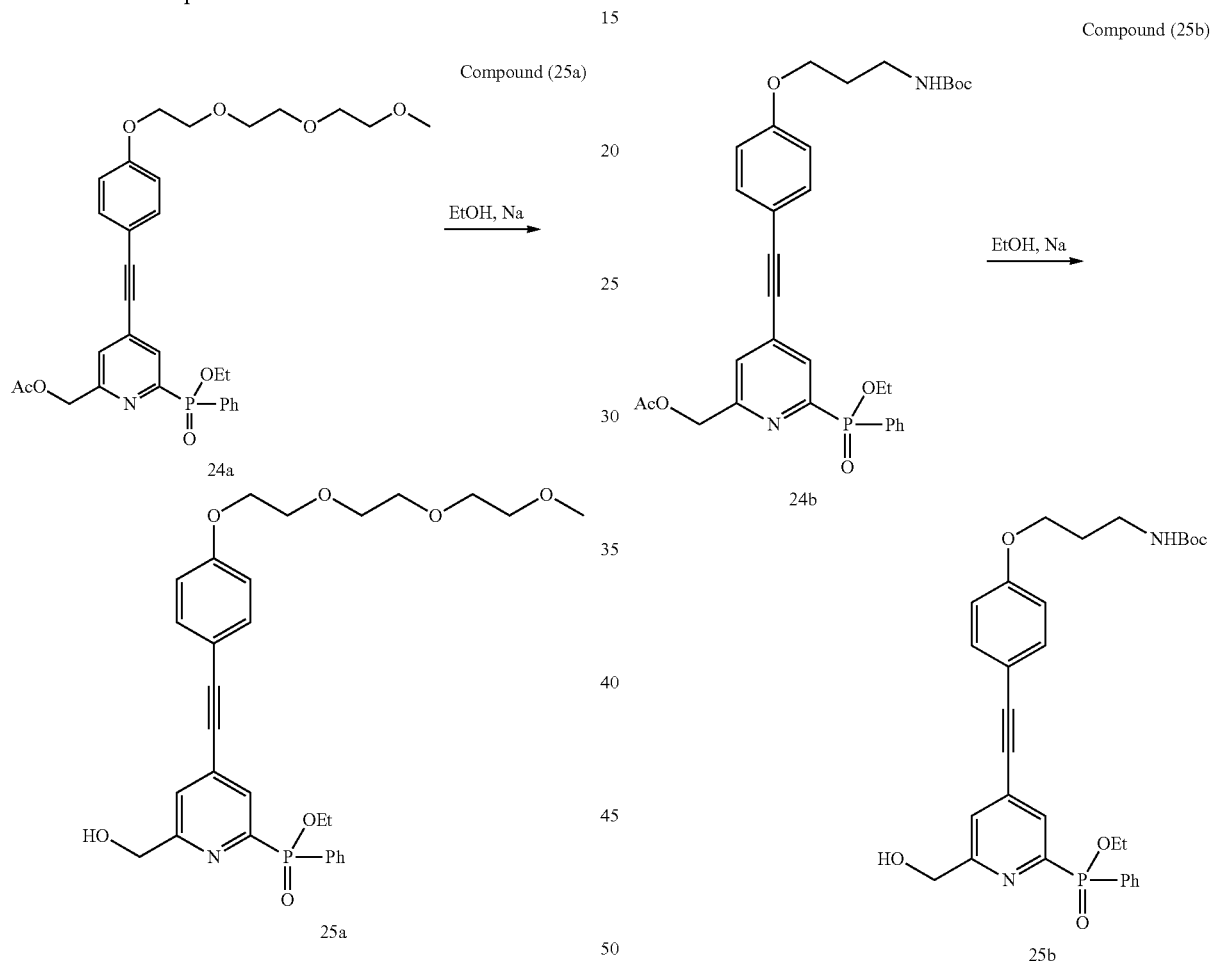

A catalytic amount of sodium metal (~2 mg) was added to a solution of the acetyl derivative 24a (50 mg, 0.086 mmol) in absolute ethanol (2.5 mL), and the solution was heated with stirring for 40 minutes under an inert atmosphere. The reaction progress was monitored by TLC. After this period, the reaction was complete. Dichloromethane (25 mL) was added to this mixture and the sodium salts were then filtered off on silica. The silica was rinsed with dichloromethane/10% ethanol (300 mL). The solvent was removed under reduced pressure and the crude product was purified by chromatography on a column of silica (dichloromethane/methanol 0 to 2.4% in 0.2% increments) to give a colorless oil corresponding to compound 25a (40 mg, 87%). $^1$H NMR (400 MHz, CDCl$_3$) δ: 8.06 (dd, J=6.0 Hz, 1.6 Hz, 1H), 7.95 (dd, J=8.4 Hz; 12.4 Hz, 2H), 7.53 (t, J=8.4 Hz, 1H), 7.44 (d, J=8.8 Hz, 2H), 7.43 (td, J=8.4 Hz; 4.2 Hz, 2H), 7.39 (d, J=1.6 Hz, 1H), 6.90 (d, J=8.8

A catalytic amount of sodium metal (~2 mg) was added to a solution of the acetyl derivative 24b (32 mg, 0.054 mmol) in absolute ethanol (2.5 mL), and the solution was heated with stirring for 40 minutes under an inert atmosphere. The reaction progress was monitored by TLC. After this period, the reaction was complete. Dichloromethane (25 mL) was added to this mixture and the sodium salts were then filtered off on silica. The silica was rinsed with dichloromethane/10% ethanol (300 mL). The solvent was removed under reduced pressure and the crude product was purified by chromatography on a column of silica (dichloromethane/methanol, 0 to 2% in 0.2% increments) to give a colorless oil corresponding to compound 25b (24 mg, 80%). $^1$H NMR (400 MHz, CDCl$_3$) δ: 8.01 (dd, J=6.4 Hz, 2.0 Hz, 1H), 7.89 (dd, J=8.4 Hz, 12.4 Hz, 2H), 7.48 (t, J=8.4 Hz, 1H), 7.40 (d, J=8.8 Hz, 2H), 7.39 (td, J=8.4 Hz, 4.2 Hz, 2H), 7.33 (d, J=2.0 Hz, 1H), 6.81 (d, J=8.8 Hz, 2H), 4.73 (s, 1H), 4.69 (s, 2H), 4.08 (qd, J=5.6 Hz, 4.8 Hz, 2H), 3.97 (t, J=6 Hz, 2H), 3.26 (m, 2H), 1.92 (q, J=6 Hz, 2H), 1.37 (s, 9H), 1.31 (t, J=5.6 Hz, 3H); $^{13}$C NMR (100 MHz, CDCl$_3$) δ: 160.3 (d, J=18 Hz), 159.8; 156.0; 153.2 (d, J=164 Hz); 133.7; 133.0 (d, J=11 Hz); 132.6 (d, J=5 Hz); 132.3 (d, J=10 Hz); 129.6 (d, J=138 Hz); 128.6 (d, J=18 Hz); 128.5 (d, J=9 Hz); 123.8 (d, J=3 Hz); 114.7; 113.8; 96.0; 85.3 (d, J=2 Hz); 79.3; 65.9; 63.8; 61.9 (d, J=6 Hz); 37.9; 29.5; 28.4; 16.6; $^{31}$P NMR (162 MHz, CDCl$_3$) δ: +25.6. HMRS (ESI) calculated for C$_{30}$H$_{36}$O$_6$N$_2$P [M+H$^+$], m/z 551.2311 found: 551.2290.

Compounds (25c), (25d), (25e), (25f)

These compounds were obtained according to the procedure used for examples 25a and 25b.

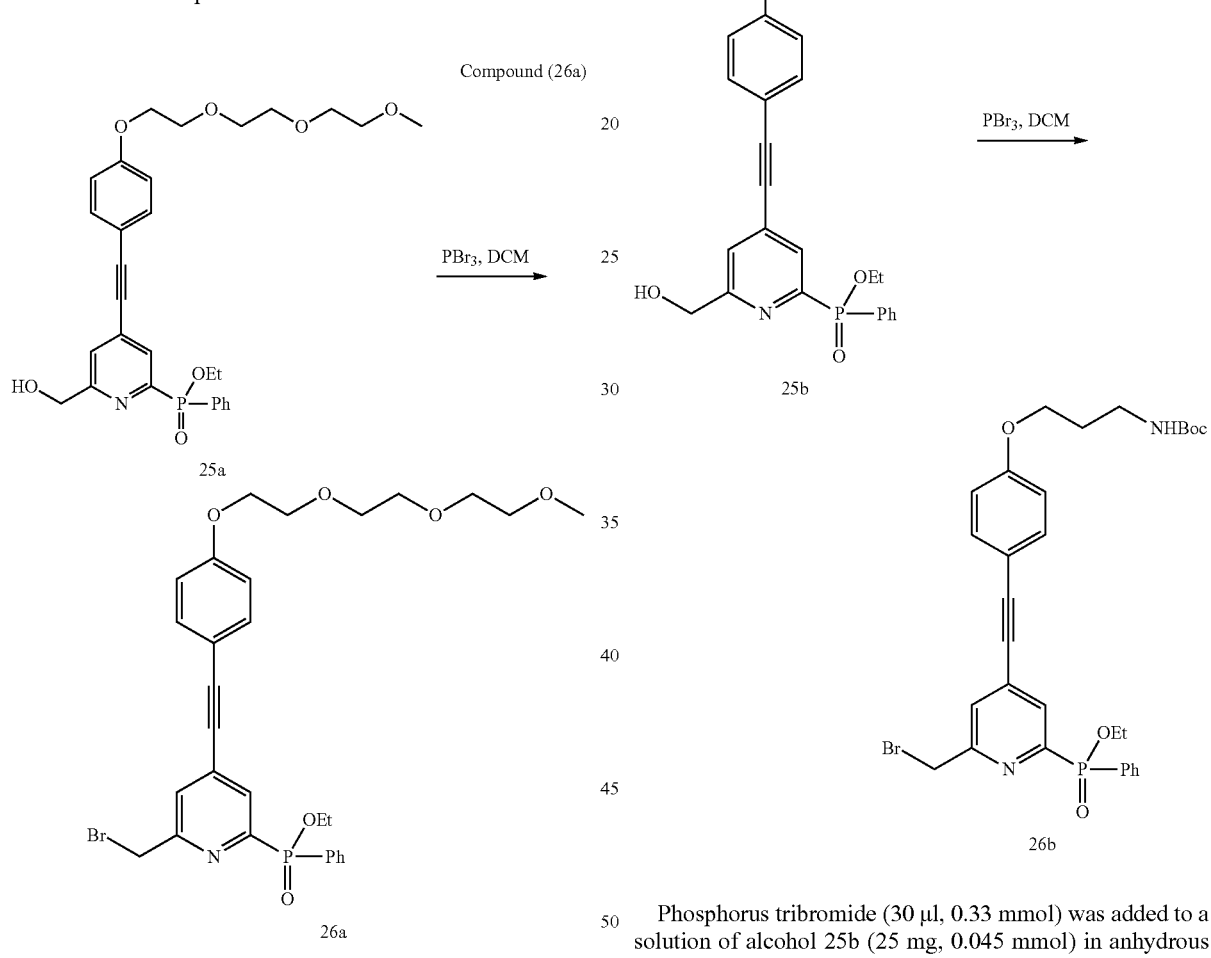

Compound (26a)

Compound (26b)

Phosphorus tribromide (30 µl, 0.33 mmol) was added to a solution of the alcohol 25a (116 mg, 0.22 mmol) in anhydrous dichloromethane (5 mL) cooled to 0° C. The solution was stirred for 1 hour at 0° C. and then allowed to warm to room temperature. The reaction progress was monitored by TLC. After 1 hour, the reaction was complete. The reaction mixture was immediately purified by chromatography on a column of silica (dichloromethane/1% methanol) to give the desired compound 26a in the form of a yellow oil (95 mg, 73%); $^1$H NMR (400 MHz, CDCl$_3$) δ: 8.00 (dd, J=6.0 Hz, 1.2 Hz, 1H), 7.94 (dd, J=8.8 Hz, 12.4 Hz, 2H), 7.51 (d, J=1.2 Hz, 1H), 7.48 (t, J=8.8 Hz, 1H), 7.41 (d, J=8.8 Hz, 2H), 7.40 (td, J=8.8 Hz, 4.2 Hz, 2H), 6.85 (d, J=8.8 Hz, 2H), 4.48 (s, 2H), 4.09 (qd, J=7.2 Hz, 4.8 Hz, 2H), 4.08 (t, J=4.8 Hz, 2H), 3.81 (t, J=4.8 Hz, 2H), 3.67 (t, J=4.8 Hz, 2H), 3.63 (t, J=4.8 Hz, 2H), 3.59 (t, J=4.8 Hz, 2H), 3.49 (t, J=4.8 Hz), 3.31 (s, 3H), 1.32 (t, J=7.2 Hz, 3H); $^{13}$C NMR (100 MHz, CDCl$_3$) δ: 160.1 (d, J=19 Hz); 159.9; 154.3 (d, J=165 Hz); 133.6; 133.3 (d, J=12 Hz); 132.4 (d, J=5 Hz); 132.3 (d, J=10 Hz); 129.7 (d, J=128 Hz); 128.6 (d, J=22 Hz); 128.4 (d, J=13H); 126.7 (d, J=3 Hz); 114.9; 113.8; 96.3; 84.9 (d, J=2 Hz); 71.9; 70.9; 70.7; 70.6; 69.6; 67.5; 61.0 (d, J=5 Hz); 59.1; 33.1; 16.6; $^{31}$P NMR (162 MHz, CDCl$_3$) δ: +24.8; HMRS (ESI) calculated for C$_{29}$H$_{34}$O$_6$NPBr [M+H$^+$], m/z 602.1302. found: 602.1302.

Phosphorus tribromide (30 µl, 0.33 mmol) was added to a solution of alcohol 25b (25 mg, 0.045 mmol) in anhydrous dichloromethane (3 mL) cooled to 0° C. The solution was stirred for 45 minutes at 0° C. and then allowed to warm to room temperature. The reaction progress was monitored by TLC. After 30 minutes, the reaction was complete. The reaction mixture was immediately purified by chromatography on a column of silica (dichloromethane/1% methanol) to give the desired compound 26b in the form of a yellow oil (13 mg, 47%); $^1$H NMR (400 MHz, CDCl$_3$) δ: 8.07 (dd, J=6.0 Hz, 1.2 Hz, 1H), 8.01 (dd, J=8.4 Hz J=12 Hz, 2H), 7.58 (d, J=1.2 Hz, 1H), 7.55 (t, J=8.4 Hz, 1H), 7.47 (td, J=8.4 Hz, 4.2 Hz, 2H), 7.46 (d, J=8.8 Hz, 2H), 6.89 (d, J=8.8 Hz, 2H), 4.72 (s, 1H), 4.55 (s, 2H), 4.15 (qd, J=6.0 Hz, 4.8 Hz, 2H), 4.05 (t, J=6 Hz, 2H), 3.33 (m, 2H), 2.00 (q, J=6 Hz, 2H), 1.44 (s, 9H), 1.38 (t, J=6.0 Hz, 3H); $^{31}$P NMR (162 MHz, CDCl$_3$) δ:+25.8. HMRS (ESI) calculated for C$_{30}$H$_{34}$O$_5$N$_2$PBr [M+H$^+$], m/z 613.1462. found: 613.1462.

Compound (26g)

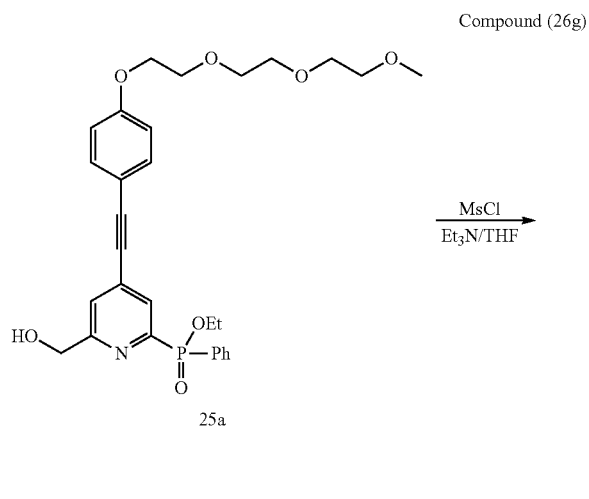

Compound (26h)

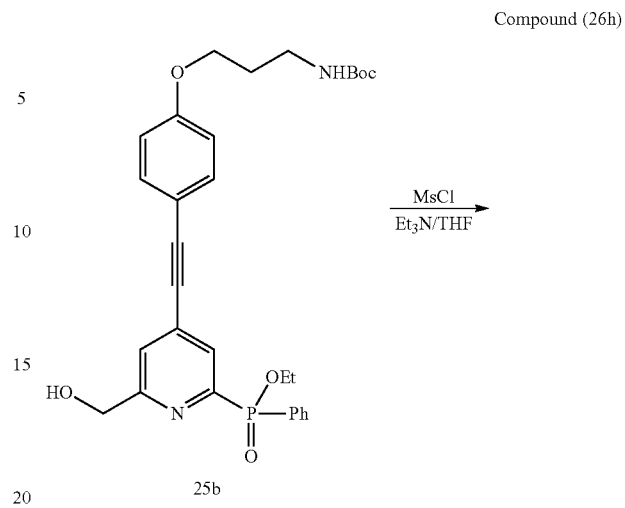

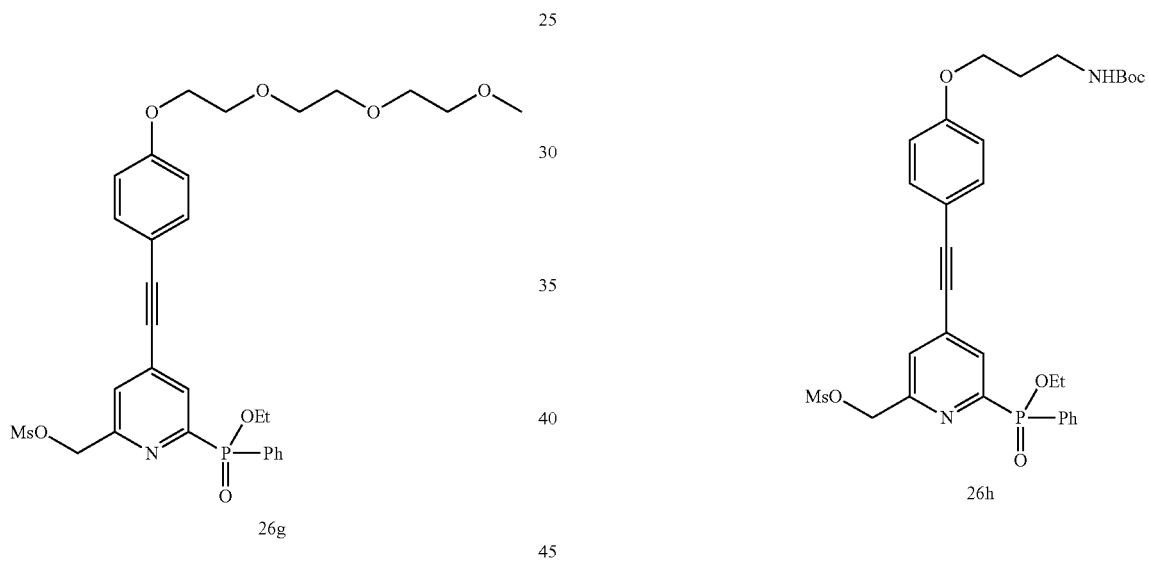

Triethylamine (0.3 mL, 1.98 mmol) was added to a solution of alcohol 25a (360 mg 0.66 mmol) in anhydrous tetrahydrofuran (4 mL), cooled to 5° C., followed by addition of mesyl chloride (77 µL, 0.99 mmol), under an inert atmosphere. The reaction medium as stirred at room temperature for 15 minutes. The reaction progress was monitored by TLC. After this period, the reaction was complete. The solvent was removed under reduced pressure. Saturated aqueous sodium chloride solution (30 mL) was added to the residue, and the mixture was extracted with dichloromethane (2×30 mL). The organic phases were combined and dried over magnesium sulfate. After filtration, the solvent was removed under reduced pressure to give a yellowish oil corresponding to compound 26g (430 mg, 99%), which was pure enough to be used in the following step without further purification.

Triethylamine (87 µL, 0.64 mmol) was added to a solution of alcohol 25b (118 mg, 0.21 mmol) in anhydrous tetrahydrofuran (7 mL), cooled to 5° C., followed by addition of mesyl chloride (24 µL, 0.32 mmol), under an inert atmosphere. The reaction medium was stirred at room temperature for 15 minutes. The reaction progress was monitored by TLC. After this period, the reaction was complete. The solvent was removed under reduced pressure. Saturated aqueous sodium chloride solution (30 mL) was added to the residue, and the mixture was extracted with dichloromethane (2×30 mL). The organic phases were combined and dried over magnesium sulfate. After filtration, the solvent was removed under reduced pressure to give a brown solid corresponding to compound 26h (125 mg, 95%), which was pure enough to be used in the following step without further purification.

Compounds (26i), (26j), (26k), (26l)

These compounds were obtained according to the procedure used for examples 26g and 26h.

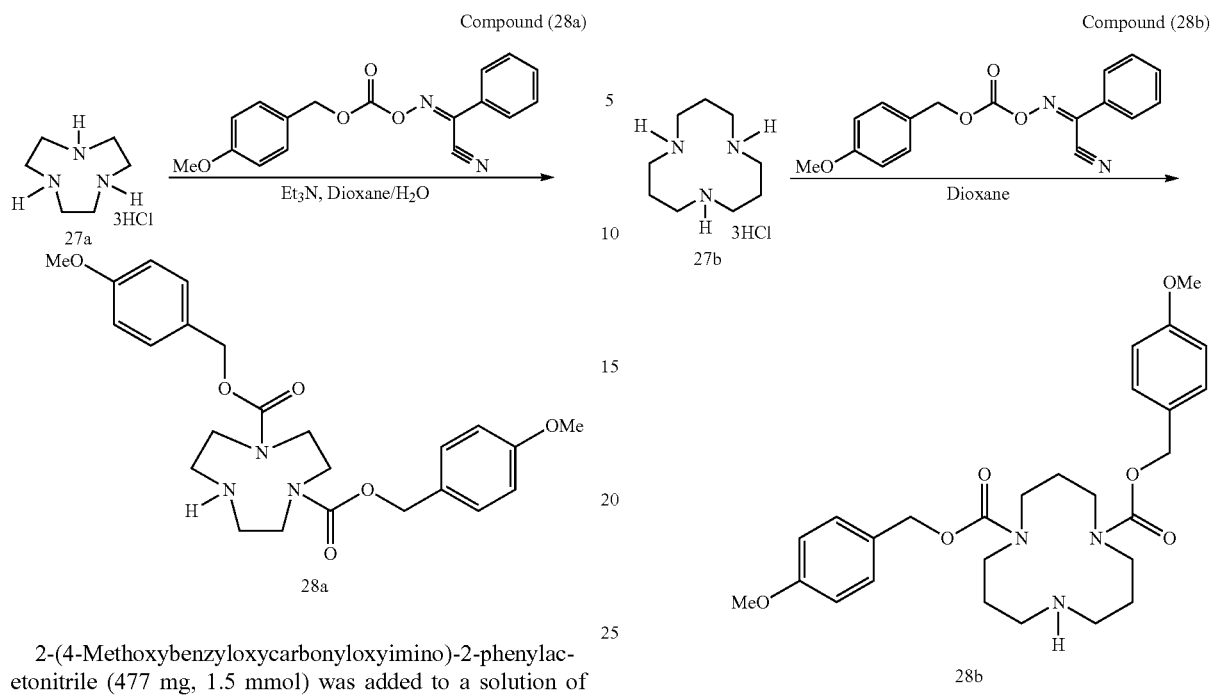

Compound (28a)

Compound (28b)

2-(4-Methoxybenzyloxycarbonyloxyimino)-2-phenylacetonitrile (477 mg, 1.5 mmol) was added to a solution of 1,4,7-triazacyclononane hydrochloride 27a (188 mg, 0.78 mmol) in a dioxane/water mixture (10 mL, 8:2). The reaction mixture was homogenized by vigorous stirring, followed by addition of a solution of triethylamine (540 µL, 3.8 mmol) in a dioxane/water mixture (10 mL, 8:2). The reaction progress was monitored by TLC. After 24 hours, the reaction was complete. The solvent was removed under reduced pressure. The residue was dissolved in dichloromethane. This solution was washed with saturated aqueous sodium chloride solution (3×10 mL). The organic phase was dried over magnesium sulfate, filtered and concentrated under reduced pressure. The crude product was purified by chromatography on a column of alumina (dichloromethane/methanol, 98:2 to 90:10 in 1% increments) to give the desired compound 28a in the form of an oil (266 mg, 74%). $^1$H NMR (400 MHz, CDCl$_3$) δ: 7.32-7.25 (m, 4H), 6.88-6.85 (m, 4H), 5.09 (m, 4H), 3.80 (s, 6H), 3.56-3.47 (m, 4H), 3.31-3.25 (m, 4H), 2.87 (m, 4H). $^{13}$C NMR (100 MHz, CDCl$_3$) δ: 159.68; 156.76; 130.05; 128.92; 114.03; 67.15; 55.41; 52.20; 51.98; 51.26; 50.31; 50.07; 49.19; 48.18; 47.73; 47.66.

2-(4-Methoxybenzyloxycarbonyloxyimino)-2-phenylacetonitrile (3.62 g, 11.7 mmol) was added to a solution of 1,4,7-triazacyclododecane 27b (1 g, 5.84 mmol) in dioxane (50 mL). The reaction mixture was homogenized by vigorous stirring and was then stirred at room temperature under an inert atmosphere for 2 hours. The reaction progress was monitored by TLC. After this period, the reaction was complete. The solvent was removed under reduced pressure. The residue was dissolved in dichloromethane (50 mL). This solution was washed with saturated aqueous sodium chloride solution (2×20 mL). The aqueous phases were combined and extracted with dichloromethane (25 mL). The organic phases were combined, dried over magnesium sulfate, filtered and concentrated under reduced pressure. The crude product was purified by chromatography on a column of alumina (dichloromethane/methanol, 100:0 to 97:3 in 0.5% increments) to give the desired compound 28b in the form of an oil (980 mg, 34%). HMRS (ESI) calculated for C$_{27}$H$_{37}$N$_3$O$_6$ [M+H$^+$], m/z 500.2761. found: 500.2758.

Compound (29a)

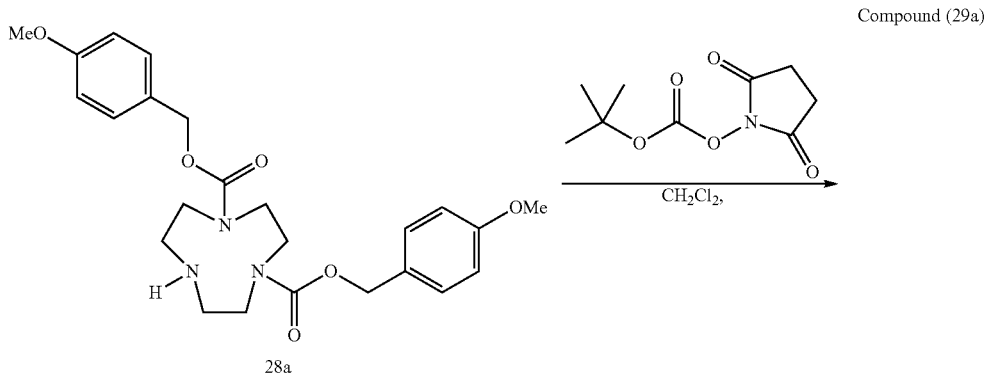

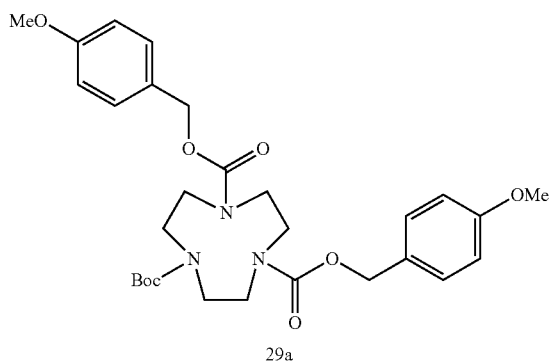

29a

N-(tert-Butoxycarbonyloxy)succinimide (36 mg, 0.15 mmol) was added to a solution of diprotected macrocycle 28a (50 mg, 0.1 mmol) in dichloromethane (7 mL). The solution was stirred at room temperature under an inert atmosphere. The reaction progress was monitored by TLC. After 24 hours, the reaction was complete. The solution was washed directly with saturated aqueous sodium chloride solution (3×10 mL). The organic phase was dried over magnesium sulfate, filtered and concentrated under reduced pressure. The crude product was purified by chromatography on a column of alumina (dichloromethane/methanol 90:10 to 70:30 in 5% increments) to give the desired compound 29a in the form of a brown oil (44 mg, 72%). $^1$H NMR (400 MHz, CDCl$_3$) δ: 7.30-7.19 (m, 4H), 6.88-6.83 (m, 4H), 5.06-4.92 (m, 4H), 3.77 (s, 6H), 3.46-3.39 (m, 12H), 1.55 (s, 9H). $^{13}$C NMR (100 MHz, CDCl$_3$) δ: 159.65; 156.56; 155.76; 130.04; 128.98; 114.00; 80.01; 67.15; 55.38; 49.74; 49.64; 49.47; 49.37; 49.12; 48.92; 48.80; 28.53; 27.75; 25.60. HMRS (ESI) calculated for C$_{29}$H$_{39}$N$_3$O$_8$ [M+H$^+$], m/z 558.2815. found: 558.2808.

Compound (29b)

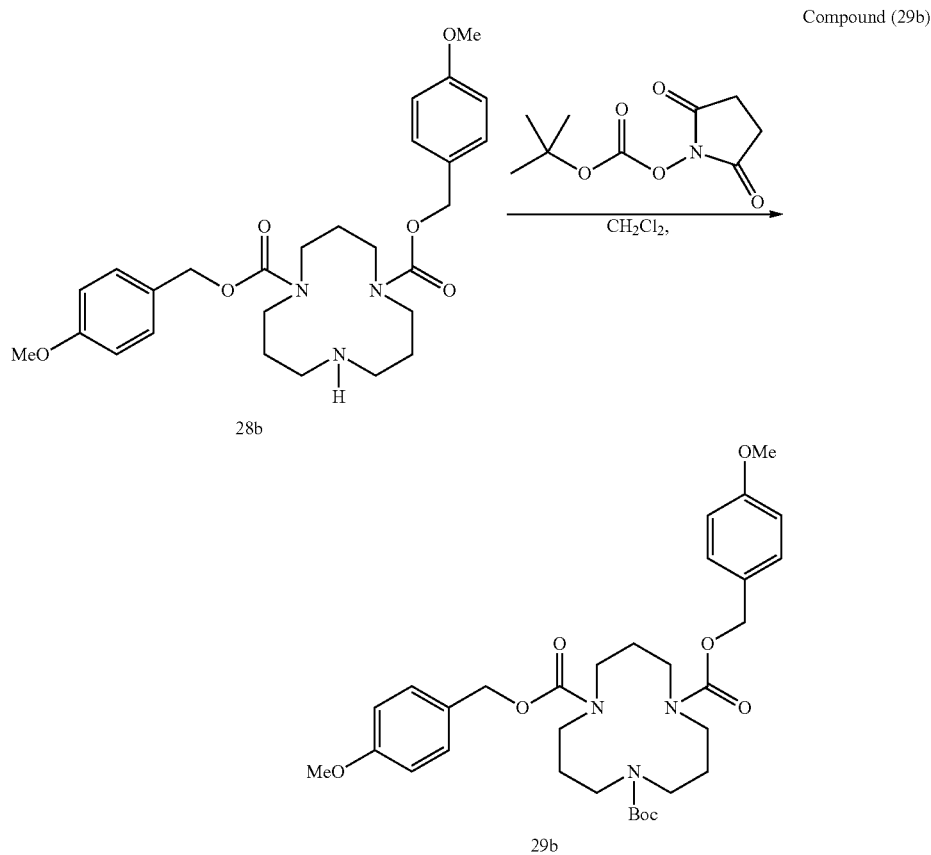

N-(tert-Butoxycarbonyloxy)succinimide (630 mg, 2.93 mmol) was added to a solution of diMOZ macrocycle 28b (980 mg, 1.96 mmol) in dichloromethane (40 mL). The reaction mixture was stirred at room temperature for 24 hours. The reaction progress was monitored by TLC. After this period, the reaction was complete. The solution was washed with saturated aqueous sodium chloride solution (2×20 mL). The aqueous phases were combined and extracted with dichloromethane (2×30 mL). The organic phases were combined, dried over magnesium sulfate, filtered and concentrated under reduced pressure. The crude product was purified by chromatography on a column of alumina (cyclohexane/ ethyl acetate 100:0 to 70:30 in 5% increments) to give the desired compound 29b in the form of an oil (507 mg, 42%).

collected by filtration to give a white solid corresponding to the hydrochloride 30a (102 mg, 62%). m.p.: 172-174° C. $^1$H NMR (500 MHz, D$_2$O) δ: 3.74 (t, J=4.5 Hz, 4H), 3.63 (s, 4H), 3.48 (t, J=4.5 Hz, 4H), 1.47 (s, 9H). $^{13}$C NMR (125 MHz, CDCl$_3$) δ: 136.0; 62.9; 25.9; 22.2; 21.7; 6.7. HMRS (ESI) calculated for C$_{11}$H$_{23}$N$_3$O$_2$ [M+H$^+$], m/z 230.1869. found: 230.1863.

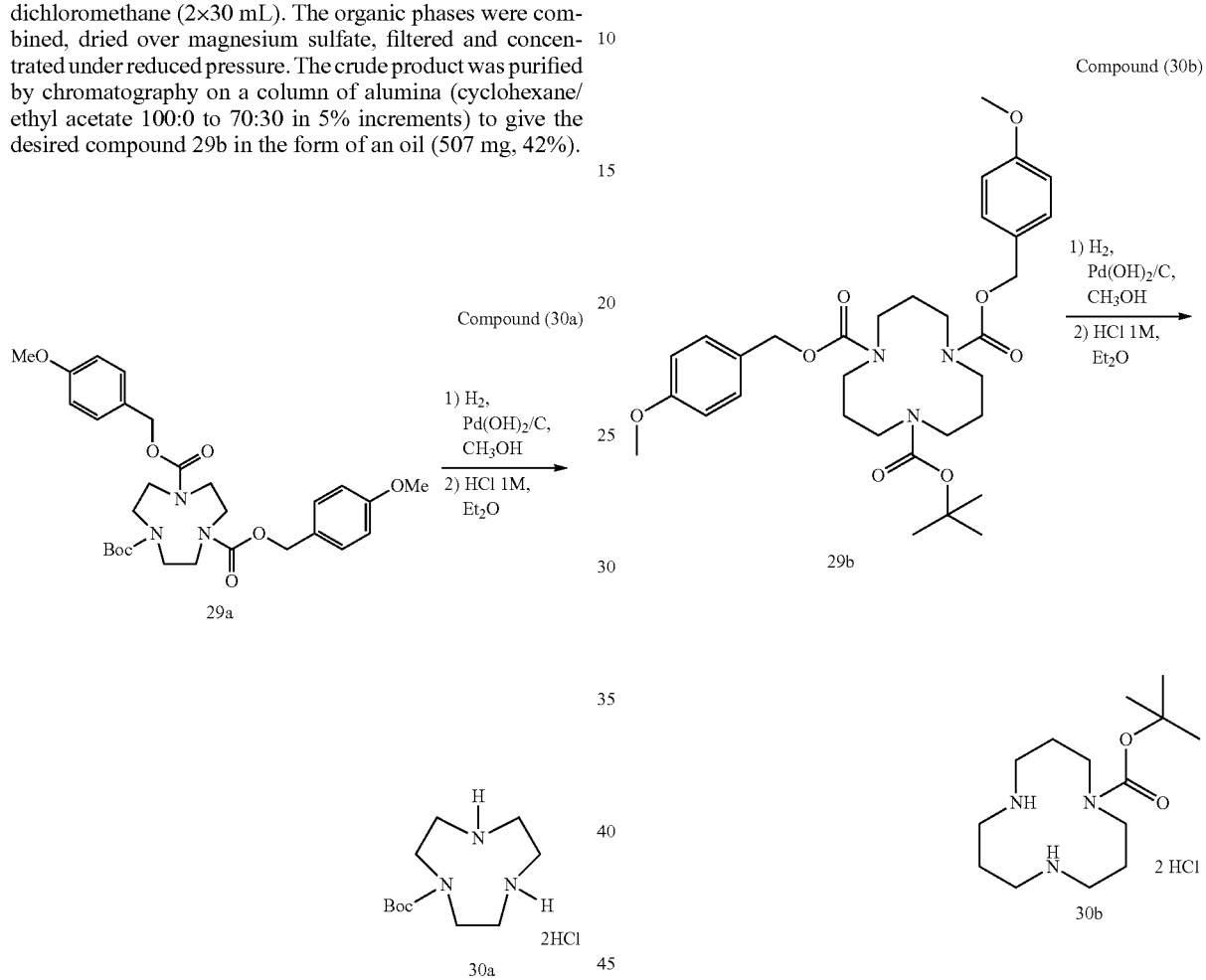

Palladium hydroxide absorbed onto charcoal (about 100 mg) was added to a solution of diMOZ-monoBoc macrocycle 29a (300 mg, 0.5 mmol) in methanol (25 mL). The reaction medium was placed in a hydrogenator and stirred vigorously under a hydrogen atmosphere (3.45 bar-50 psi). The reaction progress was monitored by TLC on alumina. After reaction over night, the reaction was complete. The reaction medium was filtered through Celite and then concentrated under reduced pressure. The colorless oil obtained was dissolved in methanol (3 mL). Aqueous 1M hydrochloric acid solution (pH 2-3) was added to this solution. The mixture was concentrated under reduced pressure and redissolved in a minimum amount of methanol (2 mL). Diethyl ether (35 mL) was added to this solution. The white precipitate obtained was Palladium hydroxide absorbed onto charcoal (about 100 mg) was added to a solution of diMOZ-monoBoc macrocycle 29b (507 mg, 0.846 mmol) in methanol (25 mL). The reaction medium was placed in a hydrogenator and stirred vigorously under a hydrogen atmosphere (3.45 bar-50 psi). The reaction progress was monitored by LC-MS. After reaction over night, the reaction was complete. The reaction medium was filtered through Celite and then concentrated under reduced pressure. The colorless oil obtained was dissolved in methanol (2 mL). Aqueous 1M hydrochloric acid solution (pH 2-3) was added to this solution. The mixture was concentrated under reduced pressure and redissolved in a minimum amount of methanol (1 mL). Diethyl ether (150 mL) was added to this solution. The white precipitate obtained was collected by filtration on a sinter funnel to give a white solid corresponding to the hydrochloride 30b (125 mg, 43%). m.p.: 149-168° C.

Compound (35a)

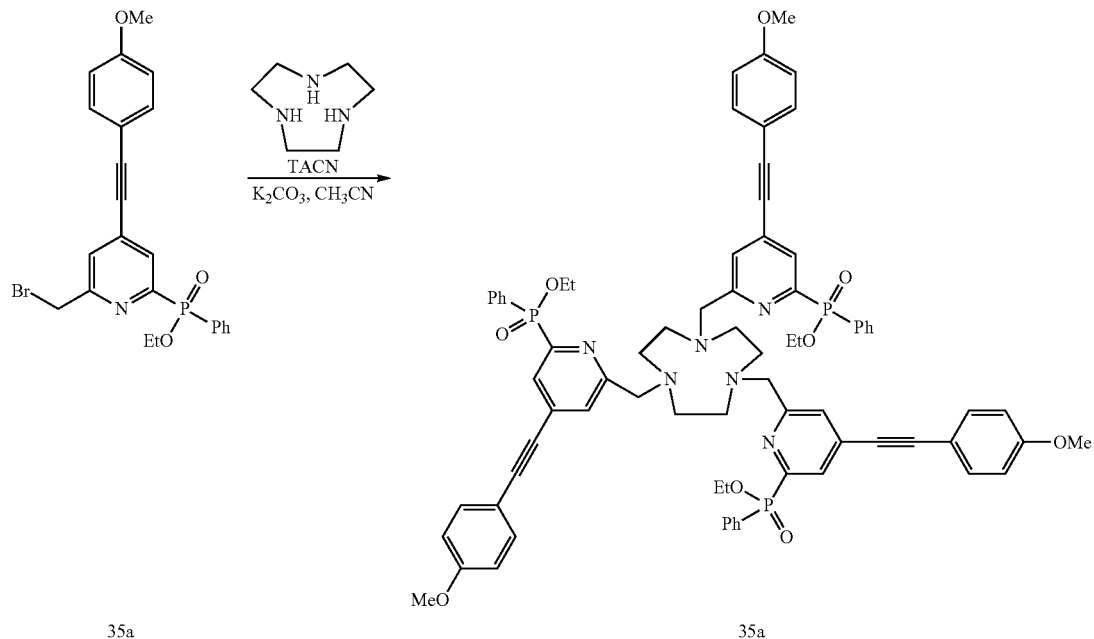

Potassium carbonate (32 mg, 0.234 mmol) and 1,4,7-triazacyclononane (10 mg, 0.078 mmol) were added to a solution of bromo derivative 26c (110 mg, 0.234 mmol) in anhydrous acetonitrile (5 mL) under an inert atmosphere. The reaction medium was refluxed for 16 hours. The reaction progress was monitored by TLC. After this period, the reaction was complete. The reaction medium was cooled to room temperature and the solvent was removed under reduced pressure. Water (10 mL) was added to the residue, and the mixture was extracted with ethyl acetate (2×20 mL). The organic phases were combined and dried over magnesium sulfate. After filtration, the solvent was removed under reduced pressure. The crude product obtained was purified by chromatography on a column of silica (dichloromethane/methanol, 0 to 30% in 1% increments) to give compound 35a in the form of a yellowish oil (23 mg, 23%). $^1$H NMR (400 MHz, CDCl$_3$) δ: 8.03 (dd, J=6.0 Hz, 3H), 7.94 (dd, J=12.4 Hz, J=6.8 Hz, 6H), 7.58 (s, 3H), 7.45 (d, J=8.8 Hz, 6H), 7.42 (t, J=6.8 Hz, 3H), 7.37 (td, J=6.8 Hz J=3.6 Hz, 6H), 6.87 (d, J=8.8 Hz, 6H), 4.10 (qd, J=7.2 Hz, J=4.2 Hz, 6H), 3.83 (s, 6H), 3.82 (s, 9H), 2.74 (s, 12H), 1.33 (t, J=7.2 Hz, 9H); $^{31}$P NMR (162 MHz, CDCl$_3$) δ: +26.6; HMRS (ESI) calculated for C$_{75}$H$_{76}$N$_6$O$_9$P$_3$ [M+H$^+$], m/z 1297.4860. found: 1297.4860.

Compounds (35b) and (35c)

These compounds were obtained according to the procedure used for example 35a.

Compound (37a)

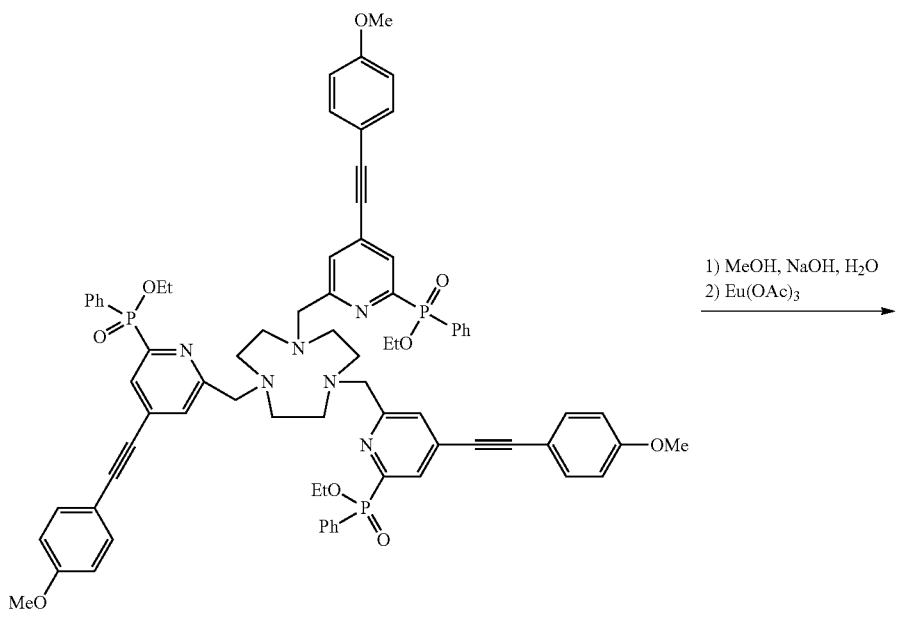

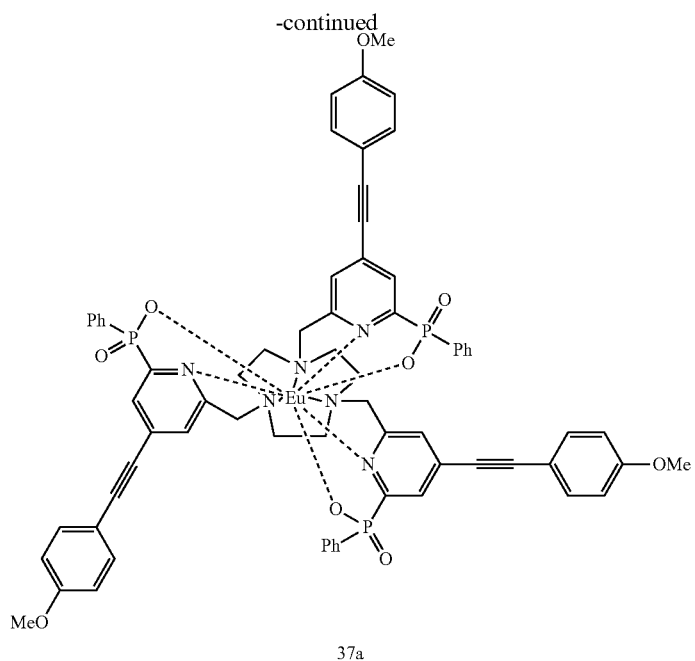

37a

Aqueous sodium hydroxide solution (1 mL, 0.1 M) was added to a solution of the ligand 35a (10 mg, 7.7 μmol) in methanol (3 mL). The solution was heated at 60° C. for 16 hours. The reaction progress was monitored by $^1$H NMR. After this period, the reaction was complete. The pH of the solution was adjusted to 7 by adding hydrochloric acid (1M). Europium acetate (3.4 mg, 8.5 μmol) predissolved in an $H_2O$:$CH_3OH$ solution (0.5 mL, 1:1 v/v) was added to this solution. The reaction mixture was heated at 50° C. for 24 hours. The reaction mixture was cooled to room temperature, the solvent was removed under reduced pressure and the crude product was purified by chromatography on a column of silica (dichloromethane/5% methanol) to give the desired compound 37a in the form of a white solid (2.5 mg, 24%). $^{31}$P NMR (162 MHz, $CDCl_3$) δ: +17.5. HMRS (ESI) calculated for $C_{69}H_{61}N_6O_9P_3Eu$ [M+H$^+$], m/z 1361.2910. found: 1361.2830.

Compounds (37b) and (37c)

These compounds were obtained according to the procedure used for example 37a.

Compound (38a)

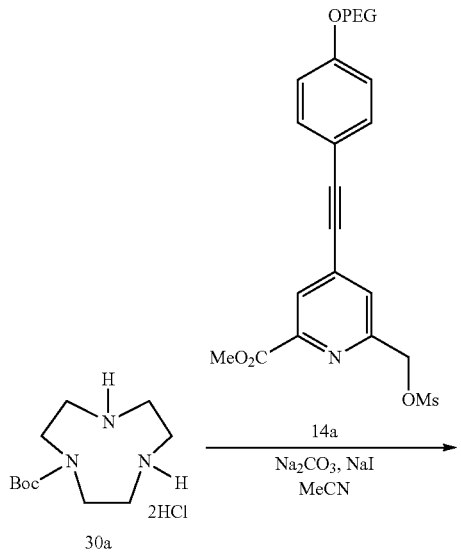

30a

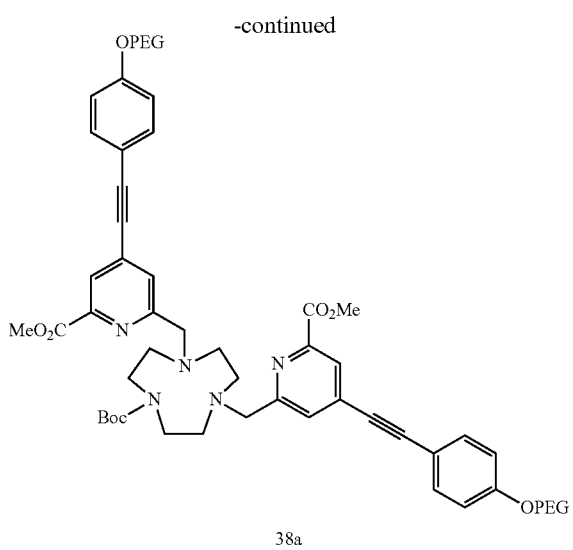

38a

Potassium carbonate (55.5 mg, 0.40 mmol) was added to a solution of TACN monoBoc hydrochloride 30a (20.2 mg, 67 μmol) in anhydrous acetonitrile (20 mL) under an inert atmosphere. A solution of mesyl OPEG chromophore 14a (70 mg, 0.14 mmol) in anhydrous acetonitrile (2 mL) was added to this suspension. The reaction progress was monitored by analytical HPLC. After stirring and heating at 60° C. for 2 hours, the reaction medium was cooled to room temperature. The solvent was removed under reduced pressure. The crude reaction product was purified by chromatography on a column of silica (dichloromethane/methanol, 98:2 to 80:20 in 2% increments) to give compound 38a in the form of an oil (52.8 mg, 75%). HMRS (ESI) calculated for $C_{57}H_{73}N_5O_{14}$ [M+H$^+$], m/z 1052.5232. found: 1052.5256.

Compound (38b)

This compound was obtained according to the procedure used for example in 38a.

Compound (39a)

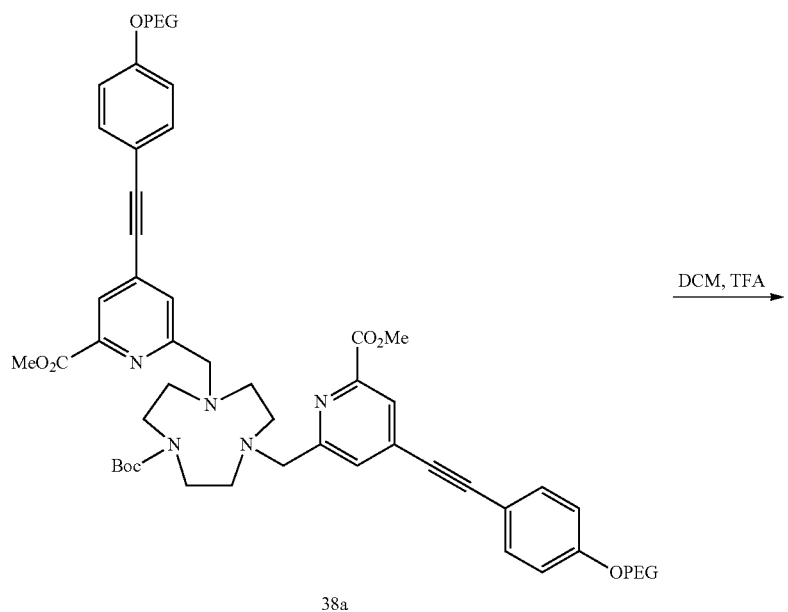

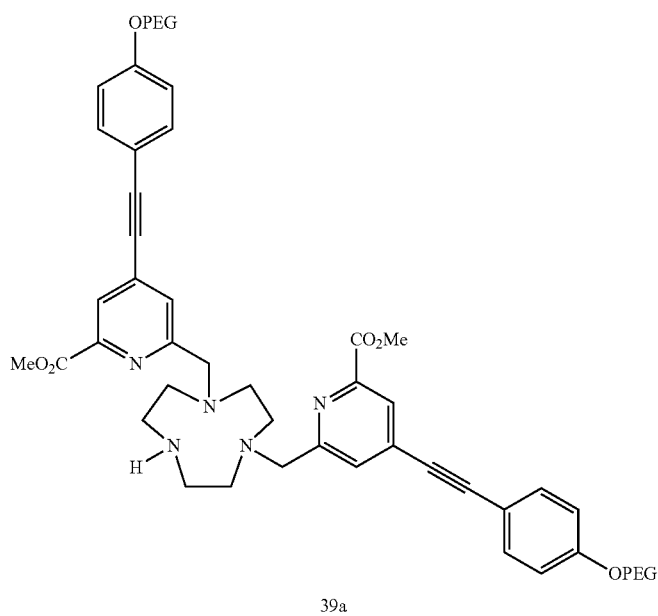

Trifluoroacetic acid (50 µL) was added to a solution of TACN monoBoc-di-arm OPEG 38a (1.47 mg, 1.4 µmol) in dichloromethane (950 µL). The reaction progress was monitored by HPLC. After stirring over night at room temperature, the solvent was removed under reduced pressure. The medium was taken up in methanol (1 mL) and toluene (3 mL) and then evaporated in order to remove the traces of trifluoroacetic acid. The reaction medium was purified by HPLC on a preparative column, to give compound 39a in the form of a yellowish oil (0.75 mg, 56%). HMRS (ESI) calculated for $C_{52}H_{65}N_5O_{12}$ [M+H$^+$], m/z 952.4708. found: 952.4714.

Compound (39b)

This compound was obtained according to the procedure used for example 39a.

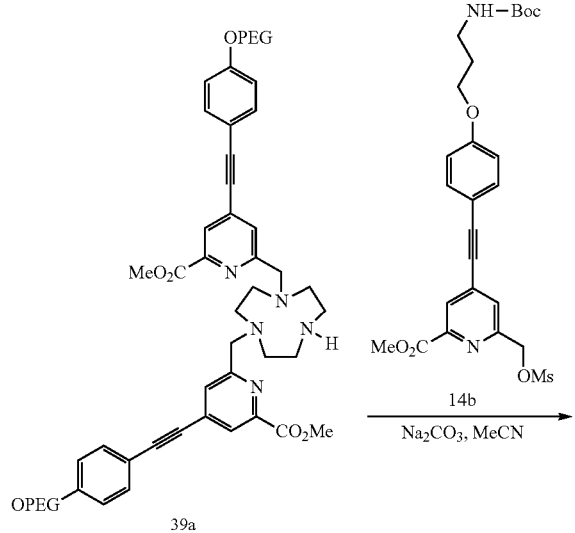

39a

Compound (40)

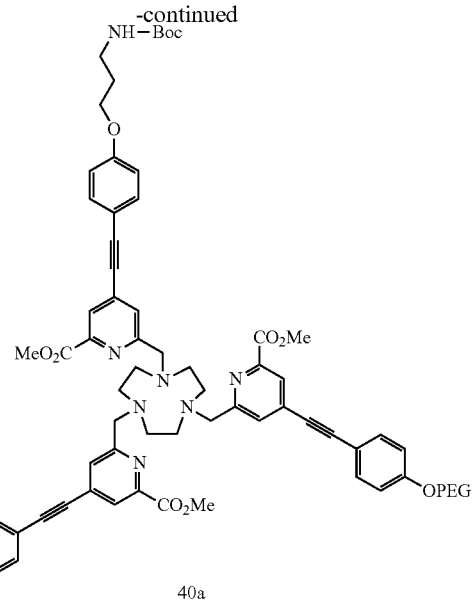

40a

Sodium carbonate (1.4 mg, 1.34 μmol) was added to a solution of TACN di-arm OPEG 39a (4.25 mg, 4.4 μmol) in anhydrous acetonitrile (4 mL) under an inert atmosphere. A solution of mesyl NH-Boc chromophore 14b (3.5 mg, 6.7 μmol) in anhydrous acetonitrile (2 mL) was added to this suspension. The reaction progress was monitored by HPLC. After stirring and heating at 50° C. for 22 hours, the reaction medium was cooled to room temperature. The solvent was removed under reduced pressure. The reaction medium was purified by HPLC on a preparative column. Compound 40a was obtained in the form of a yellowish oil (1.25 mg, 21%).

Compound (41a)

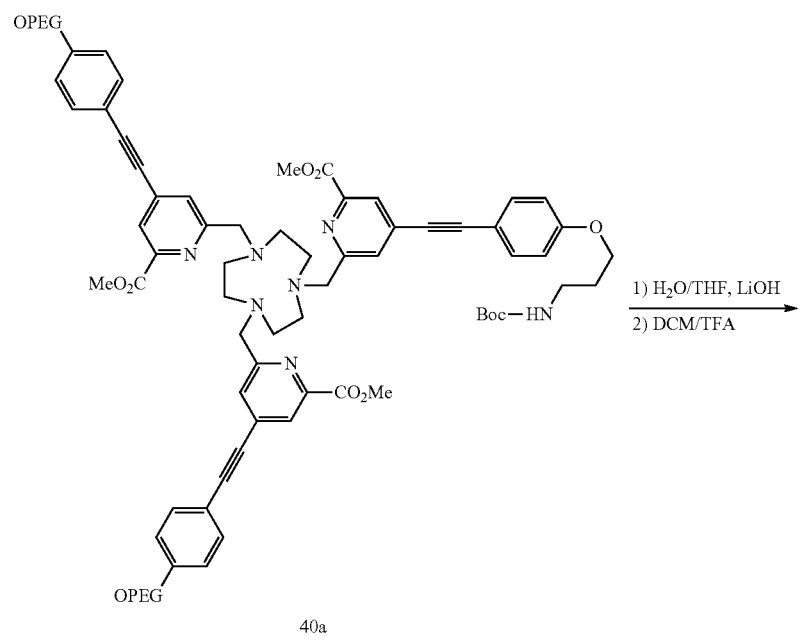

40a

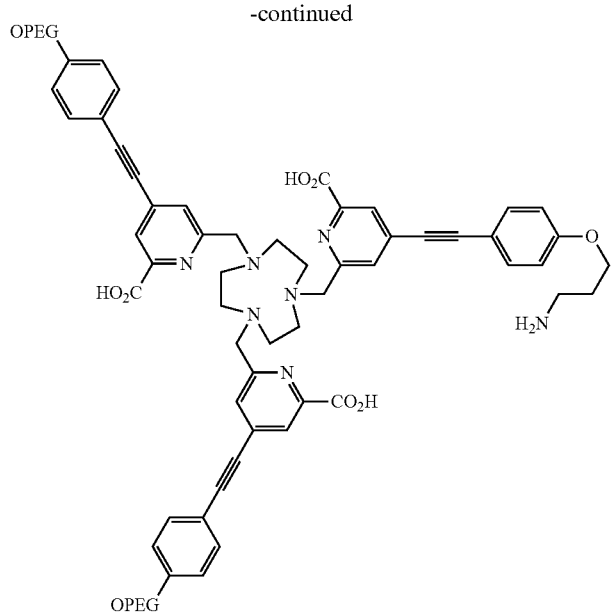

41a

1 M Lithium hydroxide (50 μmol) and pure water (100 μL) were added to a solution of methyl triester ligand 40a (1 mg, 727 nmol) in THF (150 μL). THF (1 ml) was added to this whitish suspension to complete the dissolution. The reaction mixture was stirred at room temperature for 2 hours. The reaction progress was monitored by HPLC. After this period, the reaction was complete. The solvent was removed under reduced pressure. The reaction medium was then taken up in pure water (500 μL) and acidified by addition of aqueous 1M hydrochloric acid solution to obtain a pH of the mixture of between 2-3. The solvent was removed under reduced pressure. The residue was purified by preparative HPLC to give the desired product in the form of an oil (312 nmol, 43%). Trifluoroacetic acid (150 μL) and then a further volume of dichloromethane (2500 μL) were added to the oil obtained previously and of a second batch (1 μmol) in dichloromethane (500 μL). The reaction mixture was stirred at room temperature for 10 minutes. The reaction progress was monitored by HPLC. After this period, the reaction was complete. The solvent was removed under reduced pressure to give compound 41a in the form of an oil (530 nmol, 53%), which was used in the following step without further purification.

Compound (42a)

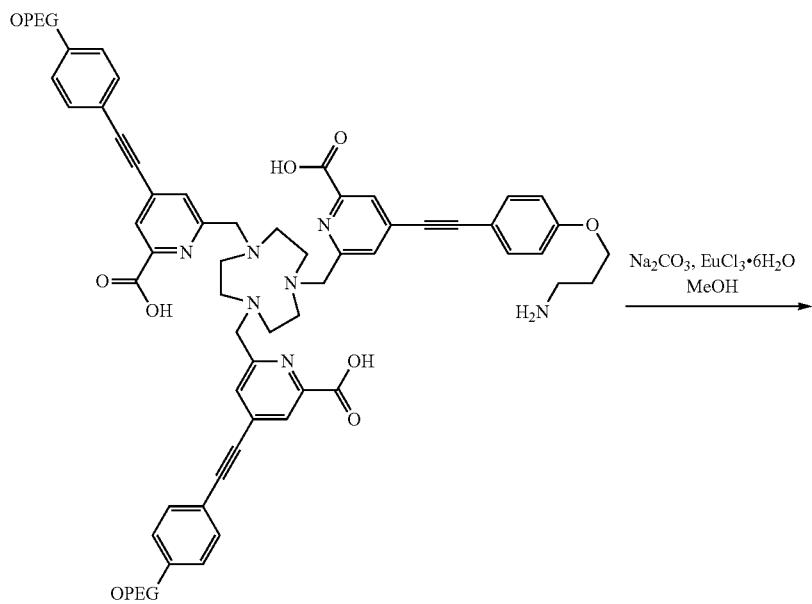

41a

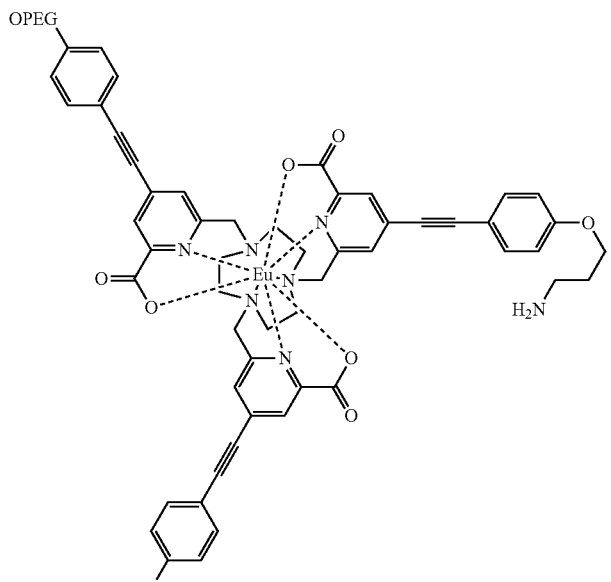

42a

Sodium carbonate (10.4 mg, 98.4 μmol) and europium chloride hexahydrate (16.6 mg, 32.8 μmol) were added to a solution of TACN asymmetric carboxylic acids-NH₂ tri-arm 41a (16.4 μmol) in methanol (5 mL) and water (2 mL). The reaction mixture was heated at 50° C. over night. The reaction progress was monitored by analytical HPLC. After this period, the reaction was complete. The reaction medium was cooled to room temperature and the solvent was then removed under reduced pressure. The residue was purified by preparative HPLC to give the complex 42a in the form of a colorless oil (9.15 μmol, 56%).

Compound (43a)

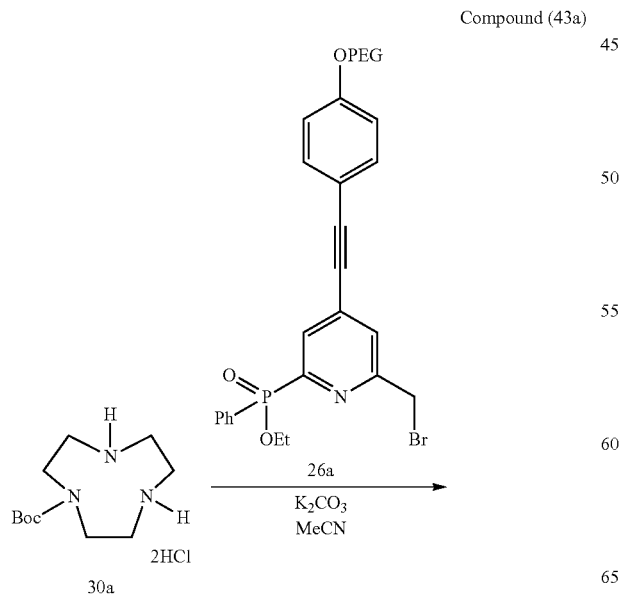

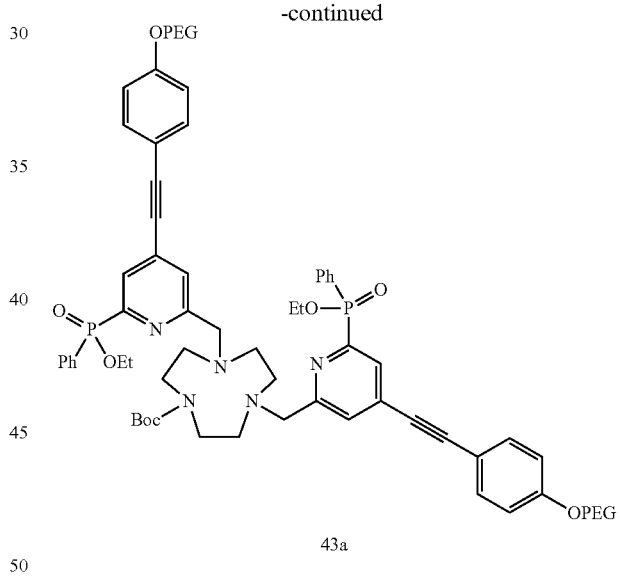

43a

Compound 26a (95 mg, 0.16 mmol) and potassium carbonate (27 mg, 0.19 mmol) were added to a solution of 1,4,7-triazacyclononane-monoBoc 30a (22 mg, 0.096 mmol) in acetonitrile (5 mL). The mixture was stirred under argon at 50° C. for 1 hour. The reaction progress was monitored by TLC. After this period, the reaction was complete. The reaction mixture was cooled to room temperature and the solvent was then removed under reduced pressure. The residue was purified by chromatography on a column of silica (dichloromethane/methanol, 0 to 5% in 0.5% increments) to give the desired compound 43a in the form of a yellow oil (58 mg, 59%): $^1$H NMR (400 MHz, CDCl$_3$) δ: 8.01 (m, 2H), 7.95 (m, 4H), 7.56 (s, 2H), 7.45 (m, 2H), 7.41 (d, J=8.8 Hz, 4H), 7.40 (m, 4H), 6.87 (d, J=8.8 Hz, 4H), 4.13 (t, J=4.8 Hz, 4H), 4.10 (m, 4H), 3.85 (s, 4H), 3.84 (t, J=4.8 Hz, 4H), 3.72 (t, J=4.8 Hz, 4H), 3.66 (t, J=4.8 Hz, 4H), 3.63 (t, J=4.8 Hz, 4H), 3.53 (t, J=4.8 Hz, 4H), 3.35 (s, 6H), 3.24 (m, 4H), 2.97 (m, 4H), 2.53

(m, 4H), 1.45 (s, 9H), 1.33 (m, 6H); $^{13}$C NMR (100 MHz, CDCl$_3$) δ: 161.6; 161.4 (d, J=19 Hz); 159.7; 159.6; 155.5; 153.8; 153.7 (d, J=165 Hz); 133.6; 133.5; 133.3; 132.4; 132.3; 130.1 (d, J=145 Hz); 128.1; 128.0; 126.2; 125.9 (d, J=3 Hz); 114.9; 114.7; 114.1; 114.0; 95.4; 95.1; 85.7; 85.5; 71.9; 70.8; 70.6; 70.5; 69.6; 67.5; 63.0; 49.1; 61.6; 59.0; 53.4; 28.7; 28.6; 16.5; $^{31}$P NMR (162 MHz, CDCl$_3$) δ: +26.6, +26.5 HMRS (ESI) calculated for $C_{69}H_{88}N_5O_{14}P_2$ [M+H$^+$], m/z 1272.5840. found: 1272.5800.

Compound (43c)

This compound was obtained according to the procedure used for example 43a.

minutes. The reaction progress was monitored by TLC. After this period, the reaction was complete. The solvent was removed under reduced pressure and the residue was redissolved in dichloromethane (1 mL), which was again removed under reduced pressure. This procedure was repeated 5 times to remove the excess trifluoroacetic acid. The residue was used in the rest of the synthesis without further purification. HMRS (ESI) calculated for $C_{64}H_{80}N_5O_{12}P_2$ [M+H$^+$], m/z 1172.5270. found: 1172.5280.

Compound (44c)

This compound was obtained according to the procedure used for example 44a.

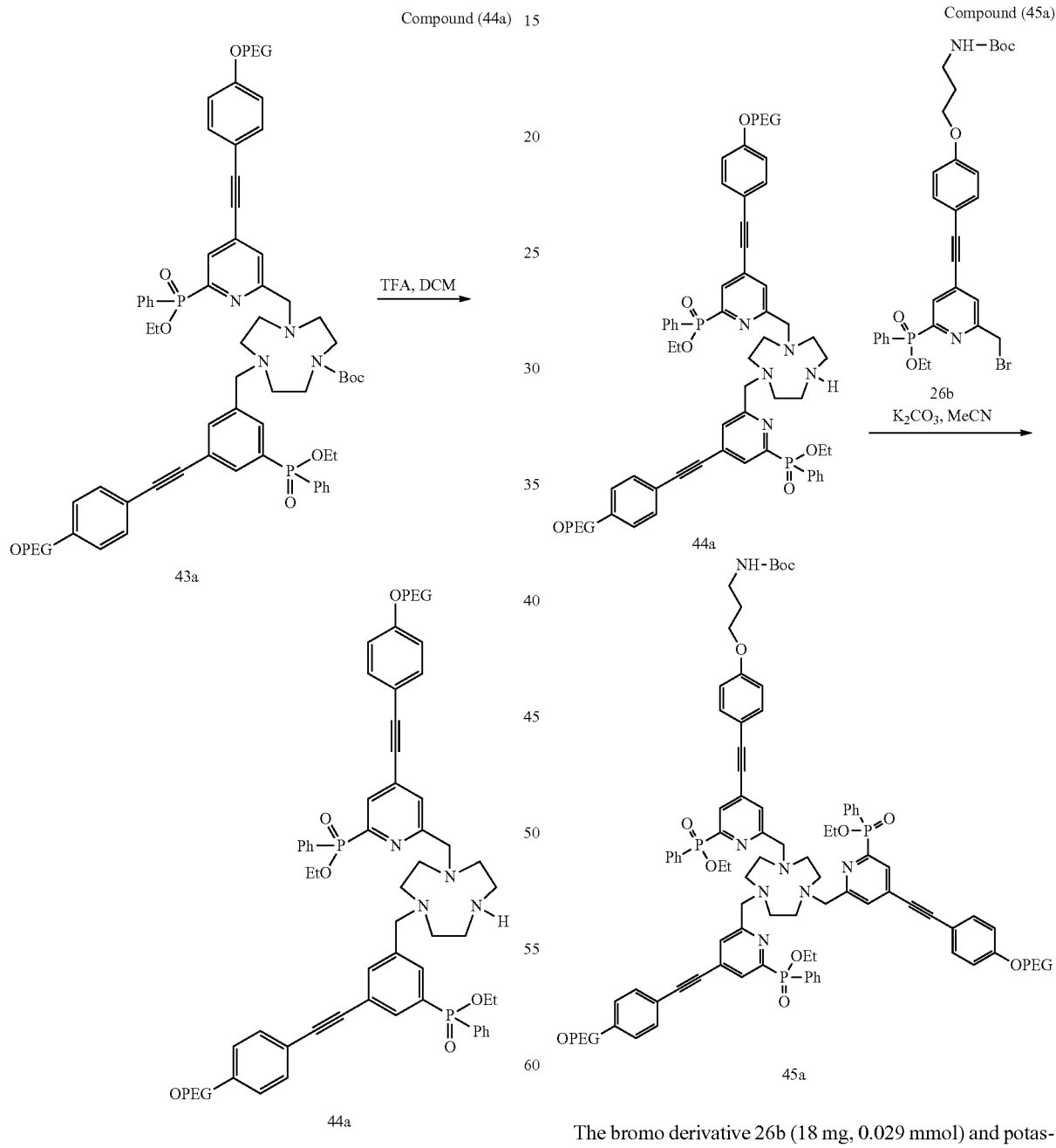

Trifluoroacetic acid (0.5 mL) was added to a solution of 43a (47 mg, 0.037 mmol) in anhydrous dichloromethane (1 mL). The solution was stirred under argon at 23° C. for 30

The bromo derivative 26b (18 mg, 0.029 mmol) and potassium carbonate (15 mg, 0.11 mmol) were added to the residue 44a obtained in the preceding step, dissolved in acetonitrile (4 mL). The suspension was stirred at 50° C. for 30 minutes. The reaction progress was monitored by TLC. After this period, the reaction was complete. The reaction mixture was cooled and the solvent was removed under reduced pressure. The residue was purified by chromatography on a column of silica (dichloromethane/methanol, 0 to 10% in 0.5% increments) to obtain the desired compound 45a in the form of a yellow oil (25 mg, 50%). $^1$H NMR (400 MHz, CDCl$_3$) δ: 8.07 (d, J=6.0 Hz, 3H), 7.85 (dd, J=8.4, J=12 Hz, 6H), 7.48 (m, 3H), 7.47 (m, 3H), 7.46 (d, J=8.8 Hz, 6H), 7.39 (m, 6H), 6.90 (d, J=8.8 Hz, 6H), 4.76 (s, 1H), 4.14 (m, 6H), 4.11 (t, J=4.8 Hz, 4H), 4.04 (t, J=6 Hz, 2H), 3.94 (s, 6H), 3.87 (t, J=4.8 Hz, 4H), 3.73 (t, J=4.8 Hz, 4H), 3.68 (t, J=4.8 Hz, 4H), 3.65 (t, J=4.8 Hz, 4H), 3.54 (t, J=4.8 Hz, 4H), 3.37 (s, 6H), 3.34 (m, 2H), 2.81 (m, 12H), 1.99 (q, J=6 Hz, 2H), 1.43 (s, 9H), 1.34 (t, J=7.2 Hz, 9H); $^{13}$C NMR (100 MHz, CDCl$_3$) δ: 160.8 (d, J=19 Hz), 160.2; 156.2; 154.6 (d, J=165 Hz); 134.0; 133.9; 132.9; 132.5 (d, J=10 Hz); 130.2 (d, J=138 Hz); 128.8; 128.7; 127.5; 115.1; 113.9; 97.0; 85.3; 79.6; 72.1; 71.1; 70.9; 70.8; 69.8; 67.8; 65.9; 62.0 (d, J=6 Hz); 59.3; 52.3; 53.0 to 46.0; 37.9; 29.7; 28.6; 16.8; $^{31}$P NMR (162 MHz, CDCl$_3$) δ: +26.4. HMRS (ESI) calculated for C$_{94}$H$_{113}$N$_7$O$_{17}$P$_3$ [M+H$^+$], m/z 1704.7400. found: 1704.7410.

Compound (45c)

This compound was obtained according to the procedure used for example 45a.

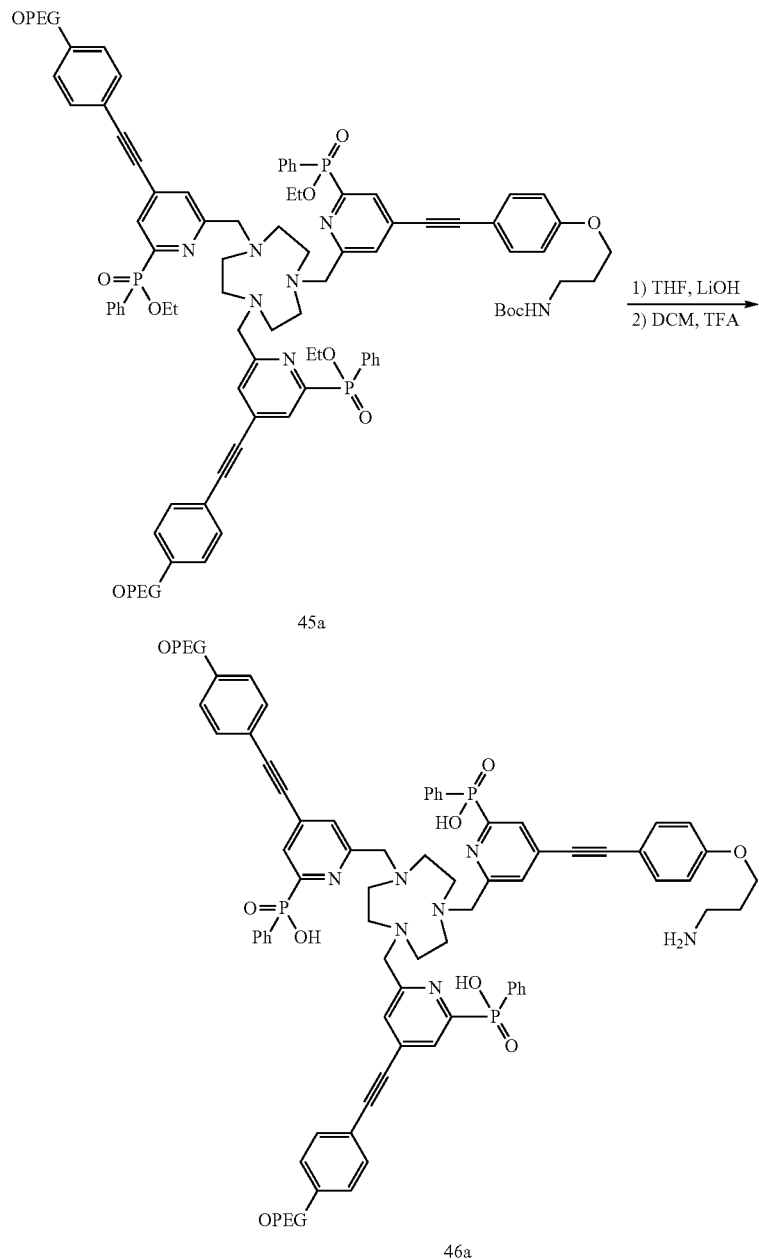

Compound (46a)

Tetrahydrofuran (6 mL) and aqueous lithium hydroxide solution (4 mL, 1 M) were added to the ligand 45a (52 mg, 30.5 μmol). The solution was stirred at room temperature for 24 hours. The reaction progress was monitored by HPLC.

After this period, the reaction was complete. The reaction mixture was concentrated under reduced pressure and used in the rest of the synthesis without further purification. MS (ESI) calculated for $C_{88}H_{103}N_7O_{17}P_3$ [M+3H$^+$], m/z 1622. Trifluoroacetic acid (3 mL) was added to a solution of the compound obtained previously in dichloromethane (6 mL). The solution was stirred at room temperature for 2 hours. The reaction progress was monitored by HPLC. After this period, the reaction was complete. The solvent was removed under reduced pressure and the residue was redissolved in dichloromethane (6 mL). The solvent was again removed under reduced pressure. This procedure was repeated 5 times to remove the excess trifluoroacetic acid. The crude product was purified by preparative HPLC to give an oil, which was used directly in the complexation step. MS (ESI) calculated for $C_{83}H_{97}N_{17}O_{15}P_3$ [M+3H$^+$], m/z 1622.

Compound (46c)

This compound was obtained according to the procedure used for example 46a.

A solution of europium acetate (7 mg, 0.016 mmol) dissolved in a water/methanol mixture (0.5 mL, 1:1 v/v) was added to a solution of compound 46a (0.016 mmol) in methanol (1 mL). The solution was stirred at 50° C. for 14 hours. The reaction progress was monitored by HPLC. After this period, the reaction was complete. The reaction mixture was cooled and the solvent was removed under reduced pressure. The residue was purified by chromatography on a column of silica (CH$_2$Cl$_2$/CH$_3$OH, 10%: NH$_3$ 0 to 1% in 0.1% increments) to obtain the europium complex 47a in the form of a white solid (9.1 mg, 34%); $^{31}$P NMR (162 MHz, CD$_3$OD) δ: +17.5. HMRS (ESI) calculated for $C_{83}H_{90}N_7O_{15}P_3Eu$ [M-CF$_3$CO$_2$]$^+$, m/z 1668.4900. found: 1668.4980.

Compound (47c)

This compound was obtained according to the procedure used for example 47a.

Compounds 50a, 50c, 53a and 53c

These compounds were obtained according to the procedure used for examples 47a and 47c.

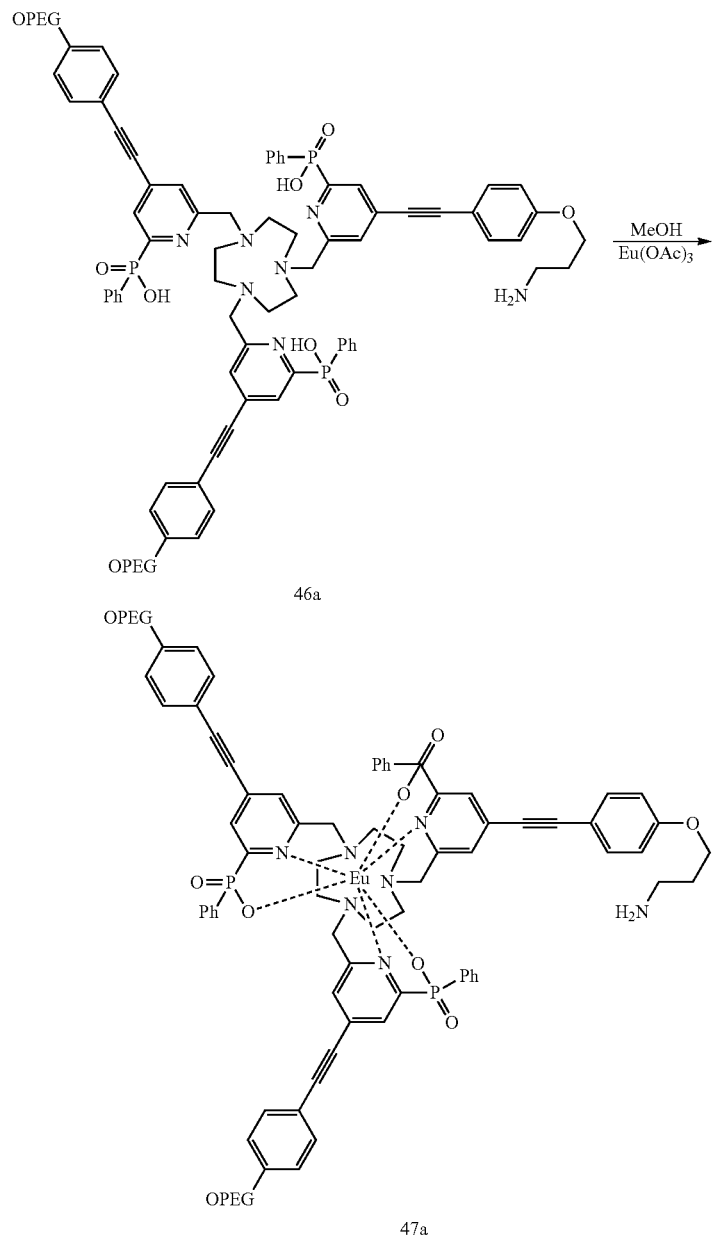

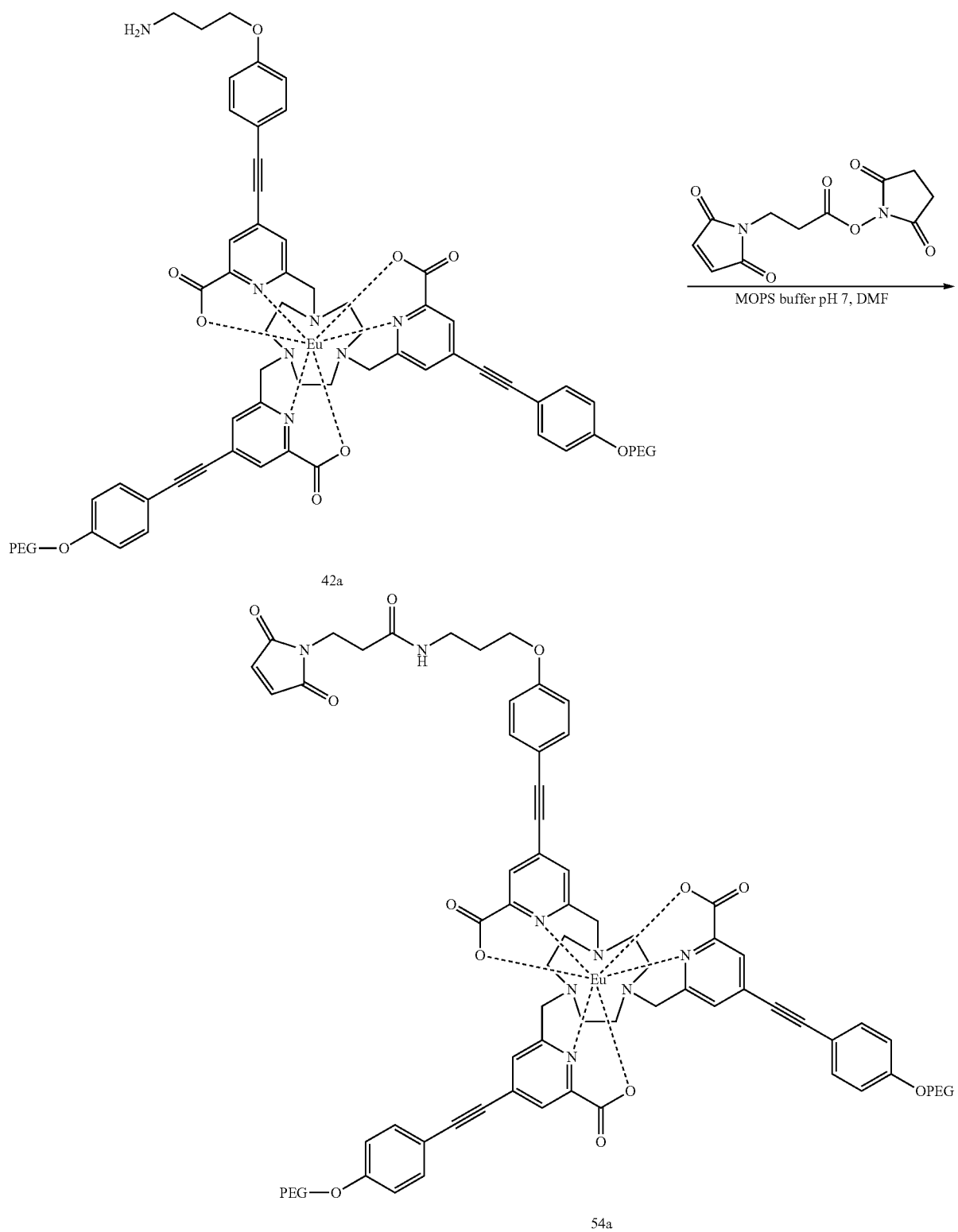

A solution of N-[β-maleimidopropyloxy]succinimidyl ester (41 μL, 300 nmol) in dimethylformamide prepared from a stock solution (1.92 mg of N-[β-maleimidopropyloxy]succinimidyl in 1000 μL of dimethylformamide) was added to a solution of europium $NH_2$ complex 42a (200 nmol) in MOPS buffer pH 7 (200 μL). The reaction medium was stirred at room temperature over night. The reaction progress was monitored by HPLC. After this period, the reaction was complete. The reaction medium was purified by preparative HPLC to give compound 54a in the form of an oil (105 nmol, 52%).

Compounds (55a)-(55c), (56a)-(56c) and (57a)-(57c)

These compounds were obtained according to the procedure used for example 54a.

(62.7 nmol, 31%). ESI-MS m/z calculated for $C_{73}H_{80}N_7O_{18}Eu+H^+=1382.45$. Diisopropylethylamine (0.8 µL) and then O—(N-succinimidyl)-1,1,3,3-tetramethyluronium tetrafluoroborate (0.3 mg, 1 µmol) were added to a solution of acid complex (550 nmol) in anhydrous dimethyl- Compound (58a)

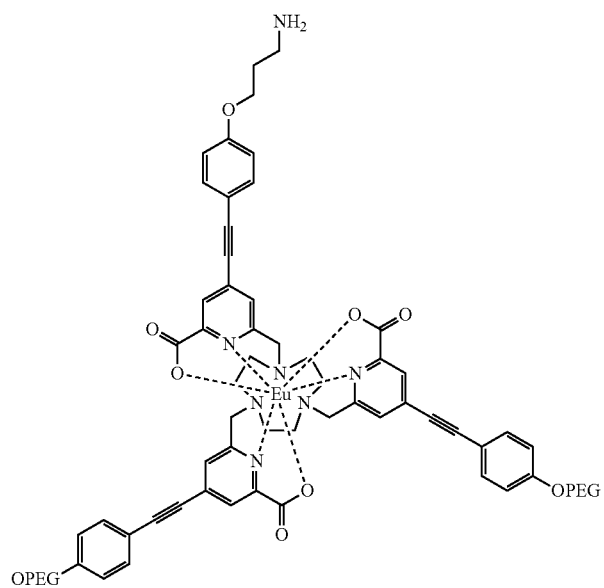

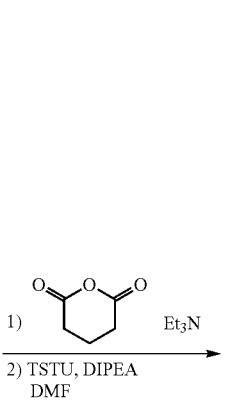

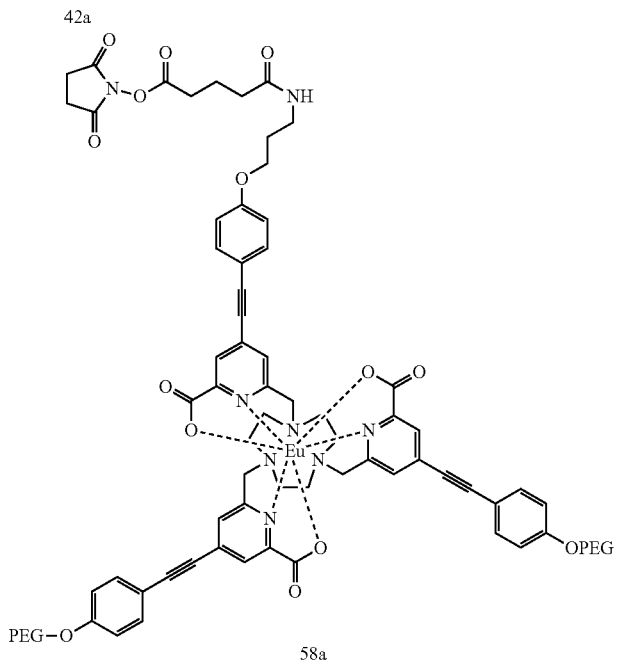

Triethylamine (1 µL) was added to a solution of europium NH₂ complex 42a (200 nmol) in anhydrous DMF (100 µL). A solution of glutaric anhydride (236 nmol) in dimethylformamide (27.4 µL) was added to this mixture. The mixture was stirred at room temperature over night. The reaction progress was monitored by HPLC. After this period, the reaction was complete. The reaction medium was purified by preparative HPLC to give the desired compound in the form of an oil formamide (200 µL). The reaction mixture was stirred at room temperature for 15 minutes. The reaction progress was monitored by HPLC. After this period, the reaction was complete. The reaction medium was purified directly by preparative HPLC to give the NHS compound 58a (370 nmol, 74%). ESI-MS m/z calculated for $C_{73}H_{80}N_7O_{18}Eu+H^+=1382.45$.

Compounds (59a)-(59c), (60a)-(60c) and (61a)-(61c)

These compounds were obtained according to the procedure used for example 58a.

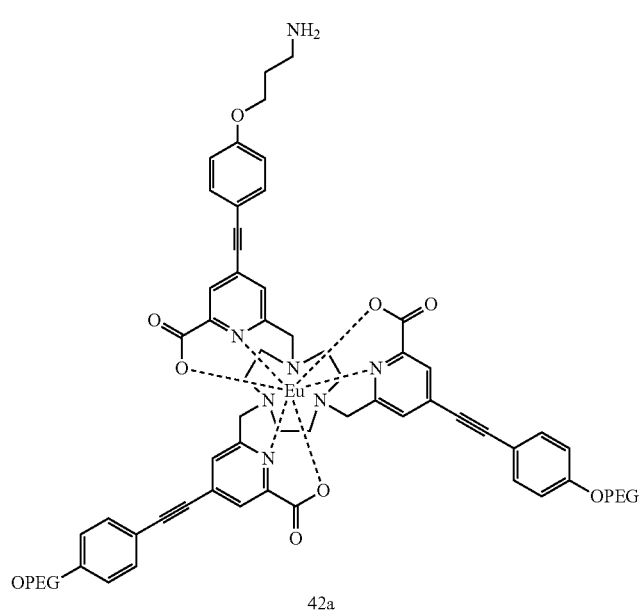

42a

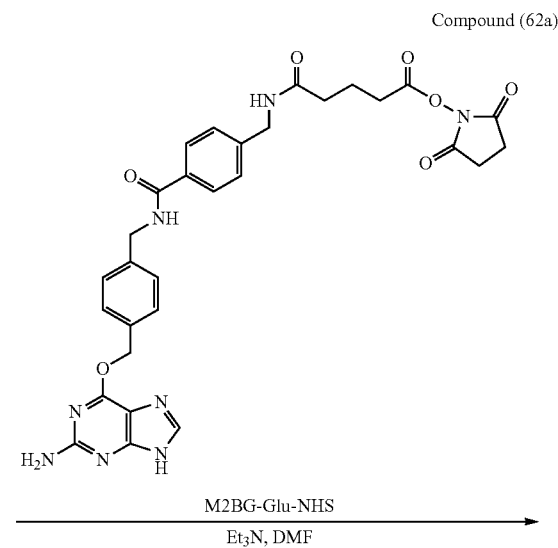

Compound (62a)

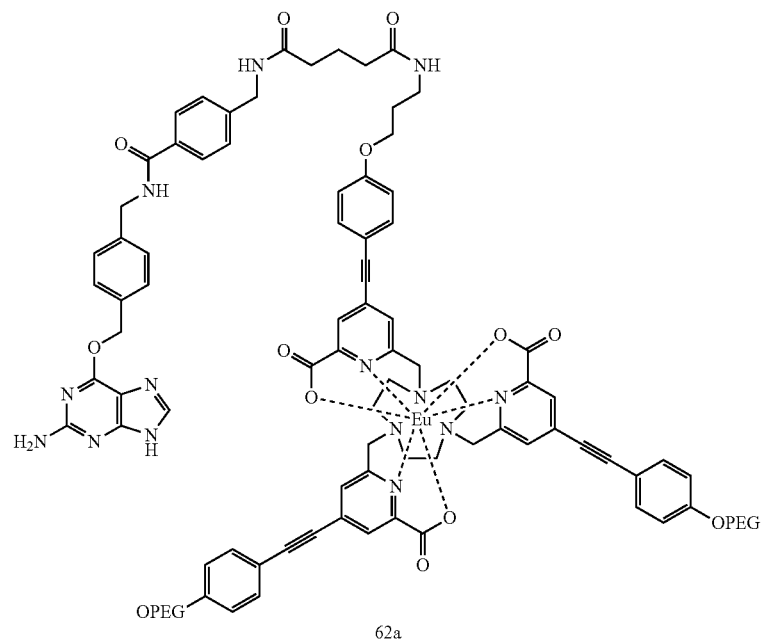

62a

Triethylamine (1.5 µL) and a solution of M2BG-glu-NHS (100 nmol) in dimethylformamide (50 µL) were added to a solution of europium NH₂ complex 42a (100 nmol) in dimethylformamide (50 µL). The reaction mixture was stirred at room temperature for 2 hours. The reaction progress was monitored by HPLC. After this period, a second addition equivalent to the first was performed (triethylamine and a solution of M2BG-glu-NHS in dimethylformamide). The reaction mixture was stirred at room temperature over night. After this period, the reaction was complete. The reaction mixture was purified by preparative HPLC to give compound 62a in the form of an oil (68 nmol, 68%). ESI-MS m/z calculated for $C_{68}H_{74}N_7O_{15}Eu+H^+=1382.45$.

Compounds (63a), (63c), (63d), (64a), (64c), (64d), (65a), (65c) and (65d)

These compounds were obtained according to the procedure used for example 62a.

Compound (66a)
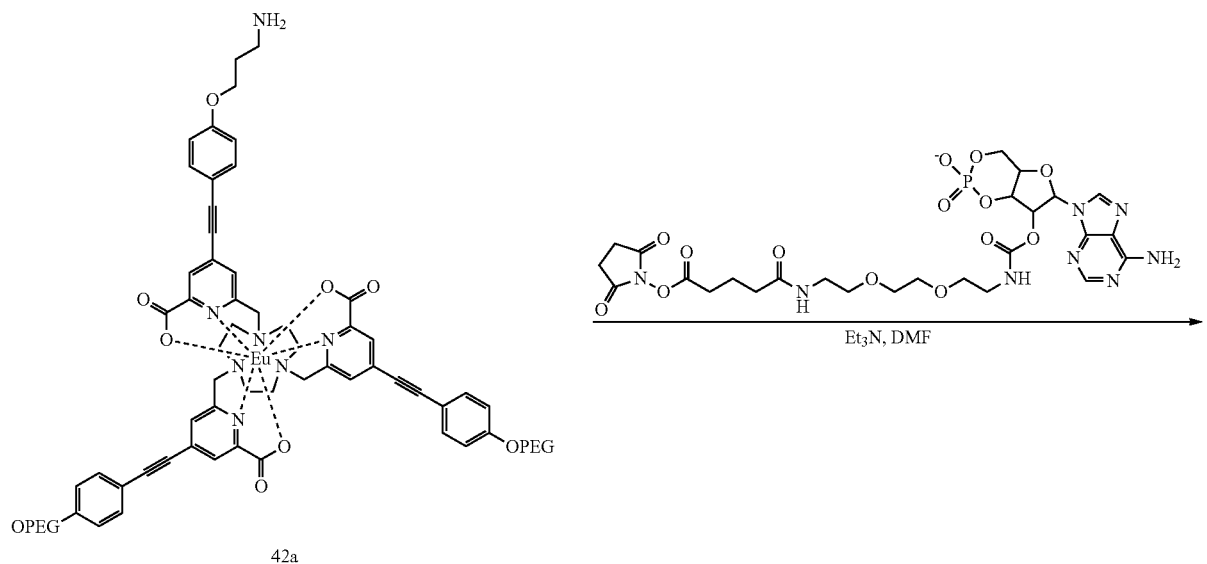
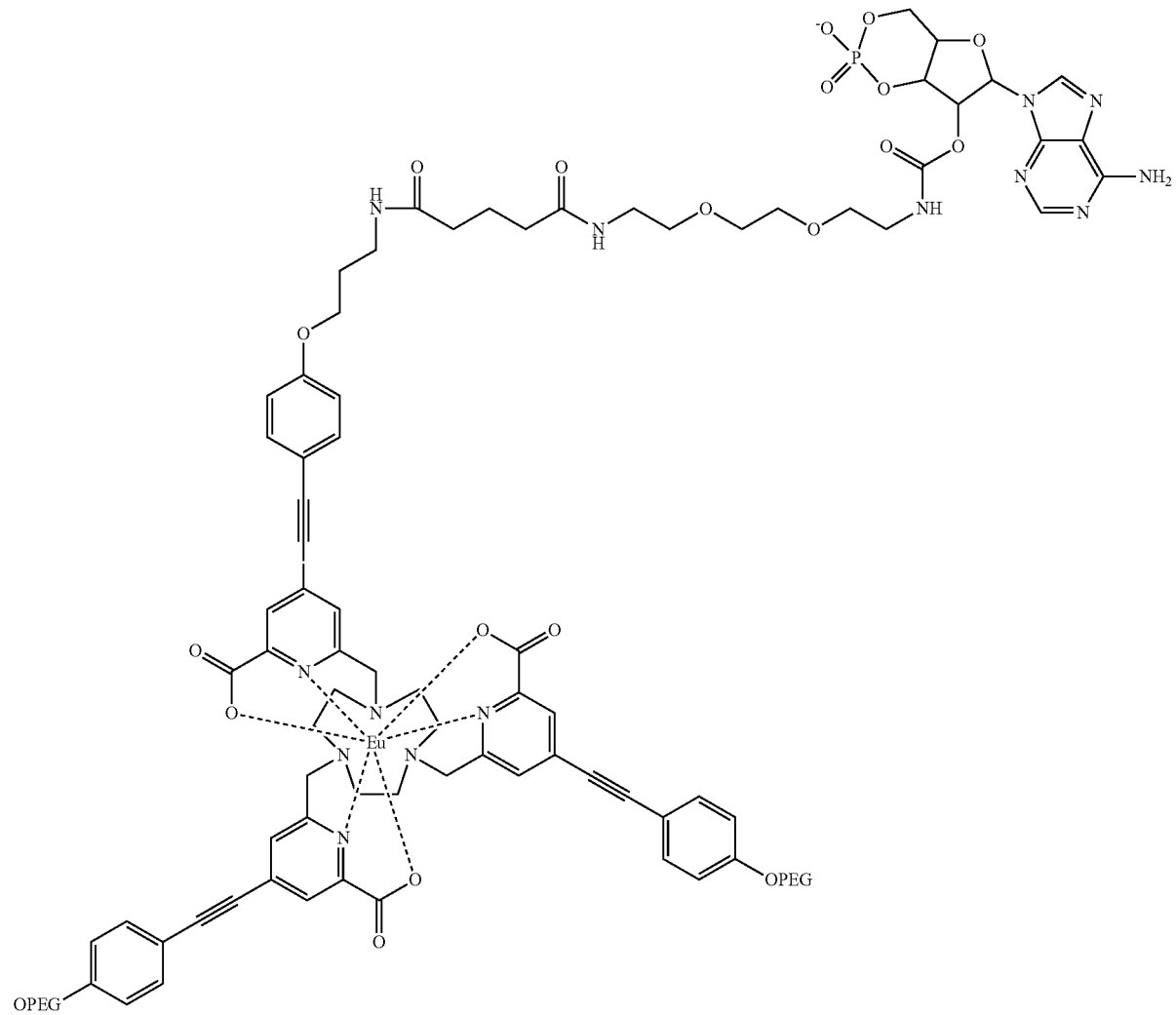

Triethylamine (5 µL) was added to a solution of europium NH$_2$ complex 42a (200 nmol) in dimethylformamide (100 µL). A stock solution of cAMP-NHS was prepared containing cAMP-NHS (200 nmol) in dimethylformamide (200 µL). This stock solution was added to the solution of the complex. The reaction medium was stirred over night. The reaction progress was monitored by HPLC. The reaction medium was purified by preparative HPLC to give compound 66a in the form of an oil (62 nmol, 31%).

Compounds (67c), (67d), (68c), (68d), (69c) and (69d)

These compounds were obtained according to the procedure used for example 66a.

Compound (71)

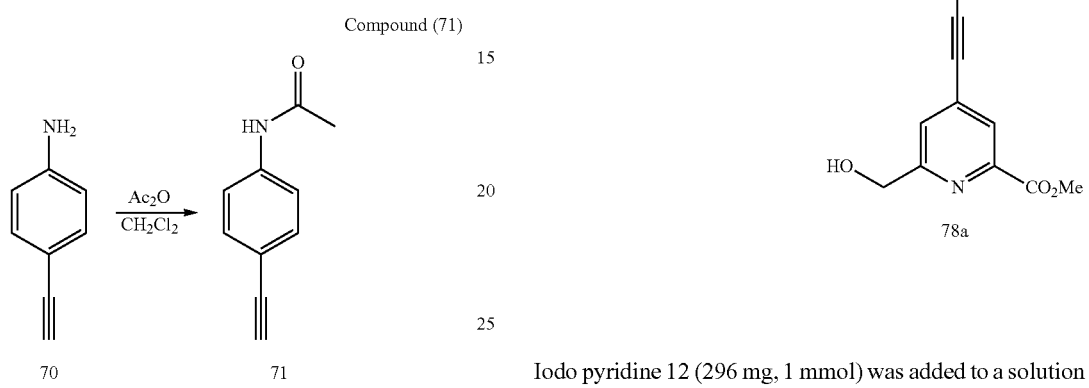

Acetic anhydride (2.5 mL, 40 mmol) was added to a solution of 4-ethynylaniline 70 (2.34 g, 20 mmol) in dichloromethane (30 mL). The reaction medium was stirred at room temperature for 16 hours. The reaction progress was monitored by TLC. After this period, the reaction was complete. The solvent was removed under reduced pressure. Saturated sodium bicarbonate solution (15 mL) was added to the black residue, and the mixture was extracted with dichloromethane (2×15 mL). The organic phases were combined and then dried over magnesium sulfate. After filtration, the solvent was removed under reduced pressure. The crude product obtained was purified by flash chromatography on a column of silica (ethyl acetate/cyclohexane, 98/2 to 60/40 in 5% increments) to give compound 71 in the form of a slightly pinkish solid (2.05 g, 64%). m.p.: 118.4-125.3° C.

Compounds (72) and (73)

These compounds were obtained using the method described in the literature (Inorganic Chemistry-2005-44 (18) 6284).

Compound (74)

This compound was obtained using the method described in the literature (Journal of American Chemical Society 2009-131 (35) 12560).

Compound (78a)

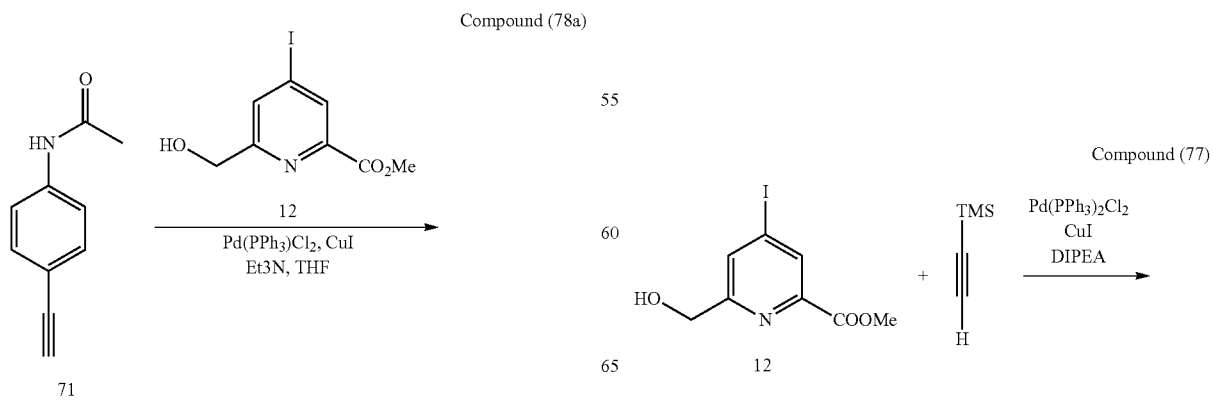

Iodo pyridine 12 (296 mg, 1 mmol) was added to a solution of acetylenic derivative 71 (174 mg, 1.1 mmol) in anhydrous tetrahydrofuran (20 mL) and anhydrous triethylamine (10 mL). The mixture was degassed with stirring for 1 hour. Bis(triphenylphosphine)palladium(II) dichloride (70 mg, 0.2 mmol) and copper(I) iodide (38 mg, 0.4 mmol) were added to this solution. The reaction medium was stirred at 50° C. for 18 hours protected from light. The reaction progress was monitored by TLC. After this period, the reaction was complete. The solvents were removed under reduced pressure. Water (10 mL) was added to the black residue, and the mixture was extracted with ethyl acetate (3×20 mL). The organic phases were combined and dried over magnesium sulfate. After filtration, the solvent was removed under reduced pressure. The crude product obtained was purified by flash chromatography on a column of silica (dichloromethane/methanol, 0.5% to 20% in 1% increments) to give compound 78a in the form of a brown solid (200 mg, 61%).

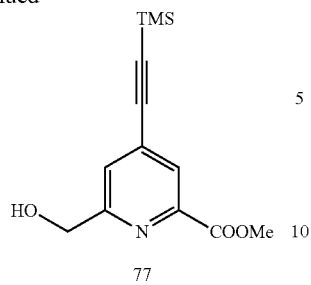

Anhydrous tetrahydrofuran (10 mL) was added to the iodo pyridine 12 (3.22 g, 11 mmol) and the solution was degassed via three freezing-thawing cycles. Trimethylsilylacetylene (7.8 mL, 55 mmol) and diisopropylethylamine (9.6 mL, 50 mmol) were added to this solution, and the solution was again degassed. Tetrakis(triphenylphosphine)palladium(0) (385 mg, 0.55 mmol) and copper iodide (209 mg, 0.11 mmol) were added to this solution. This new solution was again degassed three times and was then stirred under argon. A color change from very pale yellow to dark brown was observed, and the mixture was stirred at 65° C. under argon. The reaction progress was monitored by TLC. After 3 hours, the reaction was complete. The reaction mixture was cooled to room temperature and the solvent was removed under reduced pressure. The crude product was purified by chromatography on a column of silica (dichloromethane/methanol, 0 to 4% in 0.5% increments) to give compound 77 (2.61 g, 90%); $^1$H NMR (400.13 MHz, CDCl$_3$) δ: 8.01 (s, 1H), 7.56 (s, 1H), 4.82 (s, 2H), 3.97 (s, 3H), 0.25 (s, 9H); $^{13}$C NMR (100 MHz, CDCl$_3$) δ: 165.2; 160.8; 147.2; 133.4; 126.2; 126.0; 101.9; 101.3; 64.6; 53.1; −0.3. HMRS (ESI) calculated for C$_{13}$H$_{18}$O$_3$NSi [M+H$^+$], m/z 264.1056 found: 264.1050.

Compound (77a)

This compound was obtained using the method described in the literature on 4-nitrophenol (Bioorganic & Medicinal Chemistry Letters 2007-17-5428).

Method B

Compound (78u)

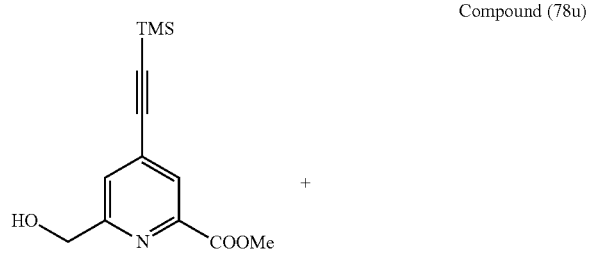

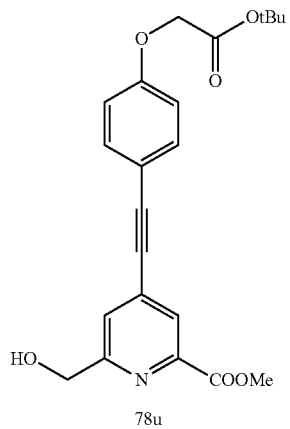

Iodo derivative 77a (370 mg, 1 mmol) was added to a solution of acetylenic derivative 77 (263 mg, 1 mmol) in anhydrous tetrahydrofuran (10 mL) and anhydrous triethylamine (5 mL). The mixture was degassed with stirring for 1 hour. A 1 M solution of tetrabutylammonium fluoride in tetrahydrofuran (1.5 mL, 1.5 mmol), bis(triphenylphosphine) palladium(II) dichloride (72 mg, 0.1 mmol) and copper(I) iodide (40 mg, 0.2 mmol) were added to this solution. The reaction medium was stirred at 75° C. for 3 hours, protected from light. The reaction progress was monitored by TLC. After this period, the reaction was complete. The solvents were removed under reduced pressure. Water (10 mL) was added to the black residue, and the mixture was extracted with dichloromethane (3×20 mL). The organic phases were combined and dried over magnesium sulfate. After filtration, the solvent was removed under reduced pressure. The crude product obtained was purified by flash chromatography on a column of silica (dichloromethane/methanol, 0.5% to 5% in 1% increments) to give compound 78u in the form of a yellowish oil (203 mg, 54%).

Compound (79a)

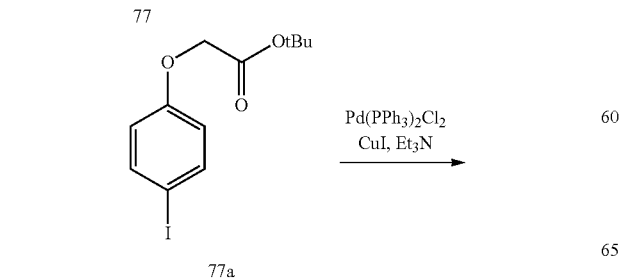

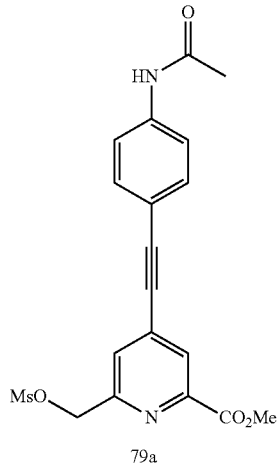

79a

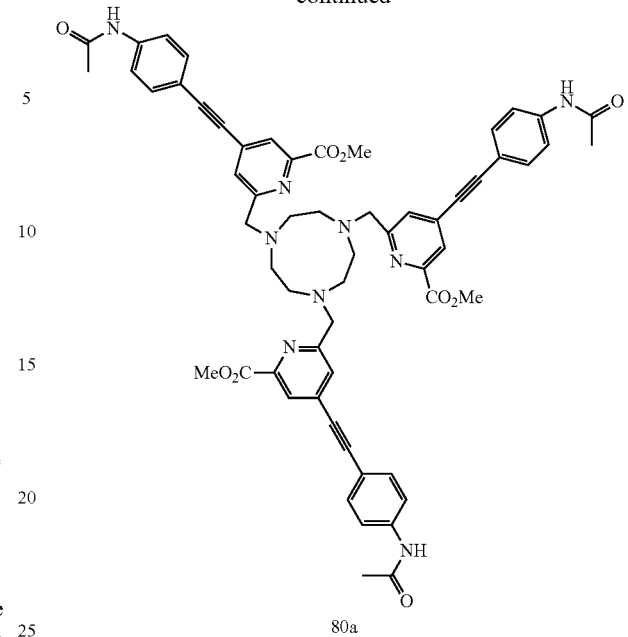

80a

Triethylamine (0.3 mL, 1.8 mmol) and then mesyl chloride (70 μL, 1.8 mmol) were added to a solution of alcohol 78a (195 mg, 0.6 mmol) in anhydrous tetrahydrofuran (14 mL) cooled to 5° C., under an inert atmosphere. The reaction medium was stirred at room temperature for 15 minutes. The reaction progress was monitored by TLC. After this period, the reaction was complete. The solvent was removed under reduced pressure. Saturated aqueous sodium chloride solution (30 mL) was added to the residue, and the mixture was extracted with dichloromethane (2×30 mL). The organic phases were combined and dried over magnesium sulfate. After filtration, the solvent was removed under reduced pressure to give a brown solid corresponding to compound 79a (231 mg, 95%), which was pure enough to be used in the following step without further purification.

Potassium carbonate (82 mg, 0.6 mmol) and 1,4,7-triazacyclononane (12.9 mg, 0.1 mmol) were added to a solution of mesyl derivative 79a (120 mg, 0.3 mmol) in anhydrous acetonitrile (4 mL) under an inert atmosphere. The reaction medium was refluxed for 24 hours. The reaction progress was monitored by TLC. After this period, the reaction was complete. The reaction medium was cooled to room temperature and the solvent was removed under reduced pressure. Water (10 mL) was added to the residue, and the mixture was extracted with ethyl acetate (2×20 mL). The organic phases were combined and dried over magnesium sulfate. After filtration, the solvent was removed under reduced pressure. The crude product obtained was purified by preparative HPLC to give compound 80a in the form of a white solid (12 mg, 12%).

Compound (80b)

80b

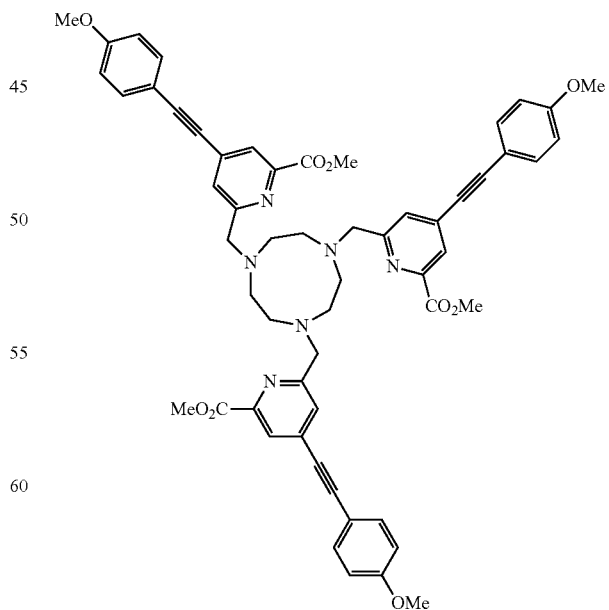

Compound (80a)

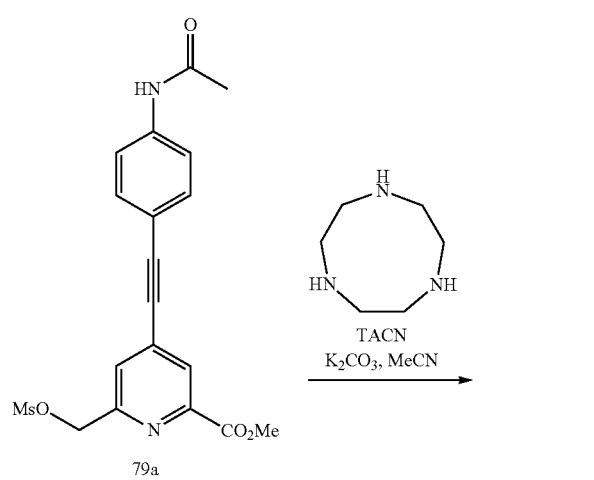

This compound was obtained according to the procedure used for example 80a.

Compound (80c)
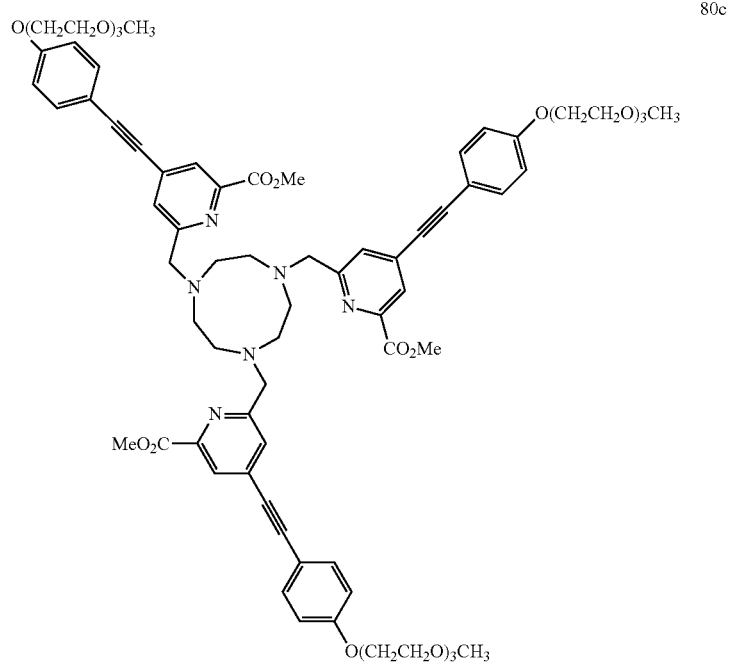
This compound was obtained according to the procedure used for example 80a.
Compound (81a)
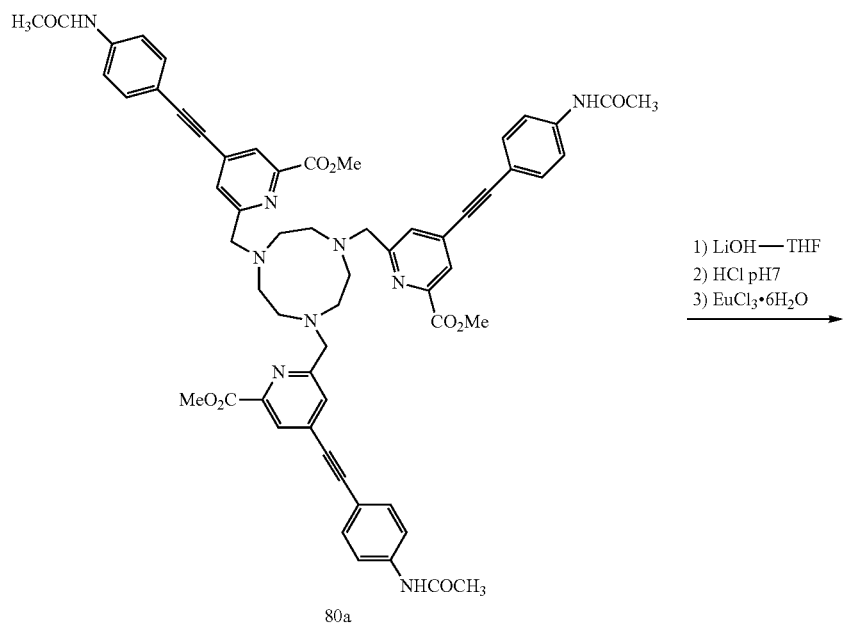
1) LiOH—THF
2) HCl pH7
3) EuCl$_3$•6H$_2$O

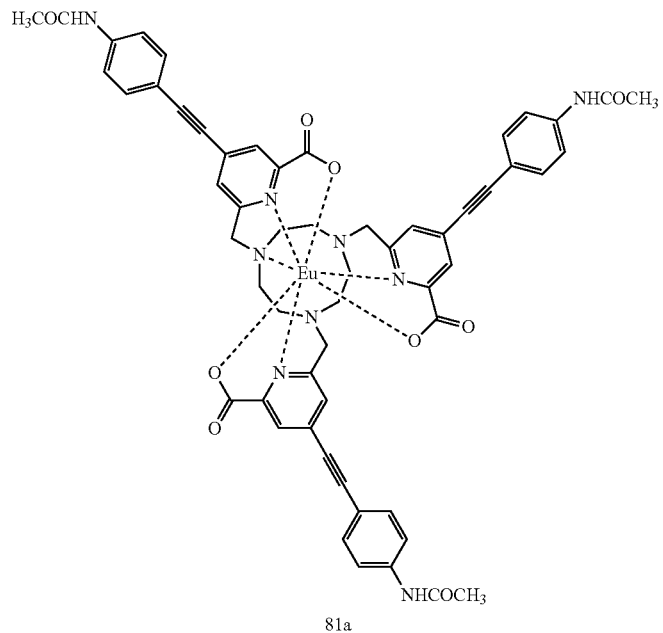
81a
This compound was obtained according to the procedure used for example 81b below.
Compound (81b)
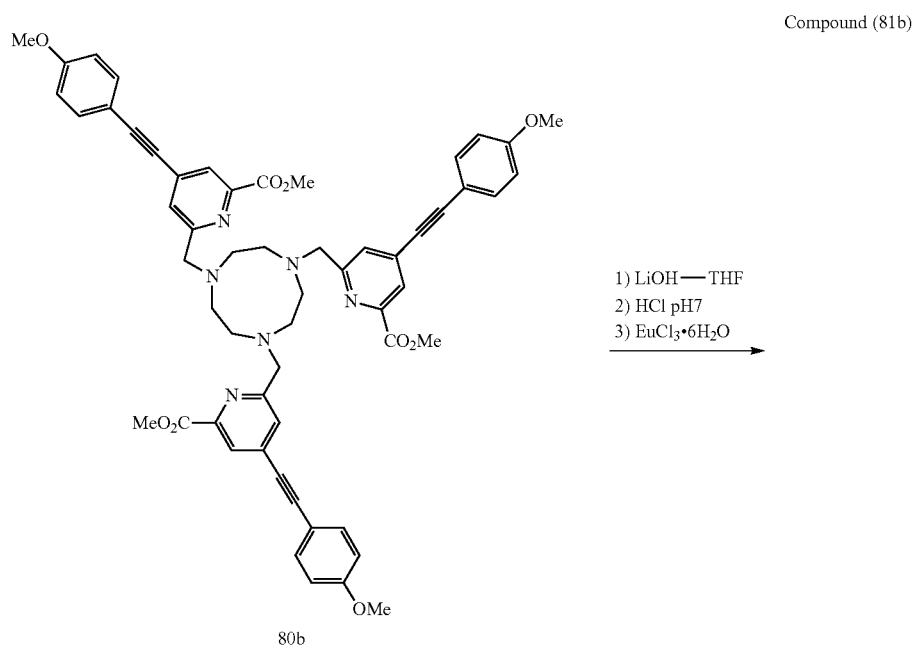
80b
1) LiOH—THF
2) HCl pH7
3) EuCl$_3$·6H$_2$O -continued

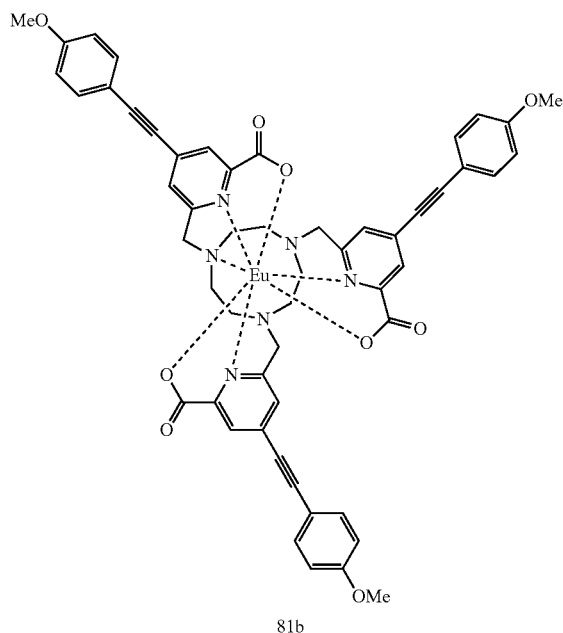

81b

Aqueous lithium hydroxide solution (1 mL, 1 M) was added to a solution of the triester ligand 80b (33 mg, 34 µmol) in tetrahydrofuran (3 mL). The solution was stirred at room temperature for 30 minutes. The reaction progress was monitored by LC-MS. After this period, the reaction was complete. The pH of the solution was adjusted to 7 by adding hydrochloric acid (1 M). Europium chloride hexahydrate (37 mg, 102 µmol) was added to this solution. The reaction mixture was stirred at room temperature for 30 minutes. The solvent was removed under reduced pressure and the crude product was dissolved in acetonitrile (4 mL) and then purified by preparative HPLC to give the desired compound 81b in the form of a white solid (23 mg, 63%).

Compound (81c)

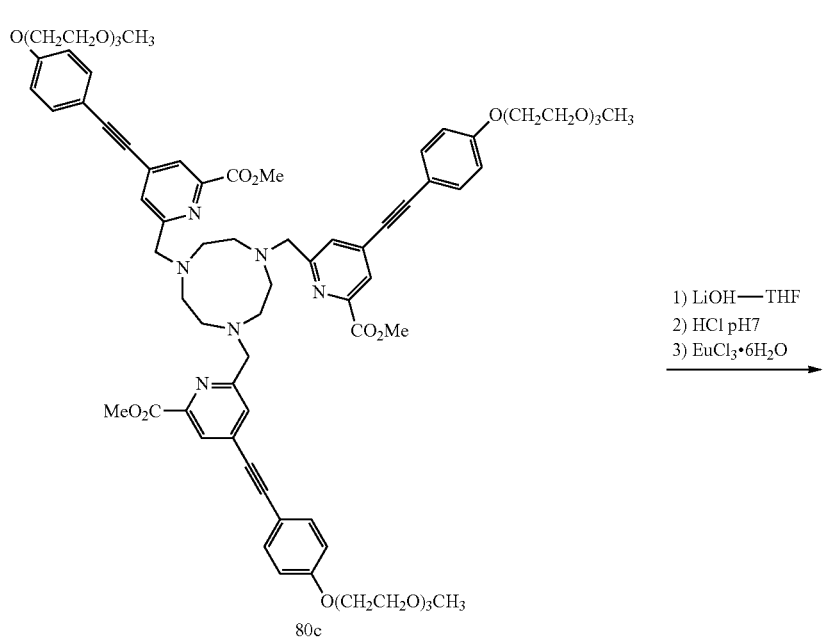

80c

1) LiOH—THF
2) HCl pH 7
3) EuCl$_3$•6H$_2$O

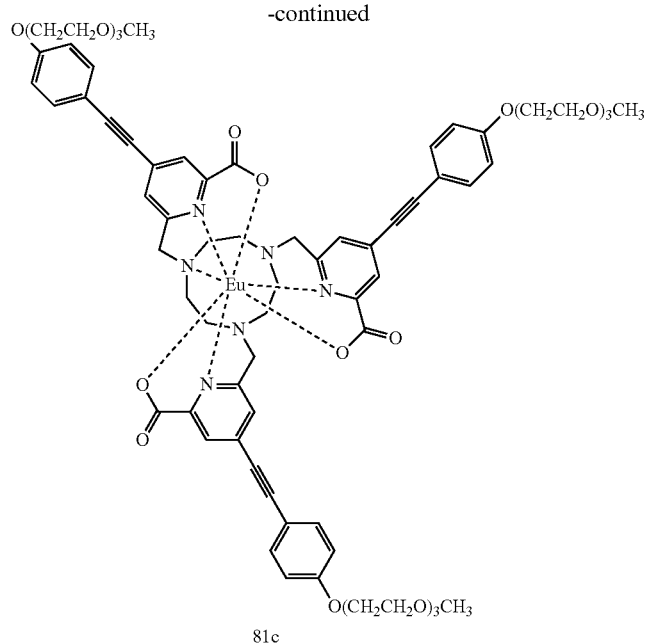

81c

This compound was obtained according to the procedure used for example 81b.

Example 1

Luminescence Intensity Stability of the Compounds of the Invention

The luminescence stability of various compounds according to the invention (37a, 47a, 53a, 62a, 66a, 67a, 69a, 81a, 81c), and also that of a compound of the prior art (compound 39 described by Latva et al. in Journal of Luminescence, Volume 75, No. 2, September 1997, Pages 149-169, having the formula below) were measured in various media.

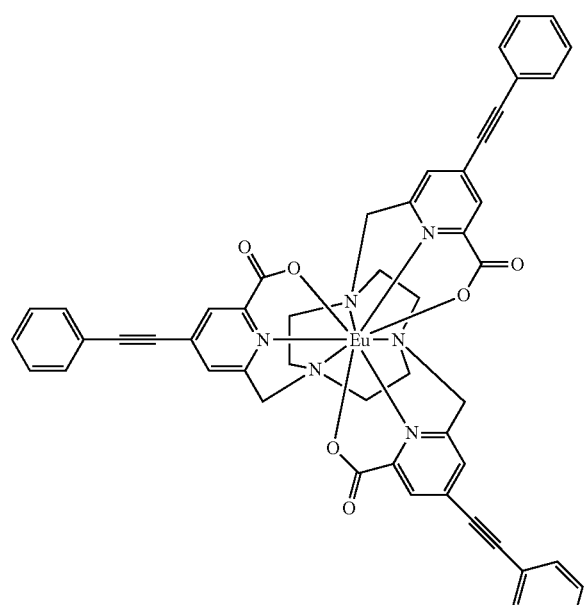

'latva'

Solutions of each of these compounds at a concentration of 100 to 500 μM were prepared in 50 mM HEPES buffer at pH 7.4 with 0.1% bovine serum albumin (BSA). 50 μl of each solution were placed in wells of 96-well plates (Corning Costar 3915), to which were added 45 μl of HEPES buffer or 50 μl of NBCS ("newborn calf serum" (supplier: Bayer)). The wells were finally completed either with 5 μl of water (to obtain a basal signal, "base" in FIG. 1) or with 5 μl of a 400 mM solution of $CaCl_2$, $MgCl_2$, $MnCl_2$ or EDTA. These solutions are known for their effect on rare-earth metal complexes: Ca++ and Mg++ ions can compete with europium for the bonding with the complexing agent and EDTA may have the effect of chelating europium. The Mn++ ion is also known for its capacity to bring about luminescence extinction.

After 10 minutes, the luminescence was measured on a Rubystar reader at 620 nm with a measuring delay of 50 μs and an integration time of 400 μs. The signals measured were normalized by the "base" signal for each compound and the results obtained are presented in FIG. 1. The error bars represent the standard deviation on three wells.

FIG. 1 shows that the presence of 20 mM of $CaCl_2$, $MgCl_2$, or EDTA does not significantly affect the luminescence of the compounds according to the invention, which may be correlated with the stability of these complexes.

It is noted that the complexes with "phosphinate" arms such as 37a, 47a and 67a show excellent luminescence stability in the presence of $MnCl_2$ when compared with the other complexes, including that of the prior art (Latva).

Finally, the luminescence of all the complexes according to the invention is significantly more stable than that of the complex of the prior art in the presence of NBCS, which is particularly advantageous for using these compounds, for example for the analysis of blood samples in the diagnostic field.

Example 2

Excitation Spectra of the Compounds of the Invention

The solutions of compounds in HEPES buffer (pH 7.4, 0.1% BSA) of the preceding example were used to obtain the excitation spectra for these compounds. To do this, these solutions were placed in quartz cuvettes in a "Cary Eclipse" fluorescence spectrophotometer (Varian). It was checked that the absorption at 337 nm of these solutions was less than 0.05 unit in a 1 cm cuvette.

The excitation spectra were obtained in "phosphorescence" mode by measuring the emission at 615 nm after excitation at various wavelengths. The measurements were performed with a 0.1 ms delay and an integration time of 10 ms. The excitation slit was 5 nm, the emission slit was 2.5 nm and the photomultiplier voltage was 800 V.

Figure 2:
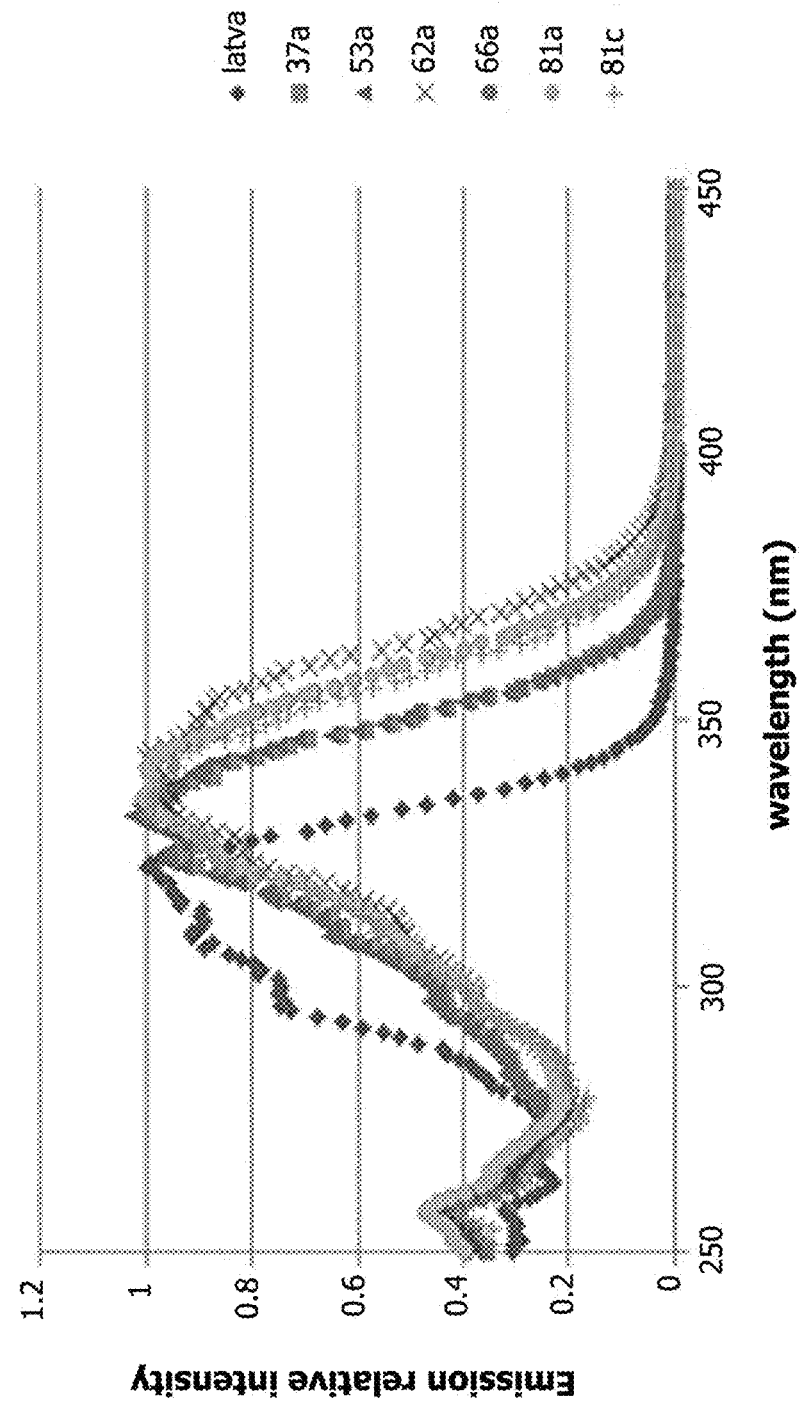
FIG. 2 shows the excitation spectrum of the compounds of the invention in HEPES buffer.

FIG. 2 shows the excitation spectra obtained after normalization of the signal measured by the maximum signal for each compound. The excitation spectra for the compounds according to the invention show a bathochromic shift relative to that for the compound of the prior art (Latva compound), making them particularly sensitive to excitation at 337 nm, which corresponds to the wavelength of the light emitted by nitrogen lasers, which are widely used in plate readers. These spectra also show that the compounds of the invention may also be excited at higher wavelengths, for example 365 nm or 380 nm. It is particularly advantageous to use the latter wavelengths for applications in microscopy, since they limit the light absorption by the biological materials present in the measuring medium and by the glassware present in the microscopes.

Example 3

Photophysical Properties of the Compounds of the Invention

Several compounds according to the invention were prepared and their photophysical properties, in particular the wavelengths corresponding to their maximum absorption peaks (λmax), were determined. The structures of these compounds and the results obtained are described in table 2.

The chromophores (similar to compound 78, carboxylate function protected in ester form) were synthesized according to the protocol described in scheme 13, using one of the two approaches "A" or "B" as described in this scheme (including that for the chromophores comprising naphthyl, thiolanyl, imidazolyl and anthracenyl rings or heterocycles). For each chromophore, the UV spectra were recorded and the maximum absorption wavelengths ($\lambda_{max}$) were determined and reported in table 2.

For certain chromophores, europium complexes according to the invention in which the three chromophores are identical (symmetrical complexes) were prepared using the protocol described in scheme 14, with a TACN macrocycle (the synthetic yields for the intermediate compounds 79, 80 and 81 of scheme 14 were reported in table 2). The photophysical properties of these europium complexes were determined and also reported in this table.

TABLE 2

| Chromophore | 78a | 78b | 78c |
|---|---|---|---|
| Method A or B (Scheme 13) | A | A | A |
| Chromophore 78 Yield (%) | 64 | 67 | 78 |
| λmax (nm) | 322 | 320 | 321 |
| Mesyl compound 79 Yield (%) | 95 | 95 | 93 |
| Triester ligand 80 Yield (%) | 56 | 84 | 57 |
| Complex 81 Yield (%) | 10 | 63 | 89 |
| Complex 81 λmax (nm) | — | 333 | — |
| Complex 81 Quantic yield (%) | — | 52 | — |

TABLE 2-continued

| Chromophore | 78d | 78e | 78f |
|---|---|---|---|
| Method A or B (Scheme 13) | B | A | A |
| Chromophore 78 Yield (%) | 88 | 54 | 84 |
| λmax (nm) | 324 | 319 | 323 |
| Mesyl compound 79 Yield (%) | — | — | 80 |
| Triester ligand 80 Yield (%) | — | — | 10 |
| Complex 81 Yield (%) | — | — | 18 |
| Complex 81 λmax (nm) | — | — | 336 |
| Complex 81 Quantic yield (%) | — | — | 46 |

| Chromophore | 78g | 78h | 78i |
|---|---|---|---|
| Method A or B (Scheme 13) | A | A | A |
| Chromophore 78 Yield (%) | 36 | 82 | 48 |
| λmax (nm) | 319 | 315 | 329 |
| Mesyl compound 79 Yield (%) | 24 | — | — |
| Triester ligand 80 Yield (%) | 57 | — | — |
| Complex 81 Yield (%) | 32 | — | — |
| Complex 81 λmax (nm) | 336 | — | — |
| Complex 81 Quantic yield (%) | 11 | — | — |

TABLE 2-continued

| Chromophore | 78j | 78k | 78l |
|---|---|---|---|
| Method A or B (Scheme 13) | A | A | A |
| Chromophore 78 Yield (%) | 48 | 80 | 78 |
| λmax (nm) | 335 | 326 | 315 |
| Mesyl compound 79 Yield (%) | — | 81 | 54 |
| Triester ligand 80 Yield (%) | — | 22 | 63 |
| Complex 81 Yield (%) | — | 7 | 37 |
| Complex 81 λmax (nm) | — | 323 | 333 |
| Complex 81 Quantic yield (%) | — | 52 | 54 |

| Chromophore | 78m | 78n | 78o |
|---|---|---|---|
| Method A or B (Scheme 13) | A | A | A |
| Chromophore 78 Yield (%) | 96 | 95 | 71 |
| λmax (nm) | 291 | 318 | 326 |
| Mesyl compound 79 Yield (%) | — | — | — |
| Triester ligand 80 Yield (%) | — | — | — |
| Complex 81 Yield (%) | — | — | — |
| Complex 81 λmax (nm) | — | — | — |

TABLE 2-continued

| | | | |
|---|---|---|---|
| Complex 81 Quantic yield (%) | — | — | — |
| Chromophore | 78p | 78q | 78r |
| Method A or B (Scheme 13) | A | A | A |
| Chromophore 78 Yield (%) | 56 | 95 | 95 |
| λmax (nm) | 324 | 323 | 332 |
| Mesyl compound 79 Yield (%) | — | — | 36 |
| Triester ligand 80 Yield (%) | — | — | 39 |
| Complex 81 Yield (%) | — | — | 0.5 |
| Complex 81 λmax (nm) | — | — | — |
| Complex 81 Quantic yield (%) | — | — | — |
| Chromophore | 78s | 78t | 78u |
| Method A or B (Scheme 13) | A | A | B |
| Chromophore 78 Yield (%) | 89 | 89 | 54 |
| λmax (nm) | 326 | 326 | 318 |

TABLE 2-continued

| | | | |
|---|---|---|---|
| Mesyl compound 79 Yield (%) | 33 | — | 95 |
| Triester ligand 80 Yield (%) | 42 | — | 6 |
| Complex 81 Yield (%) | 7 | — | 5 |
| Complex 81 λmax (nm) | 343 | — | — |
| Complex 81 Quantic yield (%) | 76 | — | — |

Results:

With the exception of compound 78m, corresponding to the reference compound of the prior art (compound 39 from Latva), all the chromophores tested had a maximum absorption wavelength (λmax) of between 310 and 332 nm. It was determined that the complexation of europium with a chromophore induces a bathochromic effect of 10 to 20 nm as a function of the type of structure of the ligand (see the λmax values for chromophores 78b, 78f, 78g, 78k, 78l and the λmax values for the corresponding europium complexes). Thus, table 2 shows that all the symmetrical europium complexes (compounds of formula 81) comprising the chromophores described in this table are entirely suited to laser excitation at 337 nm. Moreover, the europium complexes also have a quantic yield that is sufficient (>10%) for these compounds to be able to be used as fluorescent markers.

Example 4

Compared Properties

The photophysical properties of several compounds according to the invention were compared and the following elements were discovered:
  the photophysical properties of a symmetrical europium complex (three identical chromophores $chrom_1$ $chrom_2$ and $chrom_3$) are the same as those of a dissymmetrical europium complex (two identical chromophores and one chromophore comprising a group -L-G for coupling with a molecule to be labeled);
  the photophysical properties of the phenylphosphinate ($R_1$=—PO(OH)—$C_6H_5$), methylphosphinate ($R_1$=—PO(OH)$CH_3$) and carboxylate ($R_1$=—COO) europium complexes are similar;
  the hybrid europium complexes in which the chromophores comprise different groups $R_1$, for example in which one of the three groups $R_1$ is a carboxylate group and the other two groups $R_1$ are phenylphosphinate or methylphosphinate groups, have photophysical characteristics identical to those of complexes in which the three groups $R_1$ are identical and are carboxylate groups.

Thus, the results obtained in example 3, namely the fact that these compounds are particularly suited to laser excitation at 337 nm, may be generalized to the other compounds according to the invention, i.e. to the dissymmetric europium complexes and the complexes comprising various groups $R_1$ (carboxylate or phenylphosphinate derivatives).

The invention claimed is:
1. A complexing agent of formula (I):

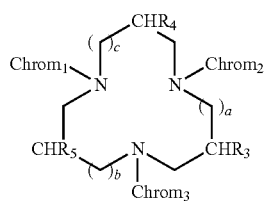

(I)

in which:
either a=b=c=1, or a=b=c=0, or a=1 and b=c=0, or a=b=1 and c=0;
$R_3$, $R_4$, and $R_5$ are each independently H or a group -L-G; and
$Chrom_1$, $Chrom_2$ and $Chrom_3$ are each chromophores of the formula (IIa), or of the formula (IIb), or of the formula (IIc), or of the formula (IId), or of the formula (IIe), or of the formula (IIf), or of the formula (IIg), or of the formula (IIh):

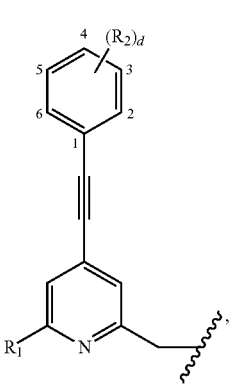

(IIa)

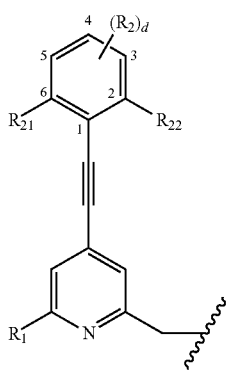

(IIb)

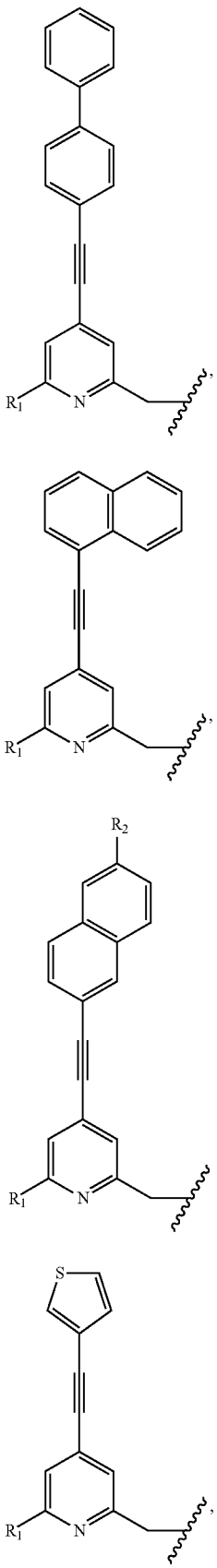

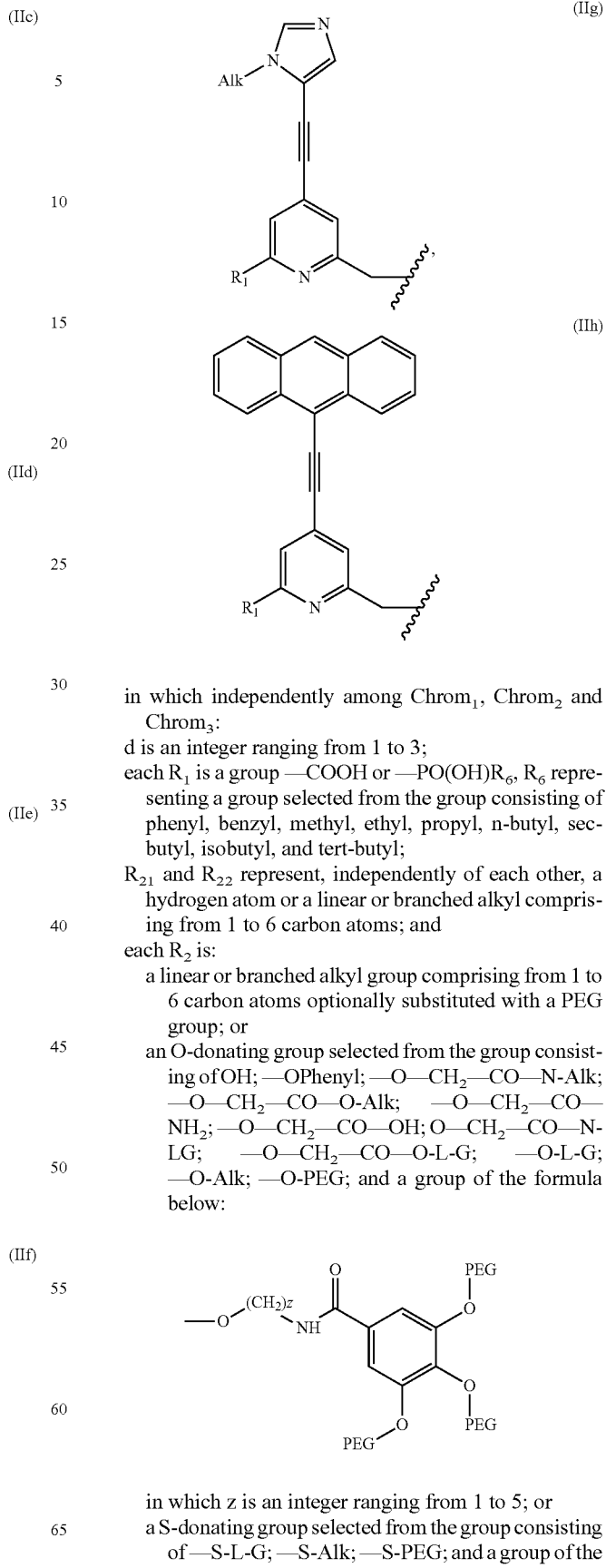

in which independently among Chrom$_1$, Chrom$_2$ and Chrom$_3$:

d is an integer ranging from 1 to 3;

each R$_1$ is a group —COOH or —PO(OH)R$_6$, R$_6$ representing a group selected from the group consisting of phenyl, benzyl, methyl, ethyl, propyl, n-butyl, sec-butyl, isobutyl, and tert-butyl;

R$_{21}$ and R$_{22}$ represent, independently of each other, a hydrogen atom or a linear or branched alkyl comprising from 1 to 6 carbon atoms; and each R$_2$ is:
  a linear or branched alkyl group comprising from 1 to 6 carbon atoms optionally substituted with a PEG group; or
  an O-donating group selected from the group consisting of OH; —OPhenyl; —O—CH$_2$—CO—N-Alk; —O—CH$_2$—CO—O-Alk; —O—CH$_2$—CO—NH$_2$; —O—CH$_2$—CO—OH; O—CH$_2$—CO—N-LG; —O—CH$_2$—CO—O-L-G; —O-L-G; —O-Alk; —O-PEG; and a group of the formula below:

in which z is an integer ranging from 1 to 5; or a S-donating group selected from the group consisting of —S-L-G; —S-Alk; —S-PEG; and a group of the formula below:

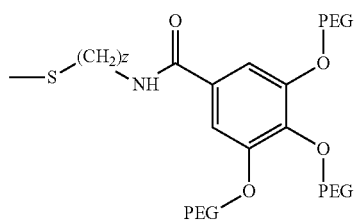

in which z is an integer ranging from 1 to 5; or a NHCO-donating group selected from the group consisting of —NHCO-L-G; —NHCO(OAlk); —NHCO(NHAlk); —NHCO(NAlk$_1$Alk$_2$); —NHCO(SAlk); —NHCO(Alk); —NHCO-PEG; —NHCO-phenyl; and a group of a formula below:

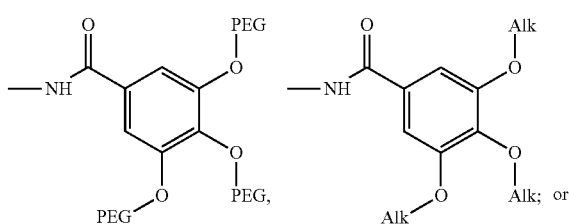

a SCO-donating group selected from the group consisting of —SCO-L-G; —SCO(OAlk); —SCO(NHAlk); —SCO(NAlk$_1$Alk$_2$); —SCO(SAlk); —SCO(Alk); and —SCO-PEG; or a NHCS-donating group selected from the group consisting of —NHCS(OAlk); —NHCS(NHAlk); —NHCS(NAlk$_1$Alk$_2$); —NHCS(SAlk); —NHCS(Alk); —NHCS-PEG; and —NHCS-L-G; or a SCS-donating group selected from the group consisting of —SCS(OAlk); —SCS(NHAlk); —SCS(NAlk$_1$Alk$_2$); —SCS(SAlk); —SCS(Alk); —SCS-PEG; and —SCS-L-G;

wherein PEG is a group of formula —CH$_2$—(CH$_2$OCH$_2$)y-CH$_2$OCH$_3$, y being an integer ranging from 1 to 5;

Alk, Alk$_1$, and Alk$_2$ are each a linear or branched C$_1$-C$_{10}$ alkyl optionally substituted with an —O-PEG group;

L is a spacer arm selected from the group consisting of
a covalent bond;
a linear or branched C$_1$-C$_{20}$ alkylene group, optionally containing one or more double or triple bonds;
a C$_5$-C$_8$ cycloalkylene group;
a C$_6$-C$_{14}$ arylene group; and
combinations thereof,
wherein the alkylene group, the cycloalkylene group, or the arylene group optionally contains one or more heteroatoms, or one or more carbamoyl groups, or one or more carboxamide groups; and
the alkylene group, the cycloalkylene group, or the arylene group is optionally substituted with a C$_1$-C$_8$ alkyl group, a C$_6$-C$_{14}$ aryl group, a sulfonate group, or an oxo group; and G is a reactive group for linking the complex or the complexing agent to a molecule to be labeled, and is selected from the group consisting of acrylamide, activated amine, activated ester, aldehyde, alkyl halide, anhydride, aniline, azide, aziridine, carboxylic acid, diazoalkane, haloacetamide, halotriazine, hydrazine, imido ester, isocyanate, isothiocyanate, maleimide, sulfonyl halide, thiol, ketone, amine, acid halide, succinimidyl ester, hydroxysuccinimidyl ester, hydroxysulfosuccinimidyl ester, azidonitrophenyl, azidophenyl, 3-(2-pyridyldithio)propionamide, glyoxal, triazine, and acetylenic group;

wherein:
when $R_{22}$ and $R_{21}$ are the alkyl groups, then d=1,
when one of the $R_{22}$ and $R_{21}$ groups is the alkyl group and the other is hydrogen, then d=1 or d=2;
when $R_{22}$ and $R_{21}$ are the alkyl groups, then d=1, and
when one of the $R_{22}$ and $R_{21}$ groups is the alkyl group and the other is hydrogen, then d=1 or d=2;
when $R_2$ comprises the group -L-G, then $R_3=R_4=R_5=H$; and
when a plurality of $R_2$ are present, at least one of the $R_2$ groups is in position 4 of a benzene ring to which the at least one $R_2$ is attached.

2. The complexing agent as claimed in claim 1, in which: Chrom$_1$, Chrom$_2$ and Chrom$_3$ are each chromophores of the formula (IIa), or of the formula (IIb), or of the formula (IIc):

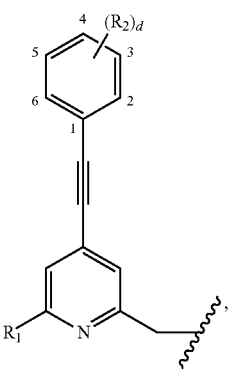
(IIa)

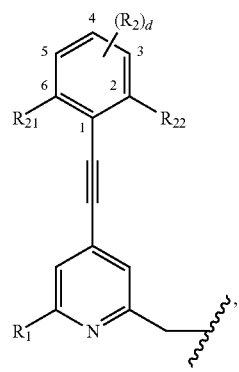
(IIb)

-continued (IIc)

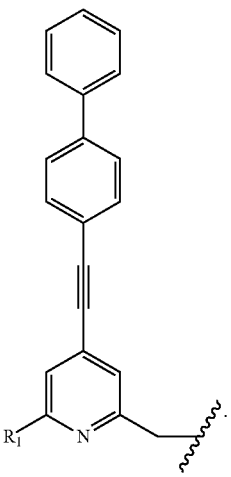

3. The complexing agent as claimed in claim 1, wherein in the formula (I):

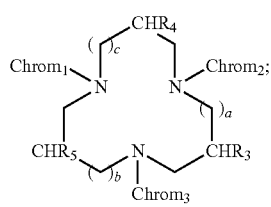

(I)

either a=b=c=1, or a=b=c=0, or a=1 and b=c=0, or a=b=1 and c=0;
$R_3$, $R_4$ and $R_5$ are each independently H or the group -L-G; and
$Chrom_1$, $Chrom_2$ and $Chrom_3$ are each chromophores of the formula (IIa):

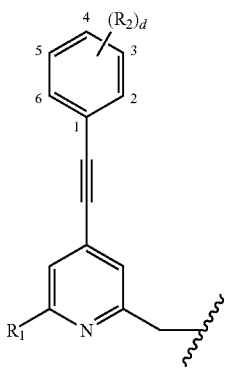

(IIa)

in which independently among $Chrom_1$, $Chrom_2$ and $Chrom_3$:
d is an integer ranging from 1 to 3;
$R_1$ is a group —COOH or —PO(OH)$R_6$, wherein $R_6$ represents a group selected from the group consisting of phenyl, benzyl, methyl, ethyl, propyl, n-butyl, sec-butyl, isobutyl, and tert-butyl; and
each $R_2$ is:
a linear or branched alkyl group comprising from 1 to 6 carbon atoms optionally substituted with a PEG group; or
an O-donating group selected from the group consisting of —O-L-G; —O-Alk; —O-PEG; and the group of the formula below:

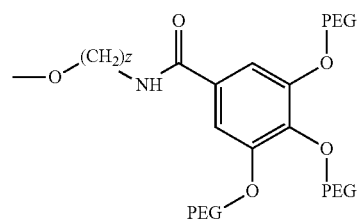

in which z is an integer ranging from 1 to 5; or
a S-donating group selected from the group consisting of —S-L-G; —S-Alk; —S-PEG; and the group of the formula below:

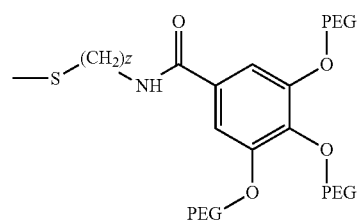

in which z is an integer between 1 and 5; or
a NHCO-donating group selected from: —NHCO-L-G; —NHCO(OAlk); —NHCO(NHAlk); —NHCO(NAlk$_1$Alk$_2$); —NHCO(SAlk); —NHCO(Alk); —NHCO-PEG; and the group of the formula below:

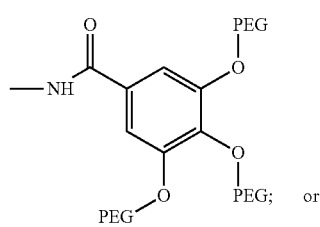

or a SCO-donating group selected from the group consisting of —SCO-L-G; —SCO(OAlk); —SCO(NHAlk); —SCO(NAlk$_1$Alk$_2$); —SCO(SAlk); —SCO(Alk); and —SCO-PEG; or
a NHCS-donating group selected from the group consisting of —NHCS(OAlk); —NHCS(NHAlk); —NHCS(NAlk$_1$Alk$_2$); —NHCS(SAlk); —NHCS(Alk); —NHCS-PEG; and —NHCS-L-G; or
a SCS-donating group selected from the group consisting of —SCS(OAlk); —SCS(NHAlk); —SCS(NAlk$_1$Alk$_2$); —SCS(SAlk); —SCS(Alk); —SCS-PEG; and —SCS-L-G;
wherein PEG is a group of formula —CH$_2$—(CH$_2$OCH$_2$)$_y$—CH$_2$OCH$_3$, y being an integer ranging from 1 to 5;
Alk, Alk$_1$ and Alk$_2$ are each a linear or branched C$_1$-C$_{10}$ alkyl optionally substituted with an —O-PEG group;

L is a spacer arm as defined in claim 1;
G is a reactive group for linking the complex or the complexing agent to a molecule to be labeled, as defined in claim 1;
wherein:
when $R_2$ comprises the group -L-G, then $R_3=R_4=R_5=H$;
when $R_2$ does not comprise the group -L-G, then either one of the groups $R_3$, $R_4$ and $R_5$ is the group -L-G, or $R_3=R_4=R_5=H$; and
when a plurality of $R_2$ are present, at least one of the $R_2$ groups is in position 4 of the benzene ring to which the at least one $R_2$ is attached.

4. The complexing agent as claimed in claim 1, wherein:
either two of the groups $Chrom_1$, $Chrom_2$ and $Chrom_3$ are identical and are each substituted with one to three groups $R_2$, which do not comprise the group -L-G and the third chromophore is substituted with a group $R_2$ comprising the group -L-G, and the groups $R_3$-$R_5$ are hydrogen atoms; or
$Chrom_1$, $Chrom_2$ and $Chrom_3$ are identical and are each substituted with one to three groups $R_2$, which do not comprise the group -L-G, and the groups $R_3$-$R_5$ are hydrogen atoms; or
$Chrom_1$, $Chrom_2$ and $Chrom_3$ are identical and are substituted with one to three groups $R_2$, which do not comprise the group -L-G, and one of the groups $R_3$-$R_5$ is the group L-G, the other groups $R_3$-$R_5$ being hydrogen atoms.

5. The complexing agent as claimed in claim 1, wherein one of the groups $R_2$ comprises the group -L-G.

6. The complexing agent as claimed in claim 1, wherein one of the groups $R_3$, $R_4$ and $R_5$ is the group -L-G.

7. The complexing agent as claimed in claim 1, which does not comprise the group -L-G.

8. The complexing agent as claimed in claim 1, wherein the formula (I) satisfies a=b=c=0.

9. The complexing agent as claimed in claim 1, wherein the groups $R_1$ of the chromophores $Chrom_1$, $Chrom_2$ and $Chrom_3$ are —COOH groups.

10. The complexing agent as claimed in claim 1, wherein the groups $R_1$ of the chromophores $Chrom_1$, $Chrom_2$ and $Chrom_3$ are the —PO(OH)$R_6$ groups.

11. The complexing agent as claimed in claim 1, wherein the group $R_1$ of the chromophore $Chrom_1$ is a —COOH group and the groups $R_1$ of the chromophores $Chrom_2$ and $Chrom_3$ are the —PO(OH)$R_6$ groups.

12. The complexing agent as claimed in claim 1, wherein the group $R_1$ of the chromophore $Chrom_1$ is the —PO(OH)$R_6$ group, and
the groups $R_1$ of the chromophores $Chrom_2$ and $Chrom_3$ are —COOH groups.

13. The complexing agent as claimed in claim 1, wherein the groups $R_2$ are the O-donating groups selected from the group consisting of —O-L-G; —O-Alk; —O-PEG; and the group of the formula below:

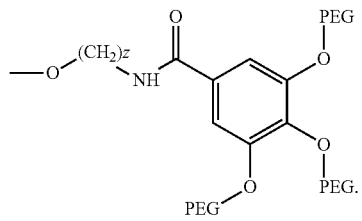

14. The complexing agent as claimed in claim 1, wherein the groups $R_2$ are the NHCO-donating groups selected from the group consisting of
—NHCO-L-G; —NHCO(OAlk); —NHCO(NHAlk); —NHCO(NAlk$_1$Alk$_2$); —NHCO(SAlk); —NHCO (Alk); —NHCO-PEG; and the group of the formula below:

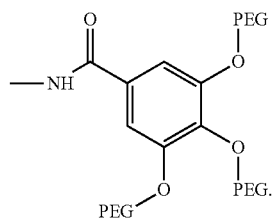

15. The complexing agent as claimed in claim 1, which comprises at least one PEG group.

16. The complexing agent as claimed in claim 1, wherein the reactive group G is a group selected from the group consisting of formulae:

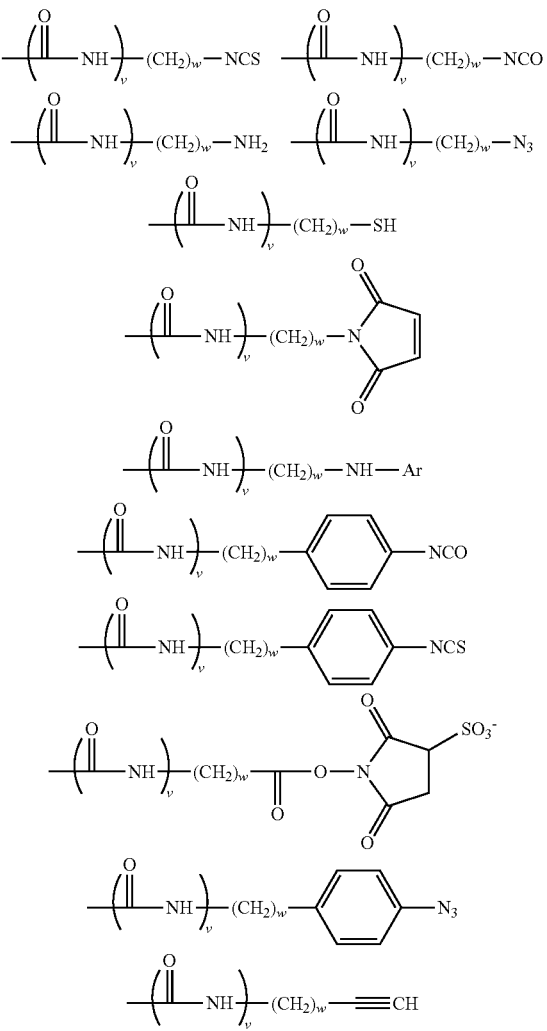

-continued

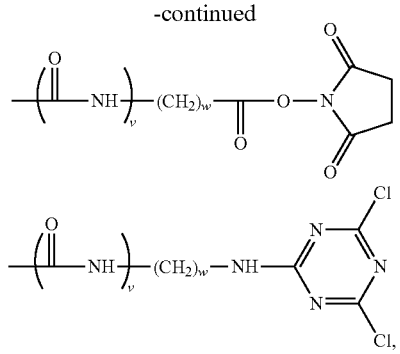

in which w ranges from 0 to 8 and v is equal to 0 or 1, and Ar is a saturated or unsaturated 5- or 6-membered heterocycle, comprising from 1 to 3 heteroatoms, optionally substituted with a halogen atom.

17. The complexing agent as claimed in claim 1, wherein the spacer arm L is selected from the group consisting of the following groups:

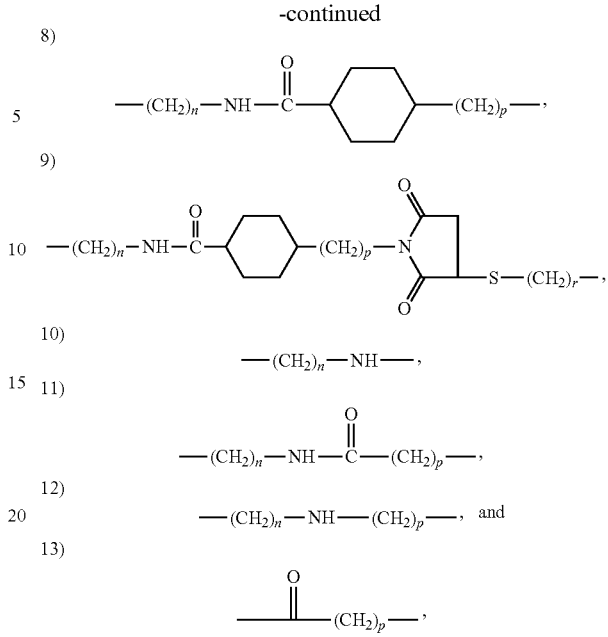

in which n, m, p, and r are integers from 1 to 16.

18. The complexing agent as claimed in claim 1,
wherein the group -L-G consists of the reactive group G selected from the group consisting of a carboxylic acid, an amine, a succinimidyl ester, a haloacetamide, a hydrazine, an isothiocyanate, and a maleimide group,
wherein the spacer arm L thereof consists of an alkylene chain comprising from 1 to 5 carbon atoms.

19. A lanthanide complex comprising the complexing agent as claimed in claim 1 and a lanthanide.

20. The lanthanide complex as claimed in claim 19, wherein the lanthanide is $Eu^{3+}$, $Tb^{3+}$, $Gd^{3+}$, $Dy^{3+}$, $Nd^{3+}$, or $Er^{3+}$.

21. A fluorescent conjugate between a molecule of interest selected from the group consisting of an organic molecule, a peptide, and a protein, and the lanthanide complex as claimed in claim 19.

22. The lanthanide complex as claimed in claim 19, wherein said lanthanide is $Eu^{3+}$.

23. The fluorescent conjugate as claimed in claim 21, wherein the lanthanide of the lanthanide complex is $Eu^{3+}$, $Tb^{3+}$, $Gd^{3+}$, $Dy^{3+}$, $Nd^{3+}$, or $Er^{3+}$.

24. The complexing agent as claimed in claim 18, wherein the reactive group G is an amine.

25. The complexing agent as claimed in claim 24, wherein said amine is an aliphatic amine.

* * * * *